United States Patent
Harima

(10) Patent No.: US 7,597,789 B2
(45) Date of Patent: Oct. 6, 2009

(54) OXIDATION-REDUCTION POTENTIOMETER

(75) Inventor: Shinichi Harima, Daisem (JP)

(73) Assignee: Tanita Corporation, Tokyo (JP)

( * ) Notice: Subject to any disclaimer, the term of this patent is extended or adjusted under 35 U.S.C. 154(b) by 879 days.

(21) Appl. No.: 11/133,334

(22) Filed: May 20, 2005

(65) Prior Publication Data

US 2005/0258038 A1    Nov. 24, 2005

(30) Foreign Application Priority Data

May 21, 2004    (JP) .............................. 2004-151750

(51) Int. Cl.
*G01N 27/26* (2006.01)
(52) U.S. Cl. .................................. 204/406; 422/82.01
(58) Field of Classification Search .................. 204/412, 204/416, 406; 205/775; 422/82.01, 82.02, 422/82.03; 702/42, 170
See application file for complete search history.

(56) References Cited

U.S. PATENT DOCUMENTS

| | | | | |
|---|---|---|---|---|
| 4,952,300 | A | * | 8/1990 | Diamond ................... 204/406 |
| 5,103,179 | A | * | 4/1992 | Thomas et al. .............. 324/438 |
| 5,382,331 | A | * | 1/1995 | Banks ........................ 205/781 |
| 2006/0060475 | A1 | * | 3/2006 | Applegate et al. ........... 205/775 |

FOREIGN PATENT DOCUMENTS

| | | | |
|---|---|---|---|
| JP | H11-064275 | * | 8/1997 |
| JP | 11-9566 | | 1/1999 |
| JP | 11-64275 | | 3/1999 |
| JP | 2002-214220 | * | 1/2001 |

* cited by examiner

*Primary Examiner*—Nam X Nguyen
*Assistant Examiner*—J. Christopher Ball
(74) *Attorney, Agent, or Firm*—McDermott Will & Emery LLP

(57) ABSTRACT

An oxidation-reduction potentiometer immerses a working electrode and a reference electrode in a reference liquid, measures an interelectrode voltage between the above electrodes when an impedance reducing circuit is unconnected and an interelectrode voltage between the above electrodes when the impedance reducing circuit is connected by interelectrode voltage measuring means, computes a comparison coefficient based on the measured voltages by a comparison coefficient computing section, stores the coefficient in a comparison coefficient storing section, immerses the working electrode and the reference electrode in a test liquid, measures an interelectrode voltage between the working electrode and the reference electrode when the impedance reducing circuit is connected by the measuring means, and computes an oxidation-reduction potential by an oxidation-reduction potential computing section based on the measured voltage when the impedance reducing circuit is connected and the coefficient stored in the storing section.

9 Claims, 29 Drawing Sheets

OXIDATION-REDUCTION POTENTIOMETER

BACKGROUND OF THE INVENTION (i) Field of the Invention

The present invention relates to an oxidation-reduction potentiometer which measures the oxidation-reduction potential of any type of water including domestic water, industrial water, natural water and a scientific solution conveniently and accurately.

(ii) Description of the Related Art

In recent years, there is provided or disclosed an oxidation-reduction potentiometer that immerses a working electrode which comprises a noble metal such as platinum (Pt) or gold (Au) and a reference electrode which comprises sodium chloride (NaCl) or potassium chloride (KCl) and has a metal portion formed of silver (Ag) and silver chloride (AgCl) immersed in a gelled or liquid internal liquid in a test liquid to measure a voltage between the working electrode and the reference electrode which is generated from an oxidation-reduction reaction.

The oxidation-reduction potentiometer presents an oxidation-reduction potential value through processes such as amplification and A/D conversion, while retaining the voltage between the working electrode and the reference electrode, i.e., the difference between a potential generated from the working electrode and a potential generated from the reference electrode as it is (refer to Patent Publication 1 or Patent Publication 2, for example).

Patent Publication 1
  Japanese Patent Laid-Open Publication No. 64275/1999

Patent Publication 2
  Japanese Patent Laid-Open Publication No. 9566/1999

However, the oxidation-reduction potentiometer has problems that nonlinearity and repeatability of the potentials generated from the electrodes with respect to a given concentration of substance are unsatisfactory due to instability of the reaction between the metal electrodes and the test liquid and that it takes a long measuring time.

Thus, an object of the present invention is to solve the above problems of the prior art and provide an oxidation-reduction potentiometer having its convenience improved by an improvement in measurement accuracy, a reduction in measuring time, and the like.

SUMMARY OF THE INVENTION

An oxidation-reduction potentiometer of the present invention comprises:
a working electrode,
a reference electrode,
an impedance reducing circuit, and
oxidation-reduction potential measuring means,
wherein
the working electrode generates a potential indicating the degree of oxidation-reduction reaction when immersed in a liquid, the reference electrode generates a reference potential when immersed in the liquid,
the impedance reducing circuit reduces an impedance which occurs between the working electrode and the reference electrode when the electrodes are immersed in the liquid, and
the oxidation-reduction potential measuring means measures an oxidation-reduction potential based on an interelectrode voltage which is a difference between the potential generated from the working electrode and indicating the degree of oxidation-reduction reaction and the reference potential generated from the reference electrode in reducing the impedance by the impedance reducing circuit.

Further, the oxidation-reduction potential measuring means comprises:
reducing circuit switching means,
interelectrode voltage measuring means,
a comparison coefficient computing section,
a comparison coefficient storing section, and
an oxidation-reduction potential computing section,
wherein
the reducing circuit switching means switches the impedance reducing circuit to an unconnected state and to a connected state between the working electrode and the reference electrode, the interelectrode voltage measuring means measures an interelectrode voltage which is a difference between a potential generated from the working electrode and indicating the degree of oxidation-reduction reaction and a reference potential generated from the reference electrode, when the impedance reducing circuit has been switched to the unconnected state and the connected state by the reducing circuit switching means, the comparison coefficient computing section computes a comparison coefficient based on the interelectrode voltage in the unconnected state and the interelectrode voltage in the connected state which have been measured by the interelectrode voltage measuring means,
the comparison coefficient storing section stores the comparison coefficient computed by the comparison coefficient computing section, and
the oxidation-reduction potential computing section computes an oxidation-reduction potential based on the interelectrode voltage in the connected state which has been measured by the interelectrode voltage measuring means when the impedance reducing circuit has been switched to the connected state by the reducing circuit switching means and the comparison coefficient stored in the comparison coefficient storing section.

Further, the oxidation-reduction potentiometer further comprises:
conductivity measuring means, and
conductivity measurement switching means,
wherein
the conductivity measuring means measures the conductivity of the liquid,
the conductivity measurement switching means switches between measurement of interelectrode voltage by the interelectrode voltage measuring means and measurement of conductivity by the conductivity measuring means,
the comparison coefficient storing section stores comparison coefficients for a plurality of liquids having different conductivities which have been computed by the comparison coefficient computing section based on switching between the measurement of interelectrode voltage and the measurement of conductivity by the conductivity measurement switching means, and
the oxidation-reduction potential computing section computes an oxidation-reduction potential based on an interelectrode voltage in a connected state which has been measured by the interelectrode voltage measuring means when the impedance reducing circuit has been switched to the connected state by the reducing circuit switching means and a comparison coefficient corresponding to the conductivity of the liquid measured by the conductivity measuring means out of the comparison coefficients for the liquids having different conductivities stored in the comparison coefficient storing section.

Further, the oxidation-reduction potentiometer further comprises:

water immersion measuring means, wherein the water immersion measuring means measures that the working electrode and the reference electrode are immersed in the liquid, prior to measurement of the oxidation-reduction potential by the oxidation-reduction potential measuring means, and the reducing circuit switching means keeps the impedance reducing circuit switched to an unconnected state during the measurement by the water immersion measuring means.

The working electrode comprises a plurality of working electrodes having different areas, the potentiometer further comprises working electrode switching means for switching connection to the interelectrode voltage measuring means to a working electrode out of the working electrodes having different areas, the impedance reducing circuit reduces an impedance occurring between each of the working electrodes having different areas and the reference electrode, the reducing circuit switching means switches the impedance reducing circuit to an unconnected state and to a connected state between each of the working electrodes having different areas and the reference electrode, the interelectrode voltage measuring means measures an interelectrode voltage which is a difference between a potential indicating the degree of oxidation-reduction reaction and generated from each of the working electrodes having different areas and a reference potential generated from the reference electrode, when the impedance reducing circuit has been switched to the unconnected state and the connected state by the reducing circuit switching means, the comparison coefficient computing section computes a comparison coefficient based on the interelectrode voltage in the unconnected state and the interelectrode voltage in the connected state which have been measured by the interelectrode voltage measuring means, the comparison coefficient storing section stores the comparison coefficients computed by the comparison coefficient computing section, and the oxidation-reduction potential computing section computes an oxidation-reduction potential based on the interelectrode voltage in the connected state which has been measured by the interelectrode voltage measuring means when the impedance reducing circuit has been switched to the connected state by the reducing circuit switching means and a corresponding comparison coefficient out of the comparison coefficients stored in the comparison coefficient storing section, the computation of the oxidation-reduction potential being performed for each of the working electrodes having different areas in the order of area from smallest to largest.

Further, the impedance reducing circuit connects the working electrode and the reference electrode only by a reduction resistance.

Further, the impedance reducing circuit comprises:

voltage generating circuits which generate a voltage, a voltage follower which is connected to the voltage generating circuits, and an output resistance which is connected between the voltage follower and the working electrode.

Further, the impedance reducing circuit reduces an impedance occurring between the working electrode and the reference electrode in multiple levels, the reducing circuit switching means switches the impedance reducing circuit to a connected state in multiple levels, the interelectrode voltage measuring means measures an interelectrode voltage of each level when the impedance reducing circuit has been switched to the connected state in multiple levels, the comparison coefficient computing section computes a comparison coefficient of each level based on the interelectrode voltage of the corresponding level in the connected state which has been measured by the interelectrode voltage measuring means, the comparison coefficient storing section stores the comparison coefficient of each level which has been computed by the comparison coefficient computing section, and the oxidation-reduction potential computing section computes an oxidation-reduction potential value based on an interelectrode voltage in a connected state which has been measured by the interelectrode voltage measuring means when the impedance reducing circuit has been switched to the connected state of a specific level by the reducing circuit switching means and a comparison coefficient of the corresponding level out of the comparison coefficients of multiple levels stored in the comparison coefficient storing section.

Further, the impedance reducing circuit connects the working electrode and the reference electrode in parallel only by a plurality of reduction resistances.

Further, the impedance reducing circuit comprises:

voltage generating circuits which generate a voltage in multiple levels, a voltage follower which is connected to the voltage generating circuits, and an output resistance which is connected between the voltage follower and the working electrode.

The oxidation-reduction potentiometer of the present invention immerses the working electrode and the reference electrode in a reference liquid and measures an oxidation-reduction potential based on an interelectrode voltage in reducing an impedance by the impedance reducing circuit by the oxidation-reduction potential measuring means. More specifically, the oxidation-reduction potentiometer of the present invention immerses the working electrode and the reference electrode in a reference liquid, measures an interelectrode voltage when the impedance reducing circuit is in an unconnected state between the working electrode and the reference electrode and an interelectrode voltage when the impedance reducing circuit is in a connected state between the working electrode and the reference electrode by the interelectrode voltage measuring means, computes a comparison coefficient based on these measured interelectrode voltages by the comparison coefficient computing section, stores the comparison coefficient in the comparison coefficient storing section, immerses the working electrode and the reference electrode in a test liquid, measures an interelectrode voltage when the impedance reducing circuit is in a connected state between the working electrode and the reference electrode by the interelectrode voltage measuring means, and computes an oxidation-reduction potential based on the measured interelectrode voltage in the connected state and the comparison coefficient stored in the comparison coefficient storing section by the oxidation-reduction potential computing section. Thus, when the impedance reducing circuit is in a connected state between the working electrode and the reference electrode, a current passes between the electrodes and the electrodes undergo a stable reaction. Hence, it has such advantages as improvements in nonlinearity and repeatability and a reduction in measuring time.

Further, the oxidation-reduction potentiometer of the present invention measures the conductivities of reference liquids having different conductivities by the conductivity measuring means, stores comparison coefficients for the reference liquids having different conductivities in the comparison coefficient storing section, measures the conductivity of a test liquid by the conductivity measuring means, and computes an oxidation-reduction potential by the oxidation-reduction potential computing section by use of a comparison coefficient stored in the comparison coefficient storing section and corresponding to the conductivity of the test liquid. Thus, since an oxidation-reduction potential corresponding to the conductivity of a test liquid can be obtained, it has an advantage of obtaining the oxidation-reduction potential more accurately.

Further, the oxidation-reduction potentiometer of the present invention measures that the working electrode and the reference electrode are immersed in a liquid by the water immersion measuring means prior to measurement of oxidation-reduction potential by the oxidation-reduction potential measuring means and has the impedance reducing circuit switched to an unconnected state while measuring that the electrodes are immersed in the liquid. Thus, since the impedance reducing circuit is in an unconnected state while the working electrode and the reference electrode are immersed in a liquid prior to measurement of oxidation-reduction potential, a current does not pass between the electrodes, and the electrodes do not cause a chemical reaction. Hence, it has an advantage of extending the useful lives of the electrodes.

Further, the oxidation-reduction potentiometer of the present invention immerses each of the working electrodes and the reference electrode in a reference liquid, measures an interelectrode voltage when the impedance reducing circuit is in an unconnected state between each of the working electrodes and the reference electrode and an interelectrode voltage when the impedance reducing circuit is in a connected state between the working electrode and the reference electrode by the interelectrode voltage measuring means, computes comparison coefficients based on these measured interelectrode voltages by the comparison coefficient computing section, stores the comparison coefficients in the comparison coefficient storing section, immerses each of the working electrodes and the reference electrode in a test liquid, measures an interelectrode voltage when the impedance reducing circuit is in a connected state between the working electrode having the smallest area and the reference electrode by the interelectrode voltage measuring means (this measurement is also made on the other working electrodes as well in the order of area from next smallest to largest), and computes an oxidation-reduction potential by the oxidation-reduction potential computing section based on the measured interelectrode voltage in the connected state and the comparison coefficient stored in the comparison coefficient storing section. When the area of the working electrode is large, the reaction is stable but slow due to charge and discharge of the electric double layer on the surface of the working electrode. Thus, since a measurement starts from small working electrodes which exhibit a higher reaction rate than working electrodes having large areas, it has an advantage of further reducing measuring time.

Further, the oxidation-reduction potentiometer of the present invention immerses the working electrode and the reference electrode in a reference liquid, measures an interelectrode voltage of each level when the impedance reducing circuit which is reduced in multiple levels is in an unconnected state between the working electrode and the reference electrode and an interelectrode voltage of the level when the impedance reducing circuit is in a connected state between the working electrode and the reference electrode by the interelectrode voltage measuring means, computes a comparison coefficient of each level based on these measured interelectrode voltages of the corresponding level by the comparison coefficient computing section, stores the comparison coefficients in the comparison coefficient storing section, immerses the working electrode and the reference electrode in a test liquid, measures an interelectrode voltage of each level when the impedance reducing circuit which is reduced in multiple levels is in a connected state between the working electrode and the reference electrode by the interelectrode voltage measuring means, and computes an oxidation-reduction potential based on the measured interelectrode voltage of each level in the connected state and a comparison coefficient of the corresponding level out of the comparison coefficients of multiple levels stored in the comparison coefficient storing section. Thus, since the range of the concentration which influences the oxidation-reduction reaction expands stepwise according to stepwise reduction of the impedance reducing circuit, it has an advantage of wide measurement range.

DETAILED DESCRIPTION OF THE PREFERRED EMBODIMENTS

Figure 1:
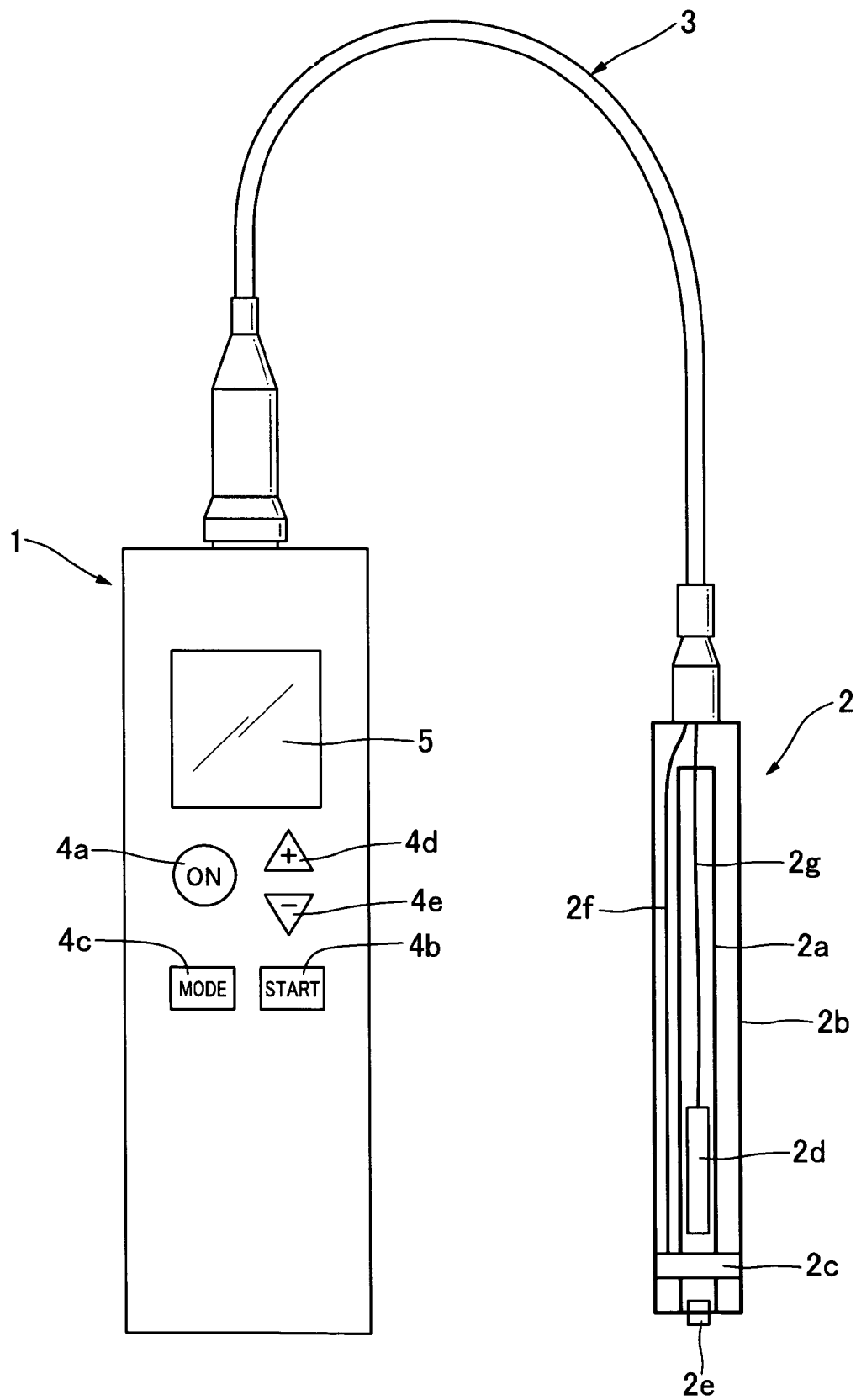
FIG. 1 is an external view of an oxidation-reduction potentiometer. (Examples 1, 2 and 3)

An oxidation-reduction potentiometer of the present invention comprises a working electrode, a reference electrode, an impedance reducing circuit and oxidation-reduction potential measuring means.

The working electrode generates a potential indicating the degree of oxidation-reduction reaction when immersed in a liquid (reference liquid or text liquid). The reference electrode generates a reference potential when immersed in a liquid.

The impedance reducing circuit reduces an impedance occurring between the working electrode and the reference electrode when the electrodes are immersed in a liquid.

The oxidation-reduction potential measuring means comprises reducing circuit switching means, interelectrode voltage measuring means, a comparison coefficient computing section, a comparison coefficient storing section and an oxidation-reduction potential computing section. The oxidation-reduction potential measuring means measures an oxidation-reduction potential based on an interelectrode voltage which is a difference between a potential generated from the working electrode and indicating the degree of oxidation-reduction reaction and a reference potential generated from the reference electrode when an impedance is reduced by the impedance reducing circuit.

More specifically, the reducing circuit switching means switches the impedance reducing circuit to a connected state and an unconnected state between the working electrode and the reference electrode.

The interelectrode voltage measuring means measures an interelectrode voltage which is a difference between a potential generated from the working electrode and indicating the degree of oxidation-reduction reaction and a reference potential generated from the reference electrode when the impedance reducing circuit has been switched to an unconnected state by the reducing circuit switching means. The interelectrode voltage measuring means also measures an interelectrode voltage which is a difference between a potential generated from the working electrode and indicating the degree of oxidation-reduction reaction and a reference potential generated from the reference electrode when the impedance reducing circuit has been switched to a connected state by the reducing circuit switching means.

The comparison coefficient computing section computes a comparison coefficient based on the interelectrode voltage in the unconnected state and the interelectrode voltage in the connected state which have been measured by the interelectrode voltage measuring means. The comparison coefficient storing section stores the comparison coefficient computed by the comparison coefficient computing section.

The oxidation-reduction potential computing section computes an oxidation-reduction potential based on the interelectrode voltage in the connected state which has been measured by the interelectrode voltage measuring means when the impedance reducing circuit has been switched to the connected state by the reducing circuit switching means and the comparison coefficient stored in the comparison coefficient storing section.

The thus constituted oxidation-reduction potentiometer immerses the working electrode and the reference electrode in a reference liquid, measures an interelectrode voltage when the impedance reducing circuit is in an unconnected state between the working electrode and the reference electrode and an interelectrode voltage when the impedance reducing circuit is in a connected state between the working electrode and the reference electrode by the interelectrode voltage measuring means, computes a comparison coefficient based on these measured interelectrode voltages by the comparison coefficient computing section, stores the comparison coefficient in the comparison coefficient storing section, immerses the working electrode and the reference electrode in a test liquid, measures an interelectrode voltage when the impedance reducing circuit is in a connected state between the working electrode and the reference electrode by the interelectrode voltage measuring means, and can compute an oxidation-reduction potential based on the measured interelectrode voltage in the connected state and the comparison coefficient stored in the comparison coefficient storing section by the oxidation-reduction potential computing section. Thus, when the impedance reducing circuit is in a connected state between the working electrode and the reference electrode, a current passes between the electrodes and the electrodes undergo a stable reaction. Hence, the oxidation-reduction potentiometer of the present invention has such advantages as improvements in nonlinearity and repeatability and a reduction in measuring time.

Figure 25:
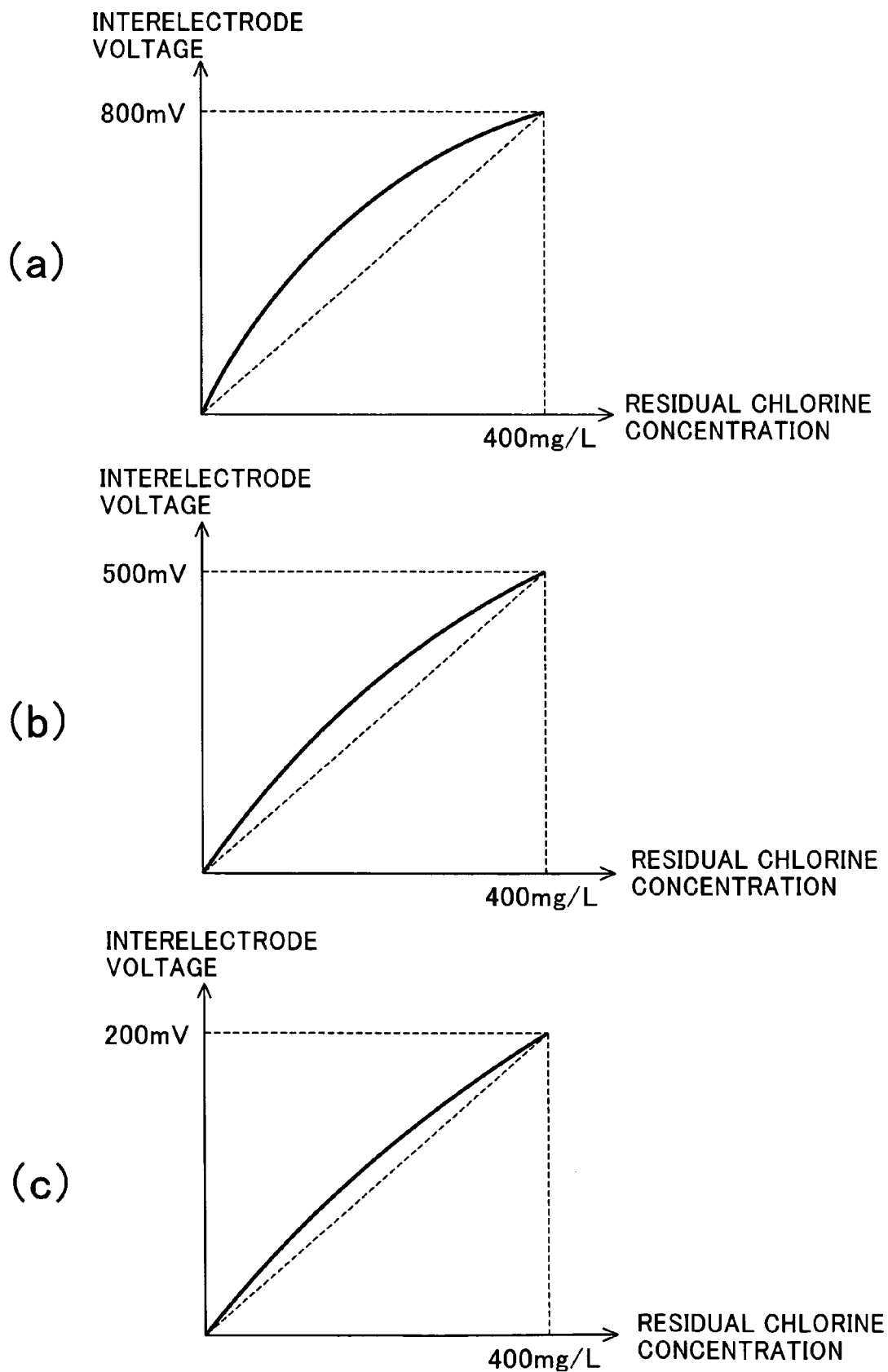
FIG. 25 is graphs illustrating influence on nonlinearity.

Hereinafter, the improvement in nonlinearity will be described briefly by use of the graphs of FIG. 25. FIG. 25($a$) shows the result of measurement with the vertical axis representing an interelectrode voltage when the impedance reducing circuit is in an unconnected state between the working electrode and the reference electrode and the horizontal axis representing the concentration of residual chlorine which influences an oxidation-reduction reaction. FIGS. 25($b$) and 25($c$) show the results of measurements with the vertical axis representing an interelectrode voltage when the impedance reducing circuit (load constant in (b) is different from that in (c)) is in a connected state between the working electrode and the reference electrode and the horizontal axis representing the concentration of residual chlorine which influences an oxidation-reduction reaction. As shown in these figures, nonlinearity improves by changing according to the size of the load constant (resistance value) of the impedance reducing circuit which is in a connected state between the working electrode and the reference electrode.

Figure 26:
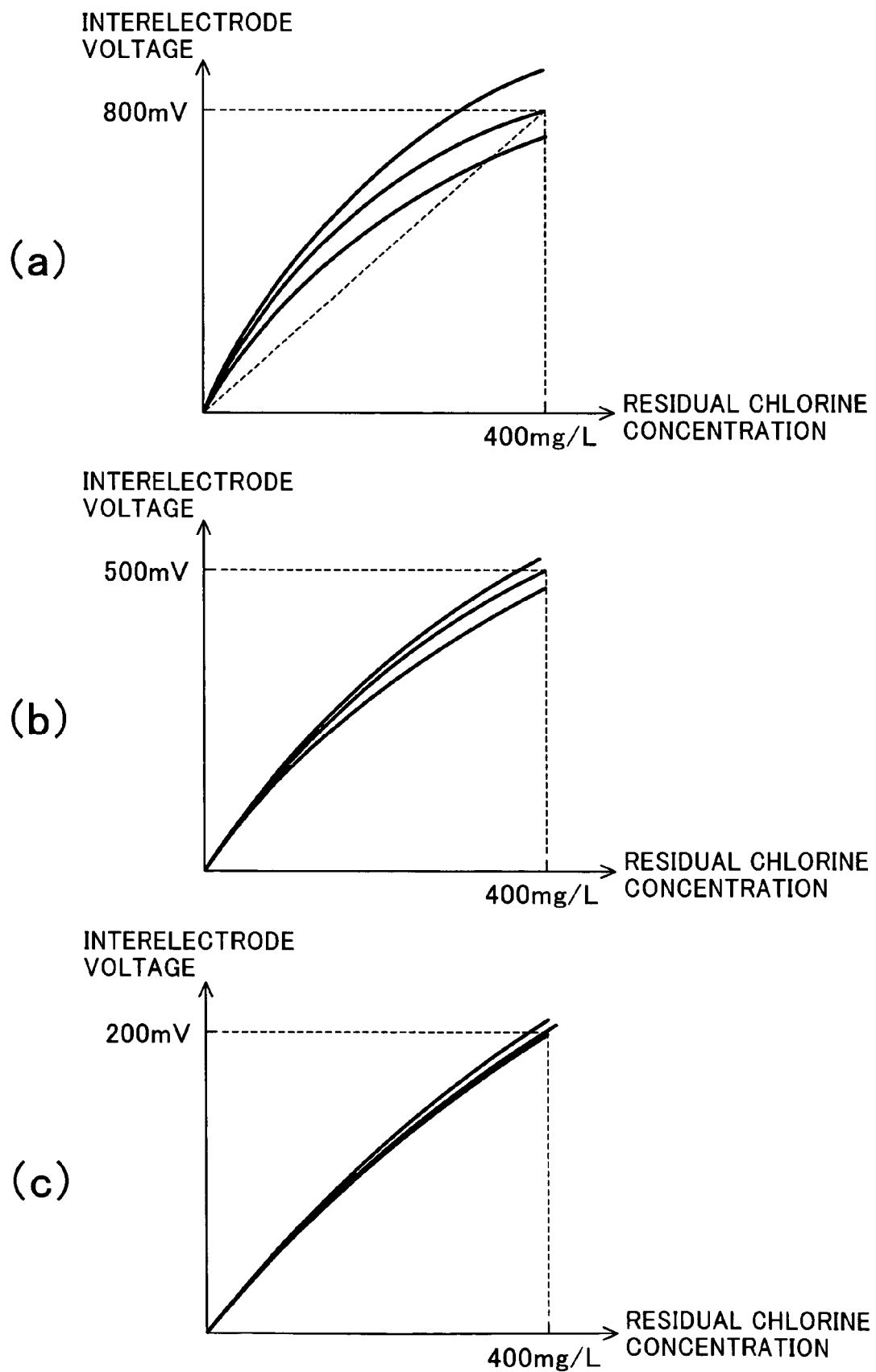
FIG. 26 is graphs illustrating influence on repeatability.

Further, the improvement in repeatability will be described briefly by use of the graphs of FIG. 26. FIG. 26($a$) shows the results of repeated measurements with the vertical axis representing an interelectrode voltage when the impedance reducing circuit is in an unconnected state between the working electrode and the reference electrode and the horizontal axis representing the concentration of residual chlorine which influences an oxidation-reduction reaction. FIGS. 26($b$) and 26($c$) show the results of repeated measurements with the vertical axis representing an interelectrode voltage when the impedance reducing circuit (load constant in (b) is different from that in (c)) is in a connected state between the working electrode and the reference electrode and the horizontal axis representing the concentration of residual chlorine which influences an oxidation-reduction reaction. As shown in these figures, repeatability improves by changing according to the size of the load constant (resistance value) of the impedance reducing circuit which is in a connected state between the working electrode and the reference electrode.

Figure 27:
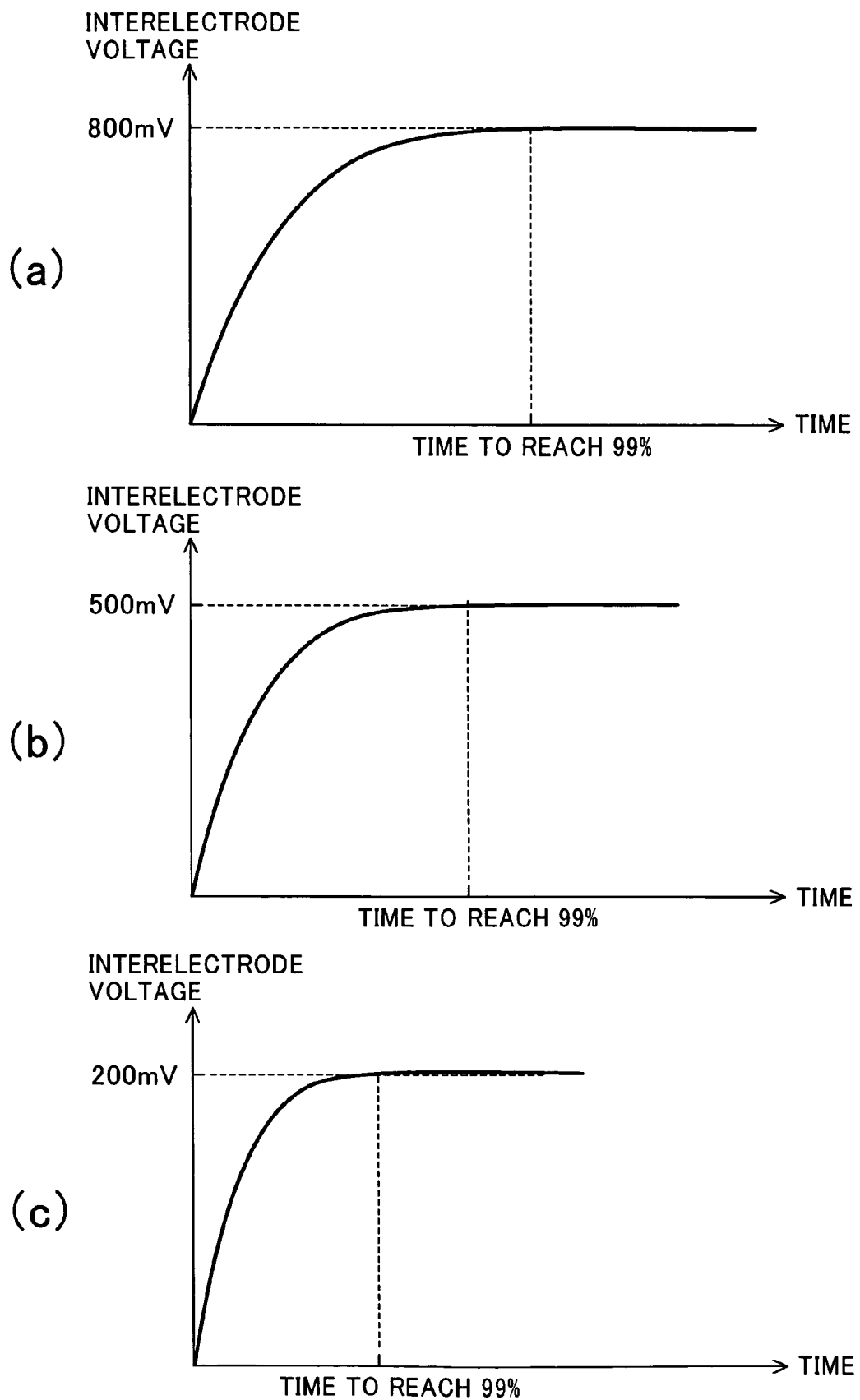
FIG. 27 is graphs illustrating influence on measuring time.

Further, the reduction in measuring time will be described briefly by use of the graphs of FIG. 27. FIG. 27(a) shows the result of measurement with the vertical axis representing an interelectrode voltage when the impedance reducing circuit is in an unconnected state between the working electrode and the reference electrode and the horizontal axis representing measuring time. FIGS. 27(b) and 27(c) show the results of measurements with the vertical axis representing an interelectrode voltage when the impedance reducing circuit (load constant in (b) is different from that in (c)) is in a connected state between the working electrode and the reference electrode and the horizontal axis representing measuring time. As shown in these figures, measuring time shortens by changing according to the size of the load constant (resistance value) of the impedance reducing circuit which is in a connected state between the working electrode and the reference electrode.

The thus constituted oxidation-reduction potentiometer will be specifically described in Example 1 which will be described later.

Further, the oxidation-reduction potentiometer of the present invention may also be constituted such that the potentiometer further comprises conductivity measuring means for measuring the conductivity of a liquid and conductivity measurement switching means for switching between measurement of conductivity by the conductivity measuring means and measurement of interelectrode voltage by the interelectrode voltage measuring means, the comparison coefficient storing section stores comparison coefficients for liquids having different conductivities which have been computed by the comparison coefficient computing section based on switching between the measurement of interelectrode voltage and the measurement of conductivity by the conductivity measurement switching means, and the oxidation-reduction potential computing section computes an oxidation-reduction potential based on an interelectrode voltage in a connected state which has been measured by the interelectrode voltage measuring means when the impedance reducing circuit has been switched to the connected state by the reducing circuit switching means and a comparison coefficient corresponding to the conductivity of the liquid measured by the conductivity measuring means out of the comparison coefficients for the liquids having different conductivities stored in the comparison coefficient storing section.

The thus constituted oxidation-reduction potentiometer measures the conductivities of reference liquids having different conductivities by the conductivity measuring means, stores comparison coefficients for the reference liquids having different conductivities in the comparison coefficient storing section, measures the conductivity of a test liquid by the conductivity measuring means, and can compute an oxidation-reduction potential by the oxidation-reduction potential computing section by use of a comparison coefficient stored in the comparison coefficient storing section and corresponding to the conductivity of the test liquid. Thus, since an oxidation-reduction potential corresponding to the conductivity of a test liquid can be obtained. Hence, the oxidation-reduction potentiometer of the present invention has an advantage of obtaining the oxidation-reduction potential more accurately.

Figure 29:
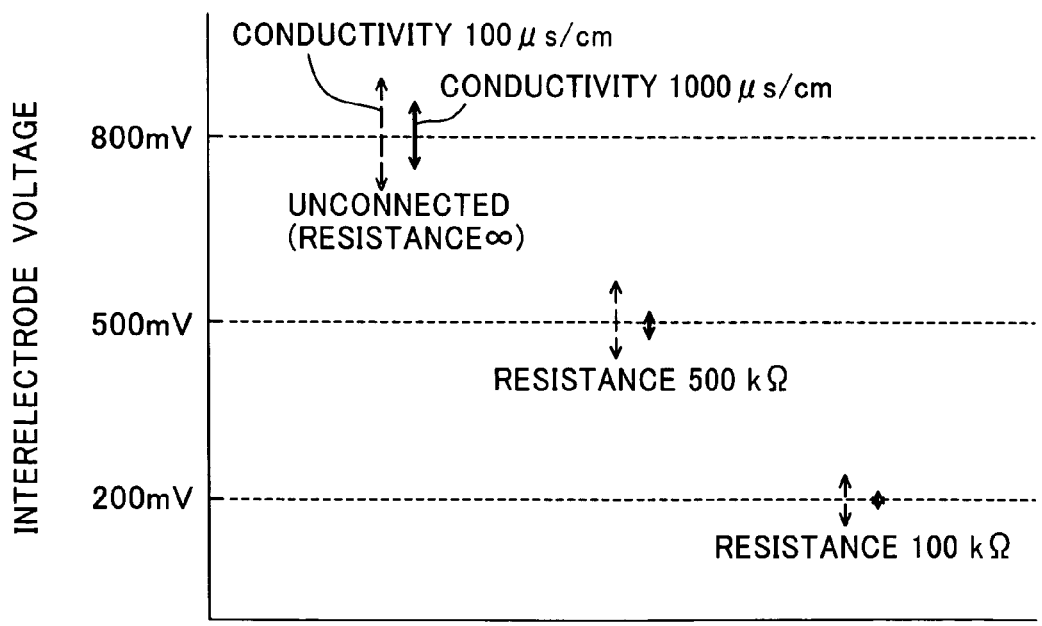
FIG. 29 is a graph illustrating influence by conductivity.

Hereinafter, the accuracy of the oxidation-reduction potential will be described briefly by use of the graph of FIG. 29. FIG. 29 shows the result of measurement with the vertical axis representing an interelectrode voltage and the horizontal axis representing the load constant (resistance value) of the impedance reducing circuit. As shown in this figure, a variation in interelectrode voltage varies according to the conductivity of a liquid. This variation changes according to the size of the load constant (resistance value) of the impedance reducing circuit in a connected state between the working electrode and the reference electrode. Hence, the oxidation-reduction potential becomes accurate.

The thus constituted oxidation-reduction potentiometer will be specifically described in Example 4 which will be described later.

Further, the oxidation-reduction potentiometer of the present invention may also be constituted such that the potentiometer further comprises water immersion measuring means for measuring that the above working electrode and the above reference electrode are immersed in a liquid prior to measurement of oxidation-reduction potential by the above oxidation-reduction potential measuring means, and the above reducing circuit switching means keeps the above impedance reducing circuit switched to an unconnected state during the measurement by the water immersion measuring means.

The thus constituted oxidation-reduction potentiometer can measure that the working electrode and the reference electrode are immersed in a liquid by the water immersion measuring means prior to measurement of oxidation-reduction potential by the above oxidation-reduction potential measuring means and have the above impedance reducing circuit switched to an unconnected state while measuring that the electrodes are immersed in the liquid. Thus, since the impedance reducing circuit is in an unconnected state while the working electrode and the reference electrode are immersed in a liquid prior to measurement of oxidation-reduction potential, a current does not pass between the electrodes, and the electrodes do not cause a chemical reaction. Hence, the oxidation-reduction potentiometer of the present invention has an advantage of extending the useful lives of the electrodes.

Figure 30:
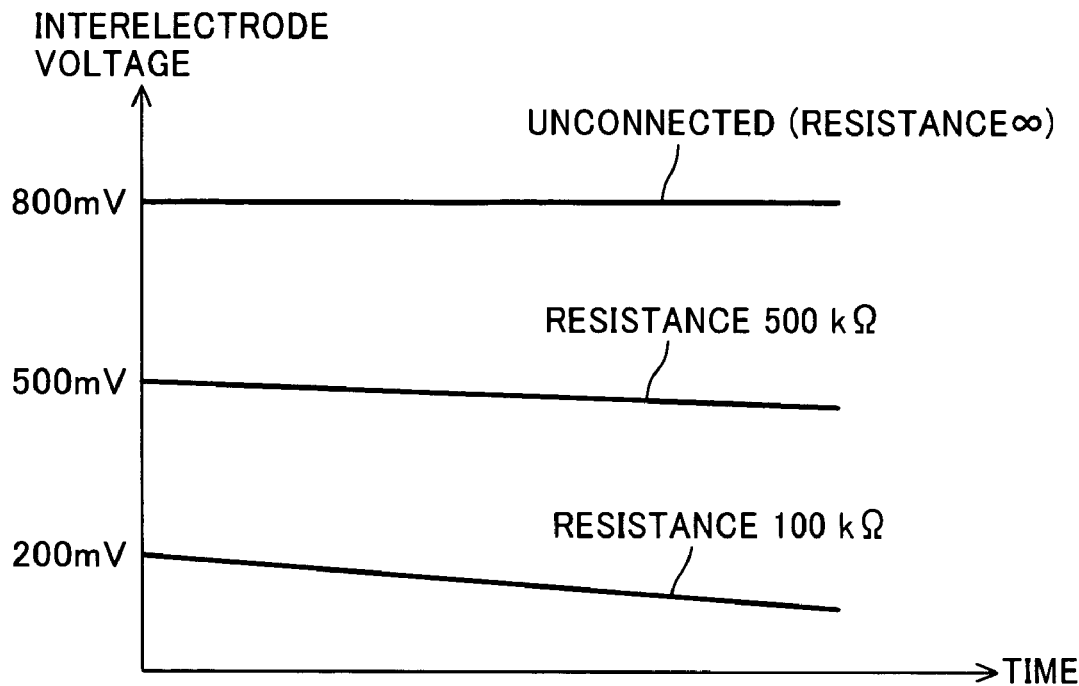
FIG. 30 is a graph illustrating influence by water immersion.

Hereinafter, the extension of the useful lives of the electrodes will be described briefly by use of the graph of FIG. 30. FIG. 30 shows the result of measurement with the vertical axis representing an interelectrode voltage and the horizontal axis representing water immersion elapsed time. As shown in this figure, when the impedance reducing circuit is in a connected state between the working electrode and the reference electrode, deterioration of the electrodes by the reaction occurs according to water immersion elapsed time, and the interelectrode voltage changes. Hence, the useful lives of the electrodes are extended by keeping the impedance reducing circuit in an unconnected state prior to measurement of oxidation-reduction potential.

The thus constituted oxidation-reduction potentiometer will be specifically described in Example 5 which will be described later.

Further, the oxidation-reduction potentiometer of the present invention may also be constituted such that the above working electrode comprises a plurality of working electrodes having different areas, the potentiometer further comprises working electrode switching means for switching connection to the interelectrode voltage measuring means to a working electrode out of the working electrodes having different areas, the above impedance reducing circuit reduces an impedance occurring between each of the working electrodes having different areas and the above reference electrode, the above reducing circuit switching means switches the above impedance reducing circuit to an unconnected state and a connected state between each of the working electrodes having different areas and the above reference electrode, the above interelectrode voltage measuring means measures an interelectrode voltage which is a difference between a potential indicating the degree of oxidation-reduction reaction and generated from each of the working electrodes having different areas and a reference potential generated from the above reference electrode when the impedance reducing circuit has been switched to the unconnected state and the connected state by the reducing circuit switching means, the above comparison coefficient computing section computes a comparison coefficient based on the interelectrode voltage in the unconnected state and the interelectrode voltage in the connected state which have been measured by the interelectrode voltage measuring means, the above comparison coefficient storing section stores the comparison coefficients computed by the comparison coefficient computing section, and the above oxidation-reduction potential computing section computes an oxidation-reduction potential based on the interelectrode voltage in the connected state which has been measured by the interelectrode voltage measuring means when the impedance reducing circuit has been switched to the connected state by the reducing circuit switching means and a corresponding comparison coefficient out of the comparison coefficients stored in the comparison coefficient storing section, the computation of the oxidation-reduction potential being performed for each of the working electrodes having different areas in the order of area from smallest to largest.

The thus constituted oxidation-reduction potentiometer immerses each of the working electrodes and the reference electrode in a reference liquid, measures an interelectrode voltage when the impedance reducing circuit is in an unconnected state between each of the working electrodes and the reference electrode and an interelectrode voltage when the impedance reducing circuit is in a connected state between the working electrode and the reference electrode by the interelectrode voltage measuring means, computes comparison coefficients based on these measured interelectrode voltages by the comparison coefficient computing section, stores the comparison coefficients in the comparison coefficient storing section, immerses each of the working electrodes and the reference electrode in a test liquid, measures an interelectrode voltage when the impedance reducing circuit is in a connected state between the working electrode having the smallest area and the reference electrode by the interelectrode voltage measuring means (this measurement is also made on the other working electrodes as well in the order of area from next smallest to largest), and can compute an oxidation-reduction potential by the oxidation-reduction potential computing section based on the measured interelectrode voltage in the connected state and the comparison coefficient stored in the comparison coefficient storing section. According to this, a measurement starts from small working electrodes which exhibit a higher reaction rate than working electrodes having large areas. Hence, the oxidation-reduction potentiometer of the present invention has an advantage of further reducing measuring time.

Figure 31:
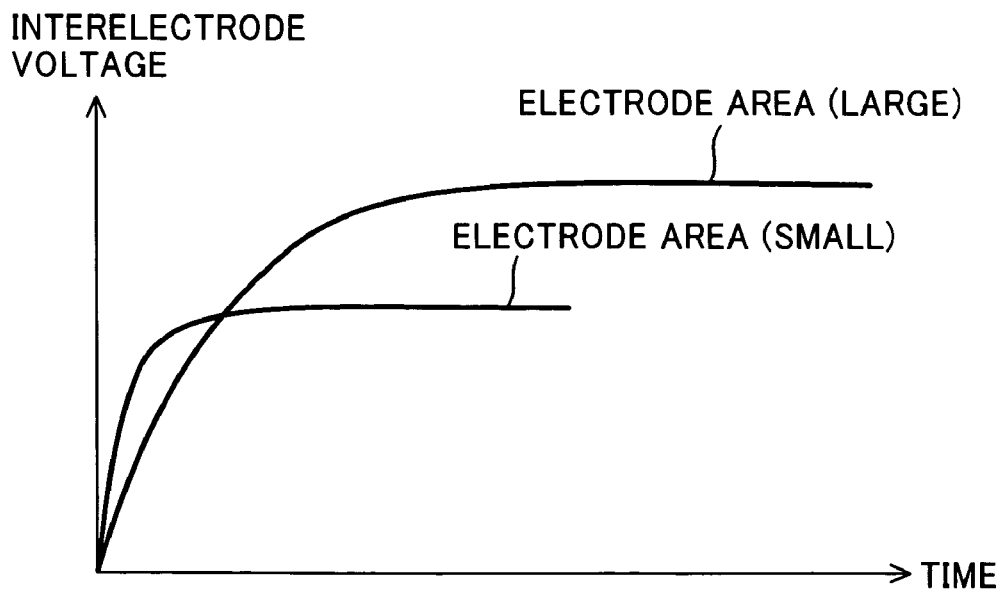
FIG. 31 is a graph illustrating influence by an electrode area.

Hereinafter, the reduction in measuring time will be described briefly by use of the graph of FIG. 31. FIG. 31 shows the result of measurement with the vertical axis representing an interelectrode voltage and the horizontal axis representing reaction time. As shown in this figure, an interelectrode voltage with an electrode having a small area becomes nearly constant in a shorter reaction time than an interelectrode voltage with an electrode having a large area. Thus, measuring time is reduced by making some measurements with electrodes having small areas.

The thus constituted oxidation-reduction potentiometer will be specifically described in Examples 6 and 7 which will be described later.

Further, the oxidation-reduction potentiometer of the present invention may also be constituted such that the above impedance reducing circuit reduces an impedance occurring between the above working electrode and the above reference electrode in multiple levels, the above reducing circuit switching means switches the above impedance reducing circuit to a connected state in multiple levels, the above interelectrode voltage measuring means measures an interelectrode voltage of each level when the impedance reducing circuit has been switched to the connected state in multiple levels, the above comparison coefficient computing section computes a comparison coefficient of each level based on the interelectrode voltage of the corresponding level in the connected state which has been measured by the interelectrode voltage measuring means, the above comparison coefficient storing section stores the comparison coefficient of each level computed by the comparison coefficient computing section, and the above oxidation-reduction potential computing section computes an oxidation-reduction potential value based on an interelectrode voltage in a connected state which has been measured by the interelectrode voltage measuring means when the impedance reducing circuit has been switched to the connected state of a specific level by the reducing circuit switching means and a comparison coefficient of the corresponding level out of the comparison coefficients of multiple levels stored in the comparison coefficient storing section.

The thus constituted oxidation-reduction potentiometer immerses the working electrode and the reference electrode in a reference liquid, measures an interelectrode voltage of each level when the impedance reducing circuit which is reduced in multiple levels is in an unconnected state between the working electrode and the reference electrode and an interelectrode voltage of the level when the impedance reducing circuit is in a connected state between the working electrode and the reference electrode by the interelectrode voltage measuring means, computes a comparison coefficient of each level based on these measured interelectrode voltages of the corresponding level by the comparison coefficient computing section, stores the comparison coefficients in the comparison coefficient storing section, immerses the working electrode and the reference electrode in a test liquid, measures an interelectrode voltage of each level when the impedance reducing circuit which is reduced in multiple levels is in a connected state between the working electrode and the reference electrode by the interelectrode voltage measuring means, and can compute an oxidation-reduction potential based on the measured interelectrode voltage of each level in the connected state and a comparison coefficient of the corresponding level out of the comparison coefficients of multiple levels stored in the comparison coefficient storing section. According to this, the range of the concentration which influences the oxidation-reduction reaction expands stepwise according to stepwise reduction of the impedance reducing circuit. Hence, the oxidation-reduction potentiometer of the present invention has an advantage of wide measurement range.

Figure 28:
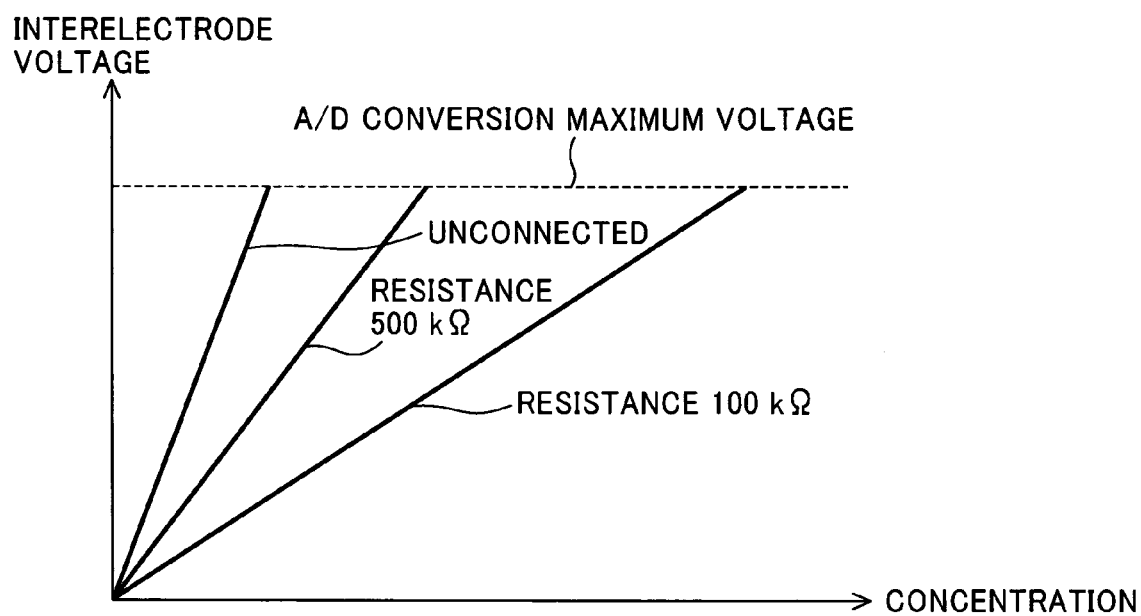
FIG. 28 is a graph illustrating influence on a measurement range.

Hereinafter, the expansion of the measurement range will be described briefly by use of the graph of FIG. 28. FIG. 28 shows the result of measurement with the vertical axis representing an interelectrode voltage and the horizontal axis representing the concentration of liquid which influences the oxidation-reduction reaction. As shown in this figure, the concentration of liquid which influences the oxidation-reduction reaction with respect to the A/D conversion maximum voltage expands according to the size of the load constant (resistance value) of the impedance reducing circuit which is connected between the working electrode and the reference electrode. Hence, the measurement range is expanded.

The thus constituted oxidation-reduction potentiometer will be specifically described in Examples 2 and 3 which will be described later.

Hereinafter, the above various embodiments will be further described with reference to the drawings.

EXAMPLE 1

Figure 2:
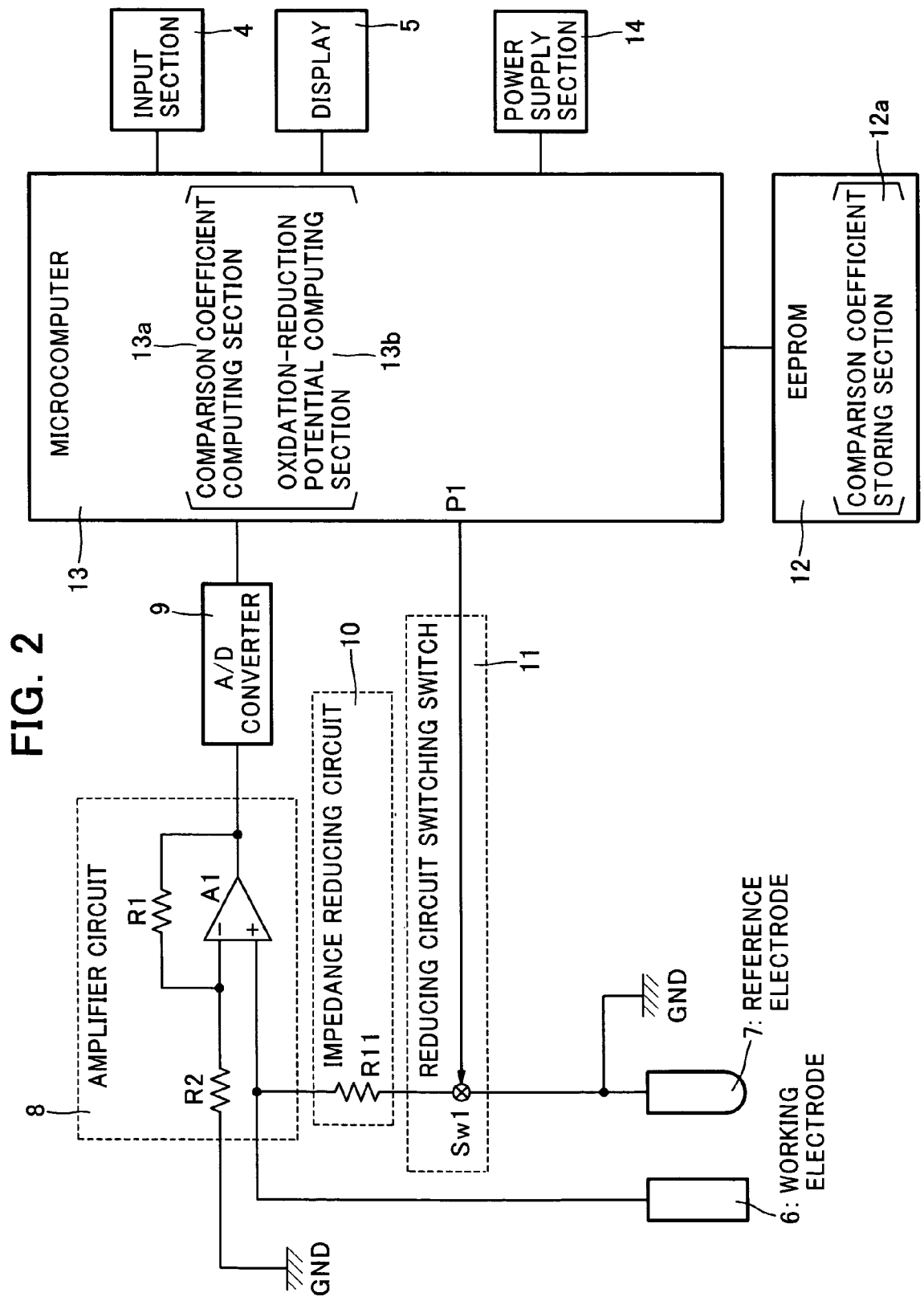
FIG. 2 is a block diagram illustrating the oxidation-reduction potentiometer. (Example 1)

First, the specific constitution of an oxidation-reduction potentiometer according to the present invention will be described by use of an external view shown in FIG. 1 and a block diagram shown in FIG. 2.

An oxidation-reduction potentiometer as Example 1 has, when viewed from the outside, a main unit 1 which has an input section 4 and a display 5 on the front side, a sensor 2 which serves as not only a working electrode 6 but also a reference electrode 7, and a cable 3 which connects the sensor 2 to the main unit 1. The oxidation-reduction potentiometer also has an electronic substrate and a power supply section 14 inside the main unit 1. The electronic substrate has an amplifier circuit 8, an A/D converter 9, an impedance reducing circuit 10, a reducing circuit switching switch 11, an EEPROM 12 and a microcomputer 13. These roughly constitute the oxidation-reduction potentiometer as a whole.

The input section 4 comprises an ON key 4a, a START key 4b, a MODE key 4c, a +key 4d and a −key 4e and is used for supplying electric power, staring a measurement, switching or the like. The ON key 4a is used to start supplying electric power from the power supply section 14 to components in the electrical system. The START key 4b is used to start a measurement. The MODE key 4c is used to switch between an adjustment mode and a measurement mode. The +key 4d and the −key 4e are used to select an item, a numerical value or the like displayed on the display 5.

The display 5 displays an input status, measurement results, various modes, remaining battery power and the like.

The sensor 2 is formed by forming an outer glass tube (shown transparent in FIG. 1) 2b on the outer side of an inner glass tube (shown transparent in FIG. 1) 2a in such a manner that the outer tube 2b covers the inner tube 2a with space therebetween, providing platinum (Pt) 2c from the outer side of the inner glass tube 2a to the outer side of the outer glass tube 2b, setting an internal electrode 2d which is silver (Ag) covered with silver chloride (AgCl) in the inner glass tube 2a, filling liquid or gelled sodium chloride (NaCl) or potassium chloride (KCl) in the inner glass tube 2a, providing a liquid junction 2e from the inside of the inner glass tube 2a to the outer sides of the inner glass tube 2a and the outer glass tube 2b, and connecting the platinum (Pt) 2c and the internal electrode 2d to the electronic substrate by use of conducting wires 2f and 2g, respectively.

The platinum (Pt) 2c portion corresponds to the working electrode 6. The inner glass tube 2a, the internal electrode 2d, sodium chloride (NaCl) or potassium chloride (KCl) and the liquid junction 2e correspond to the reference electrode 7.

The power supply section 14 supplies electric power to the components in the electrical system.

The amplifier circuit 8 amplifies an interelectrode voltage (analog signal) which is a difference between a measured potential generated from the working electrode 6 and indicating the degree of oxidation-reduction reaction and a measured reference potential generated from the reference electrode 7. The A/D converter 9 converts the amplified interelectrode voltage into a digital signal.

The impedance reducing circuit 10 comprises a resistance (R11) that is disposed between the working electrode 6 and the reference electrode 7 such that it can be switched between an unconnected state and a connected state by the reducing circuit switching switch 11. The circuit 10 reduces an impedance occurring between the working electrode 6 and the reference electrode 7 when the electrodes are immersed in a liquid.

The reducing circuit switching switch 11 switches the impedance reducing circuit 10 between an unconnected state and a connected state based on a control signal from the microcomputer 13.

The EEPROM 12 has a comparison coefficient storing section 12a and stores various data. The comparison coefficient storing section 12a stores a comparison coefficient computed by a comparison coefficient computing section 13a which will be described later.

The microcomputer 13 has the comparison coefficient computing section 13a and an oxidation-reduction potential computing section 13b. The microcomputer 13 computes various data and controls switching of the reducing circuit switching switch 11 and determinations of various data.

The comparison coefficient computing section 13a computes a comparison coefficient based on an interelectrode voltage (reference liquid voltage) from the A/D converter 9 when the impedance reducing circuit 10 is in an unconnected state and an interelectrode voltage (reference liquid voltage) from the A/D converter 9 when the impedance reducing circuit 10 is in a connected state. More specifically, the comparison coefficient computing section 13a computes a comparison coefficient k1 by dividing an interelectrode voltage Vr0 from the A/D converter 9 when the impedance reducing circuit 10 is in an unconnected state by an interelectrode voltage Vr1 from the A/D converter 9 when the impedance reducing circuit 10 is in a connected state, as shown in the following computing equation (1).

$$k1=Vr0/Vr1 \tag{1}$$

The oxidation-reduction potential computing section 13b computes an oxidation-reduction potential based on an interelectrode voltage from the A/D converter 9 when the impedance reducing circuit 10 is in a connected state and the comparison coefficient stored in the comparison coefficient storing section 12a, when the impedance reducing circuit 10 has been switched to the connected state based on a control signal from the microcomputer 13. More specifically, the oxidation-reduction potential computing section 13b computes an interelectrode voltage (test liquid voltage) from the A/D converter 9 when the impedance reducing circuit 10 is in an unconnected state, i.e., an oxidation-reduction potential Vs0, by multiplying an interelectrode voltage Vs1 from the A/D converter 9 when the impedance reducing circuit 10 is in a connected state by the comparison coefficient k1 stored in the comparison coefficient storing section 12a, as shown in the following computing equation (2).

$$Vs0=k1 \times Vs1 \tag{2}$$

The reducing circuit switching switch 11 and the microcomputer 13 constitute reducing circuit switching means. Further, the amplifier circuit 8, the A/D converter 9 and the microcomputer 13 constitute interelectrode voltage measuring means. Further, the reducing circuit switching means, the interelectrode voltage measuring means, the comparison coefficient computing section 13a, the comparison coefficient storing section 12a and the oxidation-reduction potential computing section 13b constitute oxidation-reduction potential measuring means.

Figure 3:
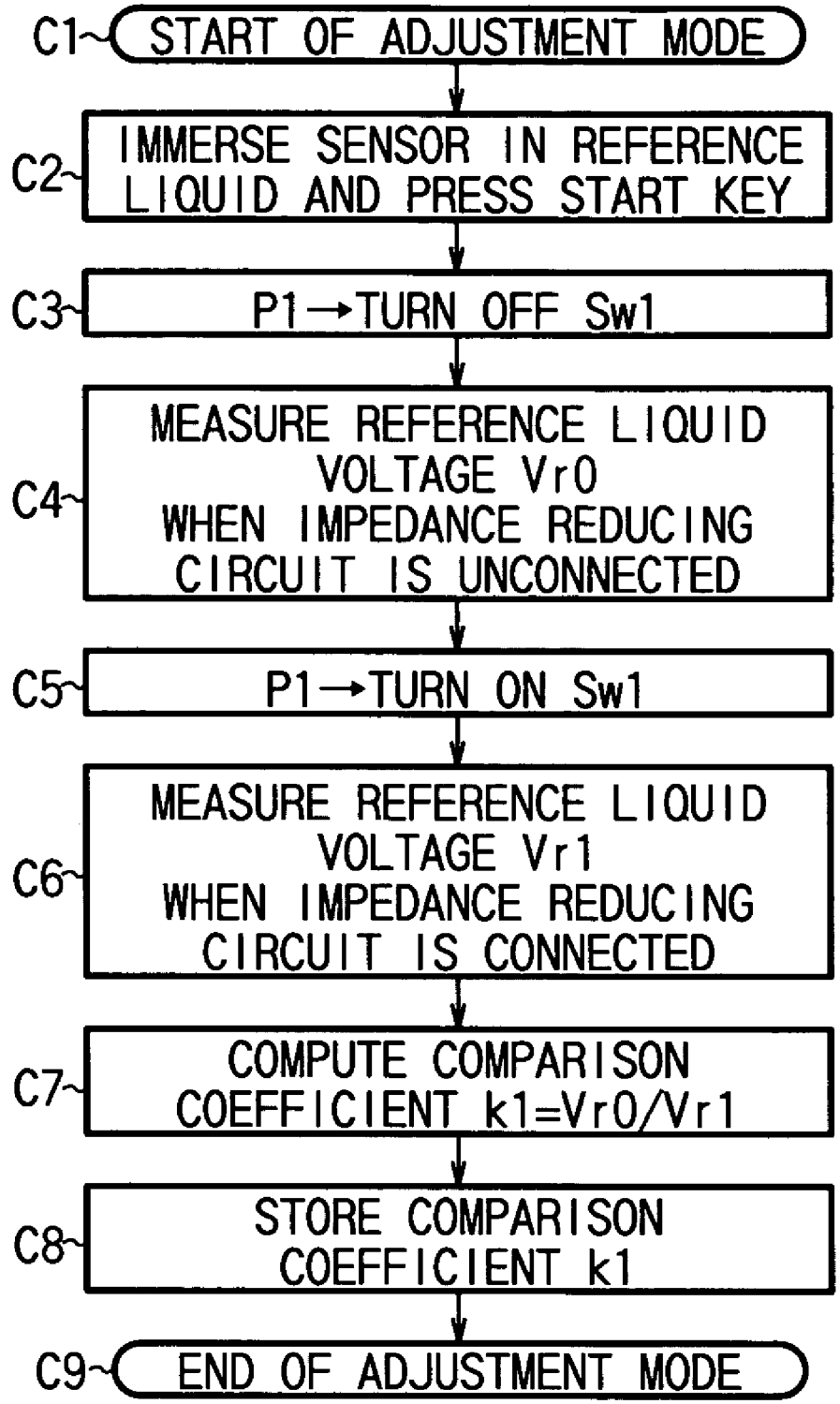
FIG. 3 is a flowchart in an adjustment mode of the oxidation-reduction potentiometer. (Example 1)

Next, specific operations of the oxidation-reduction potentiometer according to the present invention will be described by use of a flowchart in an adjustment mode shown in FIG. 3 and a flowchart in a normal mode shown in FIG. 4.

At the press of the ON key 4a, electric power is supplied from the power supply section 14 to the components in the electrical system, and the potentiometer of the present invention enters the normal mode to be described later in accordance with the flowchart shown in FIG. 4 (STEP G1). Then, when the MODE key 4c is pressed subsequently, the present potentiometer enters the adjustment mode which proceeds according to the flowchart shown in FIG. 3 (STEP C1).

Then, when the sensor 2 is immersed in a reference liquid and the START key 4b is pressed (STEP C2), the reducing circuit switching switch (Sw1) 11 is turned off based on an OFF control signal from the port P1 of the microcomputer 13. As a result, the impedance reducing circuit (R11) 10 is switched to an unconnected state (STEP C3).

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (reference liquid voltage) $Vr0$ when the impedance reducing circuit 10 is unconnected by the microcomputer 13 (STEP C4).

Then, the reducing circuit switching switch (Sw1) 11 is turned on based on an ON control signal from the port P1 of the microcomputer 13, whereby the impedance reducing circuit (R11) 10 is switched to a connected state (STEP C5).

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (reference liquid voltage) $Vr1$ when the impedance reducing circuit 10 is connected by the microcomputer 13 (STEP C6).

Then, in the comparison coefficient computing section 13a, a comparison coefficient $k1$ is computed by dividing the interelectrode voltage (reference liquid voltage) $Vr0$ when the impedance reducing circuit 10 is unconnected by the interelectrode voltage (reference liquid voltage) $Vr1$ when the impedance reducing circuit 10 is connected, as shown in the above computing equation (1) (STEP C7). After the computed comparison coefficient $k1$ is stored in the comparison coefficient storing section 12a (STEP C8), the adjustment mode is ended (STEP C9)

Next, specific operations of the oxidation-reduction potentiometer according to the present invention in the normal mode will be described in detail.

Figure 4:
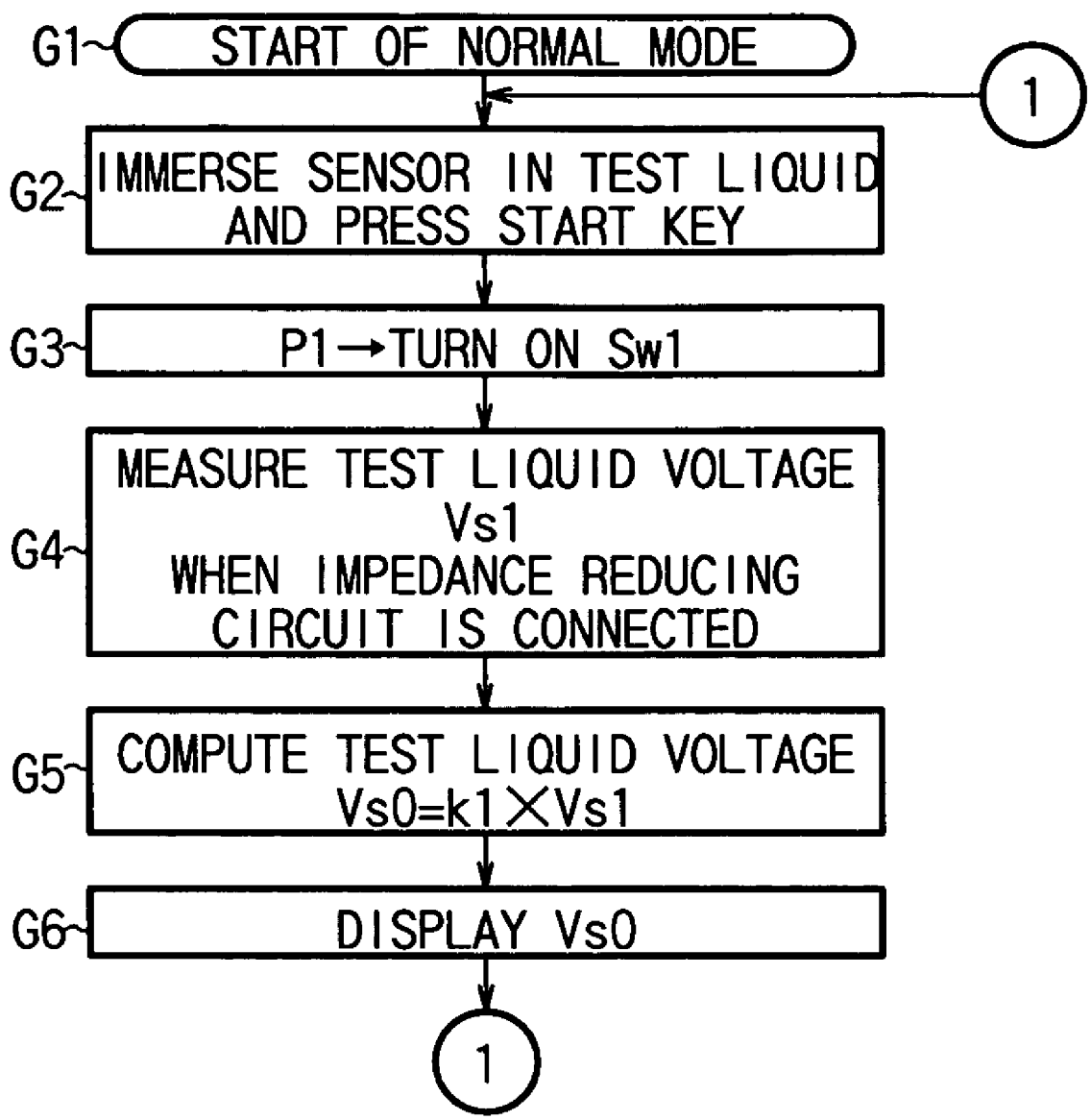
FIG. 4 is a flowchart in a normal mode of the oxidation-reduction potentiometer. (Example 1)

Immediately after the ON key 4a is pressed or after the adjustment mode is ended, the potentiometer of the present invention enters the normal mode which proceeds according to the flowchart shown in FIG. 4 (STEP G1).

Then, when the sensor 2 is immersed in a test liquid and the START key 4b is pressed (STEP G2), the reducing circuit switching switch (Sw1) 11 is turned on based on an ON control signal from the port P1 of the microcomputer 13, whereby the impedance reducing circuit (R11) 10 is switched to a connected state (STEP G3).

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (test liquid voltage) $Vs1$ when the impedance reducing circuit 10 is connected by the microcomputer 13 (STEP G4).

Then, in the oxidation-reduction potential computing section 13b, an interelectrode voltage (test liquid voltage) when the impedance reducing circuit 10 is unconnected, i.e., an oxidation-reduction potential $Vs0$, is computed by multiplying the interelectrode voltage (test liquid voltage) $Vs1$ when the impedance reducing circuit 10 is connected by the comparison coefficient $k1$ which is stored in the comparison coefficient storing section 12a, as shown in the above computing equation (2) (STEP G5). The result is displayed on the display 5 (STEP G6).

Subsequently, the present potentiometer can return to STEP G2 and repeat the processes.

EXAMPLE 2

Figure 5:
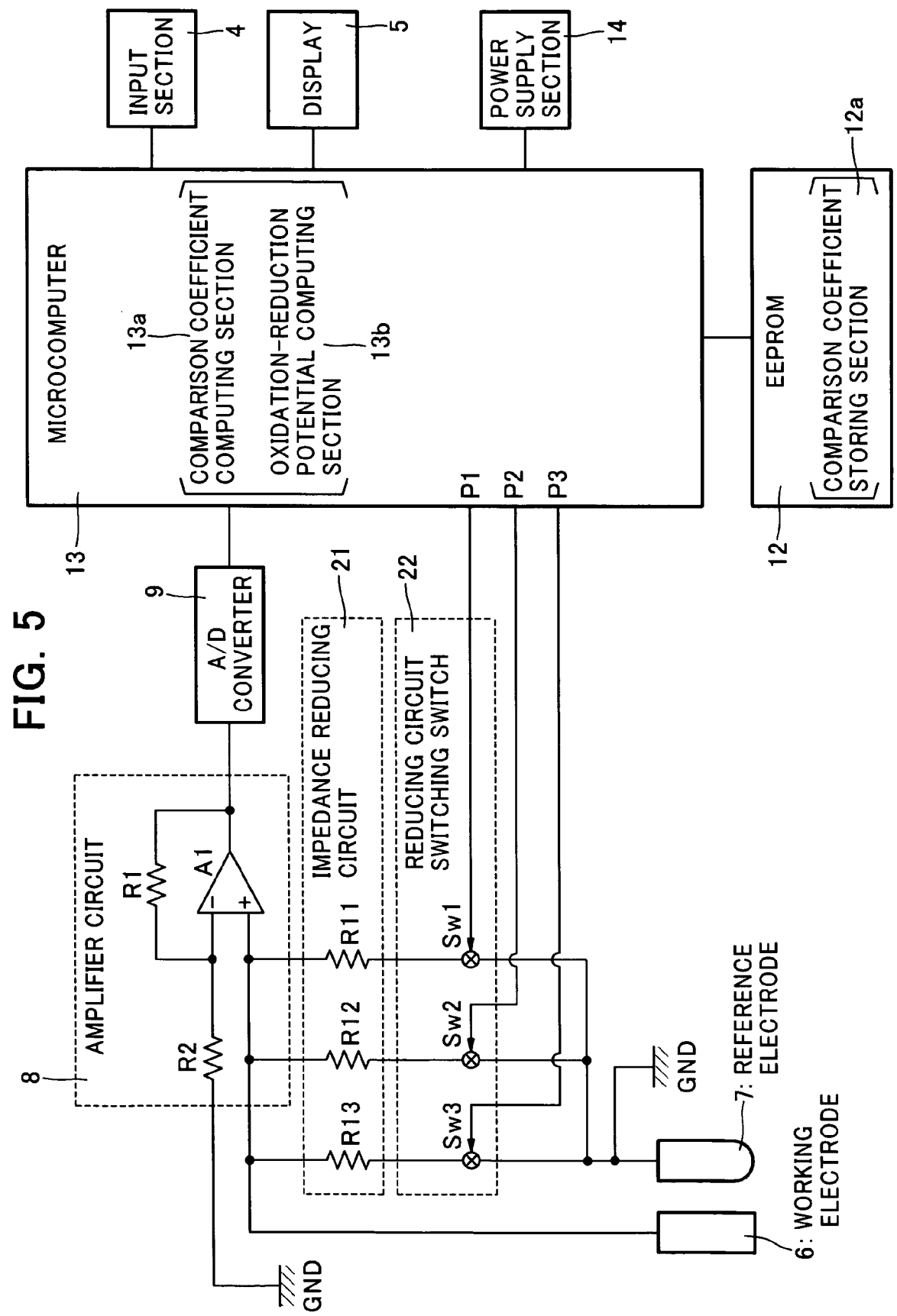
FIG. 5 is a block diagram illustrating the oxidation-reduction potentiometer. (Example 2)

First, the specific constitution of an oxidation-reduction potentiometer according to the present invention will be described by use of an external view shown in FIG. 1 and a block diagram shown in FIG. 5.

An oxidation-reduction potentiometer as Example 2 as a whole has a constitution which is nearly the same as that of the oxidation-reduction potentiometer described as Example 1. Hereinafter, only components different from those in the oxidation-reduction potentiometer described as Example 1 will be described in detail.

An impedance reducing circuit 21 comprises a plurality of resistances Sw1, Sw2 and Sw3 having different resistance values which are disposed between a working electrode 6 and a reference electrode 7 such that it can be switched between an unconnected state and a connected state by a reducing circuit switching switch 22. The circuit 21 reduces an impedance occurring between the working electrode 6 and the reference electrode 7 when the electrodes are immersed in a liquid in multiple levels.

The reducing circuit switching switch 22 switches the impedance reducing circuit 21 between an unconnected state and a connected state in multiple levels based on a control signal from a microcomputer 13.

A comparison coefficient computing section 13a computes a comparison coefficient based on an interelectrode voltage (reference liquid voltage) from an A/D converter 9 when all resistances in the impedance reducing circuit 21 are in an unconnected state and an interelectrode voltage (reference liquid voltage) from the A/D converter 9 when one of the resistances in the impedance reducing circuit 21 is in a connected state. More specifically, the comparison coefficient computing section 13a computes a comparison coefficient $kN$ (wherein N represents a level number) of a specific level by dividing an interelectrode voltage $Vr0$ from the A/D converter 9 when all, resistances in the impedance reducing circuit 21 are in an unconnected state by an interelectrode voltage $VrN$ (wherein N represents a level number) from the A/D converter 9 when a resistance of the specific level among the resistances in the impedance reducing circuit 21 is in a connected state, as shown in the following computing equation (3). This computation is performed for the resistances of all levels.

$$kN = Vr0/VrN \qquad (3)$$

An oxidation-reduction potential computing section 13b computes an oxidation-reduction potential based on an interelectrode voltage from the A/D converter 9 when a resistance of a specific level among the resistances in the impedance reducing circuit 21 is in a connected state and a comparison coefficient of the specific level which is stored in a comparison coefficient storing section 12a, when the resistance of the specific level in the impedance reducing circuit 21 has been switched to the connected state based on a control signal from the microcomputer. More specifically, the oxidation-reduction potential computing section 13b computes an interelectrode voltage (test liquid voltage) from the A/D converter 9 when the impedance reducing circuit 21 is in an unconnected state, i.e., an oxidation-reduction potential Vs0, by multiplying an interelectrode voltage VsN from the A/D converter 9 when a resistance of a specific level in the impedance reducing circuit 21 is in a connected state by a comparison coefficient kN of the specific level stored in the comparison coefficient storing section 12a, as shown in the following computing equation (4).

$$Vs0 = kN \times VsN \tag{4}$$

Figure 6:
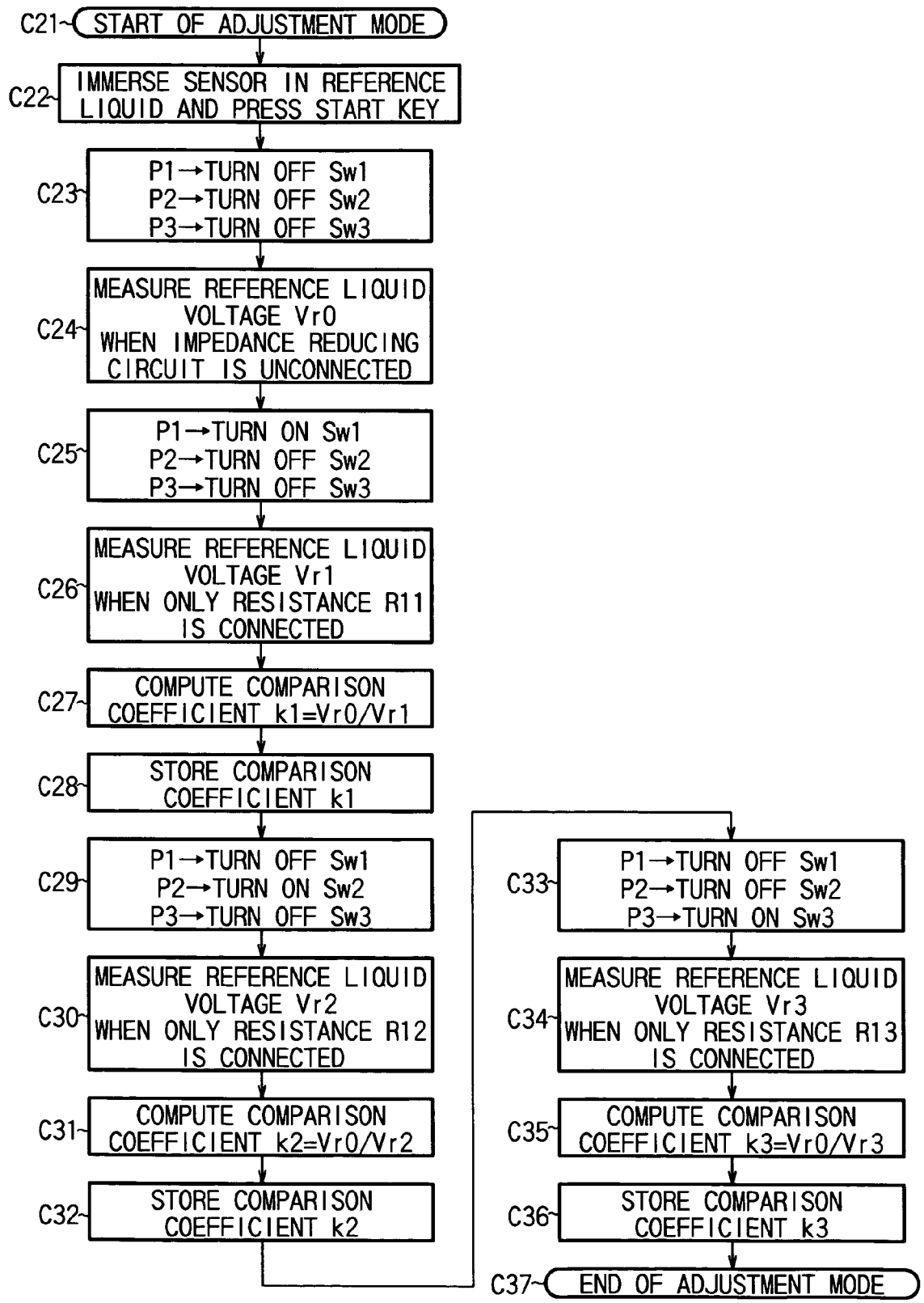
FIG. 6 is a flowchart in an adjustment mode of the oxidation-reduction potentiometer. (Example 2)

Next, specific operations of the oxidation-reduction potentiometer according to the present invention will be described by use of a flowchart in an adjustment mode shown in FIG. 6 and a flowchart in a normal mode shown in FIG. 7.

First, specific operations in the adjustment mode will be described in detail.

At the press of an ON key 4a, electric power is supplied from a power supply section 14 to the components in the electrical system, and the potentiometer of the present invention enters the normal mode to be described later in accordance with the flowchart shown in FIG. 7 (STEP G21). Then, when a MODE key 4c is pressed subsequently, the present potentiometer enters the adjustment mode which proceeds according to the flowchart shown in FIG. 6 (STEP C21).

Then, when a sensor 2 is immersed in a reference liquid and a START key 4b is pressed (STEP C22), the reducing circuit switching switch (Sw1, Sw2 and Sw3) 22 is turned off based on OFF control signals from the ports P1, P2 and P3 of the microcomputer 13. As a result, the impedance reducing circuit (R11, R12 and R13) 21 is switched to an unconnected state (STEP C23).

Then, an interelectrode voltage (analog signal) generated between the working electrode 6 and the reference electrode 7 at that time is amplified by an amplifier circuit 8, converted into a digital signal by the A/D converter 9, and computed as an interelectrode voltage (reference liquid voltage) Vr0 when the impedance reducing circuit 21 is unconnected by the microcomputer 13 (STEP C24).

Then, Sw1 in the reducing circuit switching switch 22 is turned on based on an ON control signal from the port P1 of the microcomputer 13, whereby a first-level resistance R11 in the impedance reducing circuit 21 is switched to a connected state (STEP C25).

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (reference liquid voltage) Vr1 when the first-level resistance R11 is connected by the microcomputer 13 (STEP C26).

Then, in the comparison coefficient computing section 13a, a first-level comparison coefficient k1 is computed by dividing the interelectrode voltage (reference liquid voltage) Vr0 when all resistances are unconnected by the interelectrode voltage (reference liquid voltage) Vr1 when the first-level resistance R11 is connected, as shown in the above computing equation (3) (STEP C27). The computed first-level comparison coefficient k1 is stored in the comparison coefficient storing section 12a (STEP C28).

Then, the Sw1 in the reducing circuit switching switch 22 is turned off based on an OFF control signal from the port P1 of the microcomputer 13, and Sw2 in the reducing circuit switching switch 22 is turned on based on an ON control signal from the port P2 of the microcomputer 13. As a result, a second-level resistance R12 in the impedance reducing circuit 21 is switched to a connected state (STEP C29).

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (reference liquid voltage) Vr2 when the second-level resistance R12 is connected by the microcomputer (STEP C30).

Then, in the comparison coefficient computing section 13a, a second-level comparison coefficient k2 is computed by dividing the interelectrode voltage (reference liquid voltage) Vr0 when all resistances are unconnected by the interelectrode voltage (reference liquid voltage) Vr2 when the second-level resistance R12 is connected, as shown in the above computing equation (3) (STEP C31). The computed second-level comparison coefficient k2 is stored in the comparison coefficient storing section (STEP C32).

Then, the Sw2 in the reducing circuit switching switch 22 is turned off based on an OFF control signal from the port P2 of the microcomputer 13, and Sw3 in the reducing circuit switching switch 22 is turned on based on an ON control signal from the port P3 of the microcomputer 13. As a result, a third-level resistance R13 in the impedance reducing circuit 21 is switched to a connected state (STEP C33).

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (reference liquid voltage) Vr3 when the third-level resistance R13 is connected by the microcomputer 13 (STEP C34).

Then, in the comparison coefficient computing section 13a, a third-level comparison coefficient k3 is computed by dividing the interelectrode voltage (reference liquid voltage) Vr0 when all resistances are unconnected by the interelectrode voltage (reference liquid voltage) Vr3 when the third-level resistance R13 is connected, as shown in the above computing equation (3) (STEP C35). The computed third-level comparison coefficient k3 is stored in the comparison coefficient storing section 12a (STEP C36), whereby the adjustment mode is ended (STEP C37)

Next, specific operations of the oxidation-reduction potentiometer according to the present invention in the normal mode will be described in detail.

Figure 7:
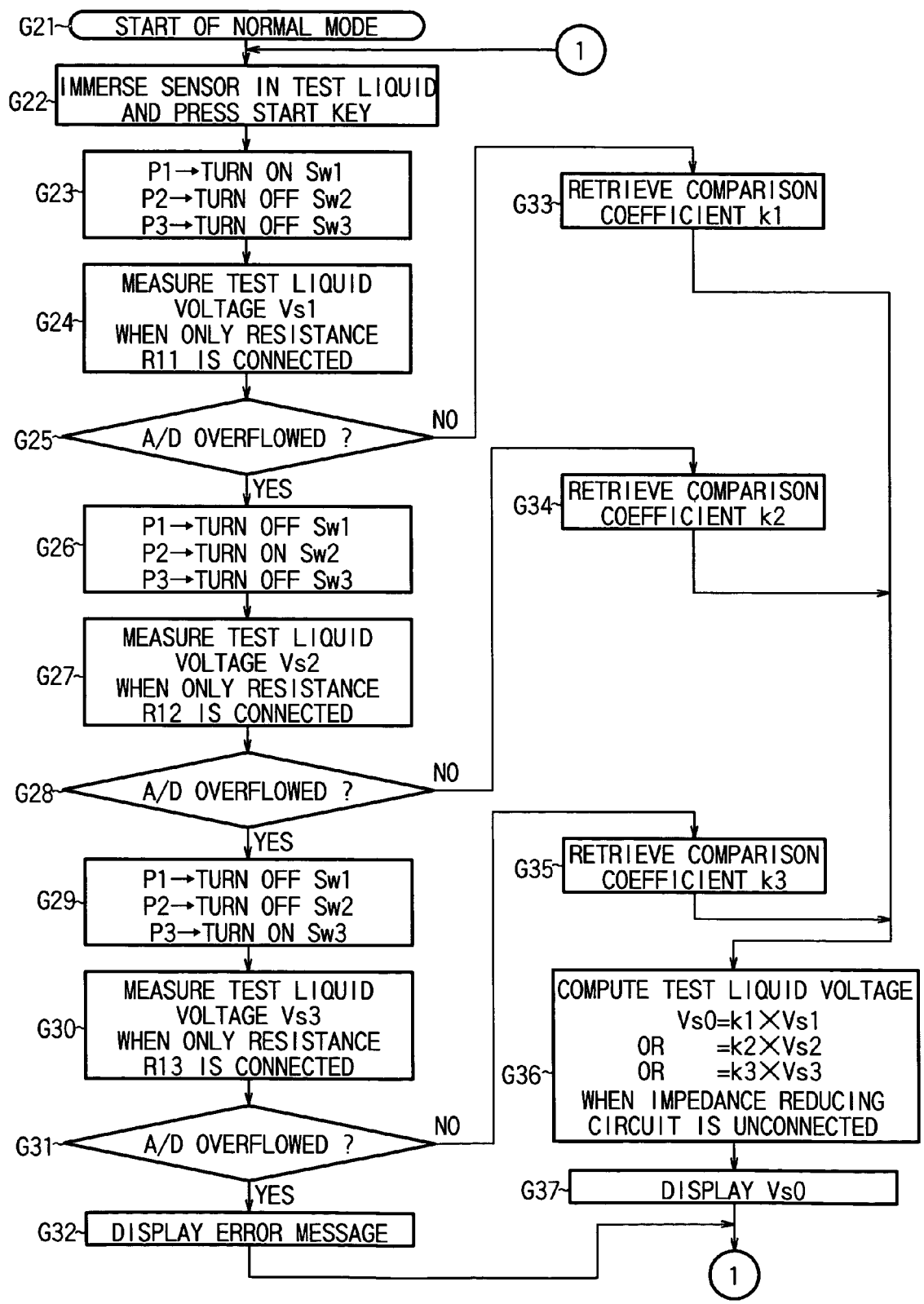
FIG. 7 is a flowchart in a normal mode of the oxidation-reduction potentiometer. (Example 2)

Immediately after the ON key 4a is pressed or after the adjustment mode is ended, the potentiometer of the present invention enters the normal mode which proceeds according to the flowchart shown in FIG. 7 (STEP G21).

Then, when the sensor 2 is immersed in a test liquid and the START key 4b is pressed (STEP G22), the Sw1 in the reducing circuit switching switch 22 is turned on based on an ON control signal from the port P1 of the microcomputer 13, whereby the first-level resistance R11 in the impedance reducing circuit 21 is switched to a connected state (STEP G23)

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (test liquid voltage) Vs1 when the first-level resistance R11 is connected by the microcomputer 13 (STEP G24).

Then, the microcomputer 13 determines whether the computed interelectrode voltage Vs1 exceeds the amplification tolerance of the amplifier circuit 8 (STEP G25).

Then, when the microcomputer 13 has determined that the interelectrode voltage Vs1 does not exceed the amplification tolerance (NO in STEP G25), the microcomputer 13 retrieves the first-level comparison coefficient k1 from the comparison coefficient storing section 12a (STEP G33).

Meanwhile, when the microcomputer 13 has determined that the interelectrode voltage Vs1 exceeds the amplification tolerance (YES in STEP G25), the Sw1 in the reducing circuit switching switch 22 is turned off based on an OFF control signal from the port P1 of the microcomputer 13, and the Sw2 in the reducing circuit switching switch 22 is turned on based on an ON control signal from the port P2 of the microcomputer 13. As a result, the second-level resistance R12 in the impedance reducing circuit 21 is switched to a connected state (STEP G26) Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (test liquid voltage) Vs2 when the second-level resistance R12 is connected by the microcomputer 13 (STEP G27).

Then, the microcomputer 13 determines whether the computed interelectrode voltage Vs2 exceeds the amplification tolerance of the amplifier circuit 8 (STEP G28).

Then, when the microcomputer 13 has determined that the interelectrode voltage Vs2 does not exceed the amplification tolerance (NO in STEP G28), the microcomputer 13 retrieves the second-level comparison coefficient k2 from the comparison coefficient storing section 12a (STEP G34).

Meanwhile, when the microcomputer 13 has determined that the interelectrode voltage Vs2 exceeds the amplification tolerance (YES in STEP G28), the Sw2 in the reducing circuit switching switch 22 is turned off based on an OFF control signal from the port P2 of the microcomputer 13, and the Sw3 in the reducing circuit switching switch 22 is turned on based on an ON control signal from the port P3 of the microcomputer 13. As a result, the third-level resistance R13 in the impedance reducing circuit is switched to a connected state (STEP G29).

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (test liquid voltage) Vs3 when the third-level resistance R13 is connected by the microcomputer 13 (STEP G30).

Then, the microcomputer 13 determines whether the computed interelectrode voltage Vs3 exceeds the amplification tolerance of the amplifier circuit 8 (STEP G31).

Then, when the microcomputer 13 has determined that the interelectrode voltage Vs3 does not exceed the amplification tolerance (NO in STEP G31), the microcomputer 13 retrieves the third-level comparison coefficient k3 from the comparison coefficient storing section 12a (STEP G35).

Meanwhile, when the microcomputer 13 has determined that the interelectrode voltage Vs3 exceeds the amplification tolerance (YES in STEP G31), the microcomputer 13 displays an error message which indicates that the interelectrode voltage is out of the amplification tolerance on the display 5 (STEP G32).

Then, in the oxidation-reduction potential computing section 13b, an interelectrode voltage (test liquid voltage) when the impedance reducing circuit 21 is unconnected, i.e., an oxidation-reduction potential Vs0, is computed by multiplying the interelectrode voltage (test liquid voltage) VsN when a resistance of a specific level is connected by the comparison coefficient kN of the specific level which is stored in the comparison coefficient storing section 12a, as shown in the above computing equation (4) (STEP G36). The result is displayed on the display 5 (STEP G37).

Subsequently, the present potentiometer can return to STEP G22 and repeat the processes.

EXAMPLE 3

Figure 8:
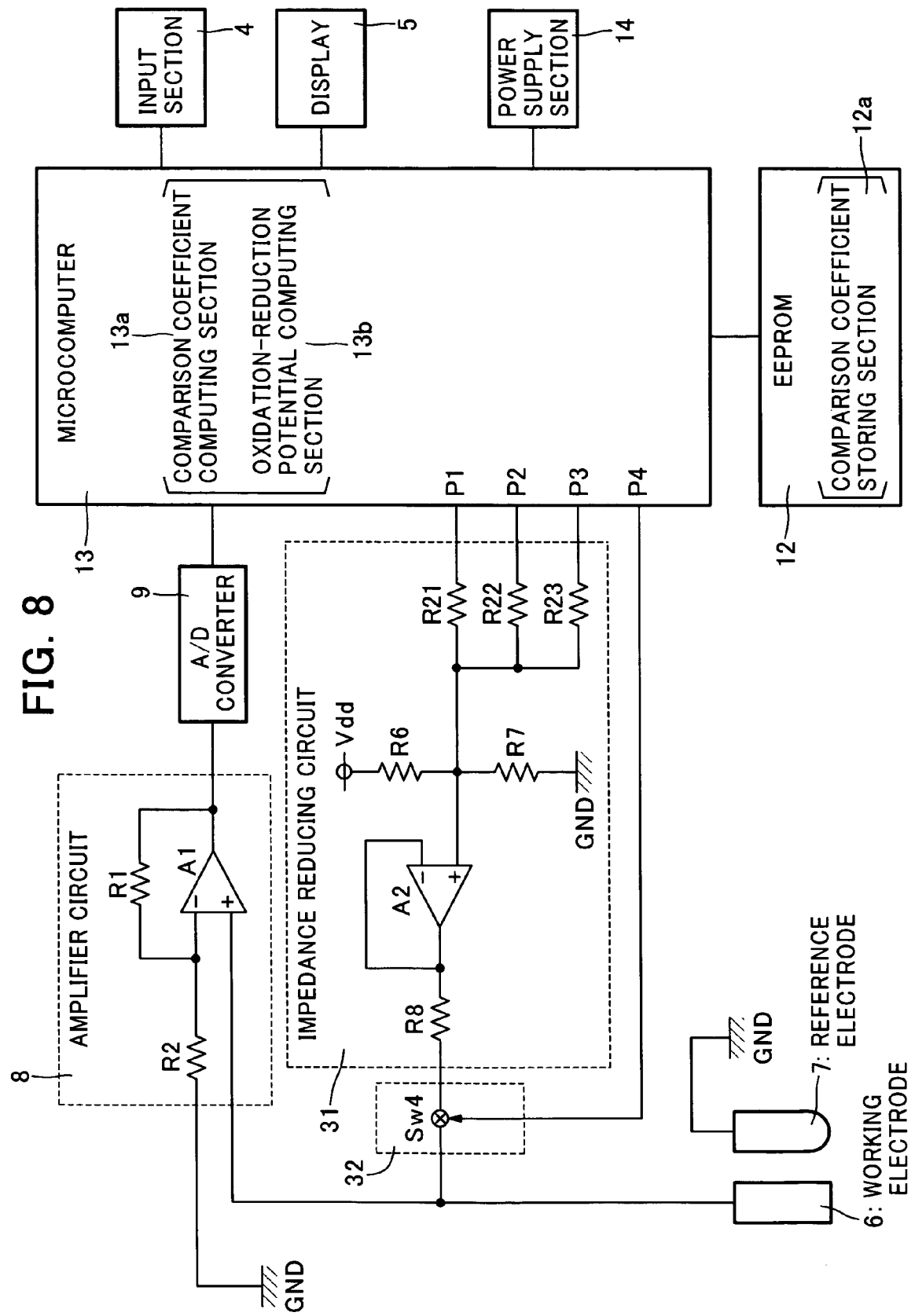
FIG. 8 is a block diagram illustrating the oxidation-reduction potentiometer. (Example 3)

First, the specific constitution of an oxidation-reduction potentiometer according to the present invention will be described by use of an external view shown in FIG. 1 and a block diagram shown in FIG. 8.

An oxidation-reduction potentiometer as Example 3 as a whole has a constitution which is nearly the same as that of the oxidation-reduction potentiometer described as Example 2. Hereinafter, only components different from those in the oxidation-reduction potentiometer described as Example 2 will be described in detail.

An impedance reducing circuit 31 comprises voltage generating circuits R6 and R7 which generate a voltage, a voltage follower A2 which is connected to the circuits R6 and R7, and an output resistance R8 which is connected between the voltage follower A2 and a working electrode 6. The impedance reducing circuit 31 is disposed between the working electrode 6 and a reference electrode 7 such that it can be switched between an unconnected state and a connected state by a reducing circuit switching switch (Sw4) 32. The impedance reducing circuit 31 reduces an impedance occurring between the working electrode 6 and the reference electrode 7 when the electrodes are immersed in a liquid in multiple levels.

The reducing circuit switching switch 32 switches the impedance reducing circuit 31 between an unconnected state and a connected state based on a control signal from a microcomputer 13.

Figure 9:
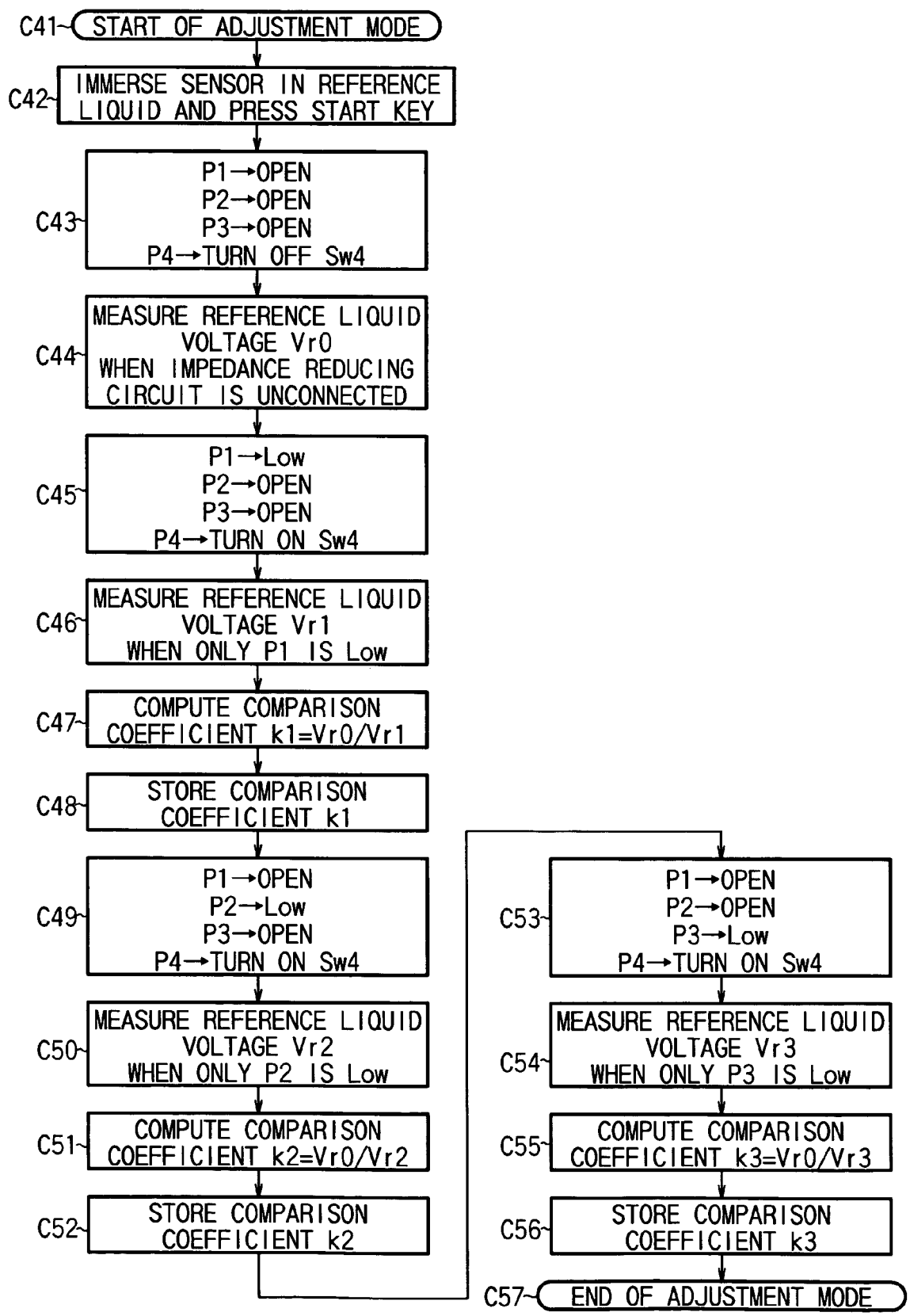
FIG. 9 is a flowchart in an adjustment mode of the oxidation-reduction potentiometer. (Example 3)

Next, specific operations of the oxidation-reduction potentiometer according to the present invention will be described by use of a flowchart in an adjustment mode shown in FIG. 9 and a flowchart in a normal mode shown in FIG. 10.

First, specific operations in the adjustment mode will be described in detail.

At the press of an ON key 4a, electric power is supplied from a power supply section 14 to the components in the electrical system, and the potentiometer of the present invention enters the normal mode to be described later in accordance with the flowchart shown in FIG. 10 (STEP G41). Then, when a MODE key 4c is pressed subsequently, the present potentiometer enters the adjustment mode which proceeds according to the flowchart shown in FIG. 9 (STEP C41).

Then, when a sensor 2 is immersed in a reference liquid and a START key 4b is pressed (STEP C42), all of the ports P1, P2 and P3 of the microcomputer 13 are opened, and the reducing circuit switching switch (Sw4) 32 is turned off based on an OFF control signal from the port P4 of the microcomputer 13. As a result, the impedance reducing circuit 31 is switched to an unconnected state (STEP C43).

Then, an interelectrode voltage (analog signal) generated between the working electrode 6 and the reference electrode 7 at that time is amplified by an amplifier circuit 8, converted into a digital signal by an A/D converter 9, and computed as an interelectrode voltage (reference liquid voltage) Vr0 when the impedance reducing circuit 31 is unconnected by the microcomputer 13 (STEP C44).

Then, the port P1 of the microcomputer 13 becomes a LOW level control signal, and the reducing circuit switching switch (Sw4) 22 is turned on based on an ON control signal from the port P4 of the microcomputer 13. As a result, the impedance reducing circuit 31 is switched to a connected state on a first output level (STEP C45).

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (reference liquid voltage) Vr1 when the impedance reducing circuit 31 is connected on the first output level by the microcomputer 13 (STEP C46).

Then, in a comparison coefficient computing section 13a, a comparison coefficient k1 on the first output level is computed by dividing the interelectrode voltage (reference liquid voltage) Vr0 when the impedance reducing circuit 31 is unconnected by the interelectrode voltage (reference liquid voltage) Vr1 when the impedance reducing circuit 31 is connected on the first output level, as shown in the above computing equation (3) (STEP C47). The computed comparison coefficient k1 on the first output level is stored in a comparison coefficient storing section 12a (STEP C48).

Then, the port P1 of the microcomputer 13 is opened, the port P2 of the microcomputer 13 becomes a LOW level control signal, and the impedance reducing circuit 31 is switched to a connected state on a second output level (STEP C49).

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (reference liquid voltage) Vr2 when the impedance reducing circuit 31 is connected on the second output level by the microcomputer 13 (STEP C50).

Then, in the comparison coefficient computing section 13a, a comparison coefficient k2 on the second output level is computed by dividing the interelectrode voltage (reference liquid voltage) Vr0 when the impedance reducing circuit 31 is unconnected by the interelectrode voltage (reference liquid voltage) Vr2 when the impedance reducing circuit 31 is connected on the second output level, as shown in the above computing equation (3) (STEP C51). The computed comparison coefficient k2 on the second output level is stored in the comparison coefficient storing section 12a (STEP C52).

Then, the port P2 of the microcomputer 13 is opened, the port P3 of the microcomputer 13 becomes a LOW level control signal, and the impedance reducing circuit 31 is switched to a connected state on a third output level (STEP C53).

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (reference liquid voltage) Vr3 when the impedance reducing circuit 31 is connected on the third output level by the microcomputer 13 (STEP C54).

Then, in the comparison coefficient computing section 13a, a comparison coefficient k3 on the third output level is computed by dividing the interelectrode voltage (reference liquid voltage) Vr0 when the impedance reducing circuit 31 is unconnected by the interelectrode voltage (reference liquid voltage) Vr3 when the impedance reducing circuit 31 is connected on the third output level, as shown in the above computing equation (3) (STEP C55). After the computed comparison coefficient k3 on the third output level is stored in the comparison coefficient storing section 12a (STEP C56), the adjustment mode is ended (STEP C57).

Next, specific operations of the oxidation-reduction potentiometer according to the present invention in the normal mode will be described in detail.

Figure 10:
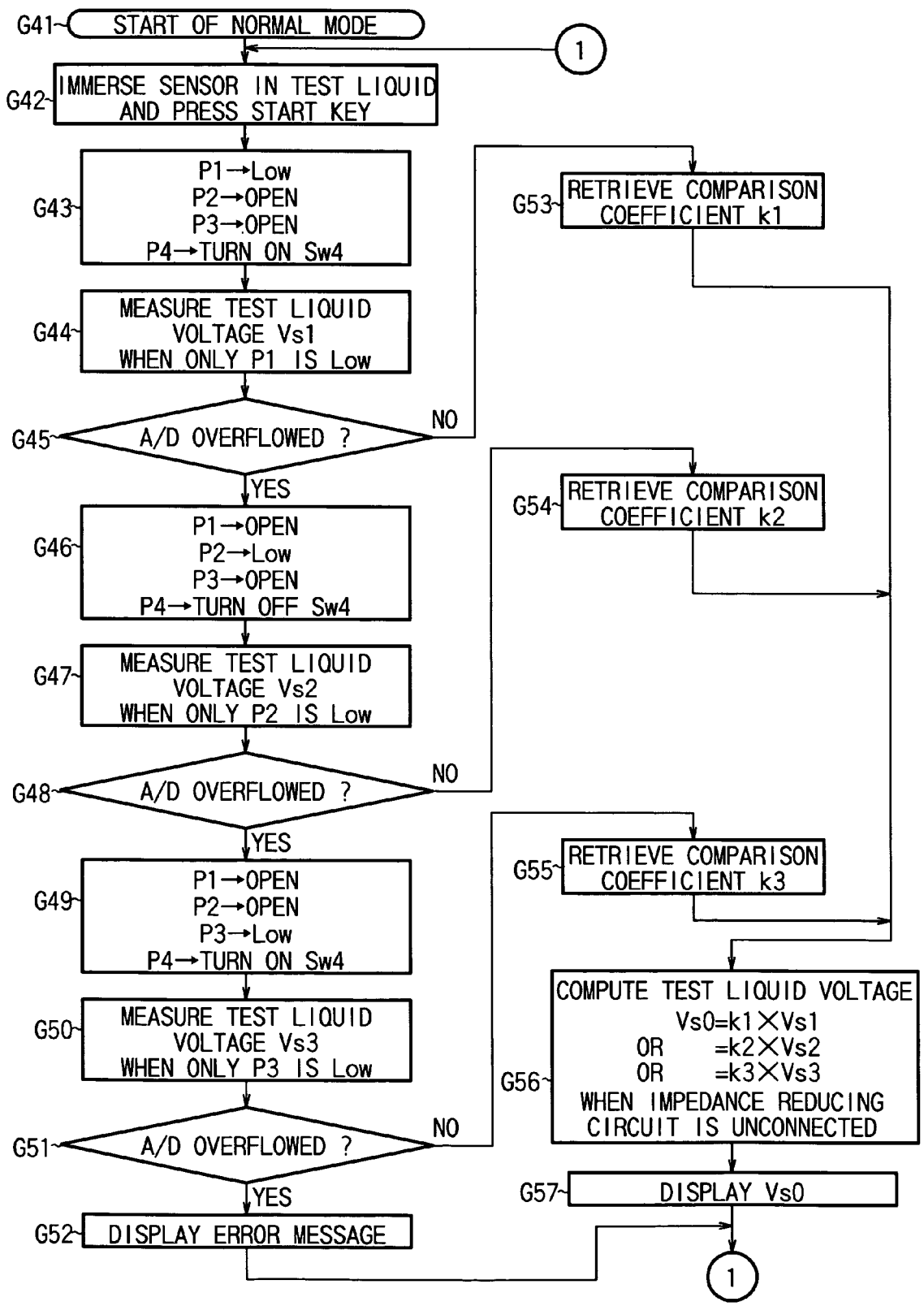
FIG. 10 is a flowchart in a normal mode of the oxidation-reduction potentiometer. (Example 3)

Immediately after the ON key 4a is pressed or after the adjustment mode is ended, the potentiometer of the present invention enters the normal mode which proceeds according to the flowchart shown in FIG. 10 (STEP G41).

Then, when the sensor 2 is immersed in a test liquid and the START key 4b is pressed (STEP G42), the port P1 of the microcomputer 13 becomes a LOW level control signal, and the reducing circuit switching switch (Sw4) 32 is turned on based on an ON control signal from the port P4 of the microcomputer 13. As a result, the impedance reducing circuit 31 is switched to a connected state on a first output level (STEP G43).

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (test liquid voltage) Vs1 when the impedance reducing circuit 31 is connected on the first output level by the microcomputer 13 (STEP G44).

Then, the microcomputer 13 determines whether the computed interelectrode voltage Vs1 exceeds the amplification tolerance of the amplifier circuit 8 (STEP G45).

Then, when the microcomputer 13 has determined that the interelectrode voltage Vs1 does not exceed the amplification tolerance (NO in STEP G45), the microcomputer 13 retrieves the comparison coefficient k1 of the first output level from the comparison coefficient storing section 12a (STEP G53).

Meanwhile, when the microcomputer 13 has determined that the interelectrode voltage Vs1 exceeds the amplification tolerance (YES in STEP G45), the port P1 of the microcomputer 13 is opened, the port P2 of the microcomputer 13 becomes a LOW level control signal, and the impedance reducing circuit 31 is switched to a connected state on a second output level (STEP G46).

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (test liquid voltage) Vs2 when the impedance reducing circuit 31 is connected on the second output level by the microcomputer 13 (STEP G47).

Then, the microcomputer 13 determines whether the computed interelectrode voltage Vs2 exceeds the amplification tolerance of the amplifier circuit 8 (STEP G48).

Then, when the microcomputer 13 has determined that the interelectrode voltage Vs2 does not exceed the amplification tolerance (NO in STEP G48), the microcomputer 13 retrieves the comparison coefficient k2 of the second output level from the comparison coefficient storing section 12a (STEP G54).

Meanwhile, when the microcomputer 13 has determined that the interelectrode voltage Vs2 exceeds the amplification tolerance (YES in STEP G48), the port P2 of the microcomputer 13 is opened, the port P3 of the microcomputer 13 becomes a LOW level control signal, and the impedance reducing circuit 31 is switched to a connected state on a third output level (STEP G49).

Then, an interelectrode voltage (analog signal) generated between the working electrode 6 and the reference electrode 7 at that time is amplified by the amplifier circuit 8, converted into a digital signal by the A/D converter 9, and computed as an interelectrode voltage (test liquid voltage) Vs3 when the impedance reducing circuit 31 is connected on the third output level by the microcomputer 13 (STEP G50).

Then, the microcomputer 13 determines whether the computed interelectrode voltage Vs3 exceeds the amplification tolerance of the amplifier circuit 8 (STEP G51).

Then, when the microcomputer 13 has determined that the interelectrode voltage Vs3 does not exceed the amplification tolerance (NO in STEP G51), the microcomputer 13 retrieves the comparison coefficient k3 of the third output level from the comparison coefficient storing section 12a (STEP G55).

Meanwhile, when the microcomputer 13 has determined that the interelectrode voltage Vs3 exceeds the amplification tolerance (YES in STEP G51), the microcomputer 13 displays an error message which indicates that the interelectrode voltage is out of the amplification tolerance on the display 5 (STEP G52).

Then, in an oxidation-reduction potential computing section 13b, an interelectrode voltage (test liquid voltage) when the impedance reducing circuit 31 is unconnected, i.e., an oxidation-reduction potential Vs0, is computed by multiplying the interelectrode voltage (test liquid voltage) VsN when the impedance reducing circuit 31 is connected on a specific output level by the comparison coefficient kN of the specific output level stored in the comparison coefficient storing section 12a, as shown in the above computing equation (4) (STEP G56). The result is displayed on the display 5 (STEP G57).

Subsequently, the present potentiometer can return to STEP G42 and repeat the processes.

EXAMPLE 4

First, the specific constitution of an oxidation-reduction potentiometer according to the present invention will be described by use of an external view shown in FIG. 11 and a block diagram shown in FIG. 12.

An oxidation-reduction potentiometer as Example 4 has, when viewed from the outside, a main unit 1 which has an input section 4 and a display 5 on the front side, a sensor 41 which has a working electrode 48, a reference electrode 49 and a conductivity measuring electrode 42, and a cable 3 which connects the sensor 41 to the main unit 1. The oxidation-reduction potentiometer also has an electronic substrate and a power supply section 14 inside the main unit 1. The electronic substrate has an amplifier circuit 8, a conductivity measuring circuit 43, an A/D converter 44, an impedance reducing circuit 45, a reducing circuit switching switch 46, a conductivity measurement switching switch 47, an EEPROM 12, and a microcomputer 13. These roughly constitute the oxidation-reduction potentiometer as a whole.

The input section 4 comprises an ON key 4a, a START key 4b, a MODE key 4c, a +key 4d and a −key 4e and is used for supplying electric power, staring a measurement, switching or the like. The ON key 4a is used to start supplying electric power from the power supply section 14 to components in the electrical system. The START key 4b is used to start a measurement. The MODE key 4c is used to switch between an adjustment mode and a measurement mode. The +key 4d and the −key 4e are used to select an item, a numerical value or the like displayed on the display.

The display 5 displays an input status, measurement results, various modes, remaining battery power and the like.

The sensor 41 is formed by forming an outer glass tube (shown transparent in FIG. 11) 41b on the outer side of an inner glass tube (shown transparent in FIG. 11) 41a in such a manner that the outer tube 41b covers the inner tube 41a with space therebetween, providing platinum (Pt) 41c and the conductivity measuring electrode 42 from the outer side of the inner glass tube 41a to the outer side of the outer glass tube 41b, setting an internal electrode 41d which is silver (Ag) covered with silver chloride (AgCl) in the inner glass tube 41a, filling liquid or gelled sodium chloride (NaCl) or potassium chloride (KCl) in the inner glass tube 41a, providing a liquid junction 41e from the inside of the inner glass tube 41a to the outer sides of the inner glass tube 41a and the outer glass tube 41b, and connecting the platinum (Pt) 41c and the internal electrode 41d to the electronic substrate by use of conducting wires 41f, 41g and 41h.

The platinum (Pt) 41c portion corresponds to the working electrode 48. The inner glass tube 41a, the internal electrode 41d, sodium chloride (NaCl) or potassium chloride (KCl) and the liquid junction 41e correspond to the reference electrode 49.

The power supply section 14 supplies electric power to the components in the electrical system.

The amplifier circuit 8 amplifies an interelectrode voltage (analog signal) which is a difference between a measured potential generated from the working electrode 48 and indicating the degree of oxidation-reduction reaction and a measured reference potential generated from the reference electrode 49. The conductivity measuring circuit 43 amplifies an interelectrode voltage (analog signal) which is a difference between a potential generated from the conductivity measuring electrode 42 and a potential generated from the working electrode 48. The A/D converter 44 converts the interelectrode voltage amplified by the amplifier circuit 8 or conductivity measuring circuit 43 into a digital signal.

The impedance reducing circuit 45 comprises resistances R11 and R12 having different resistance values which are disposed between the working electrode 48 and the reference electrode 49 such that they can be switched between an unconnected state and a connected state by the reducing circuit switching switch 46. The circuit 45 reduces an impedance occurring between the working electrode 48 and the reference electrode 49 when the electrodes are immersed in a liquid.

The reducing circuit switching switch 46 switches the impedance reducing circuit 45 between an unconnected state and a connected state based on a control signal from the microcomputer 13. The conductivity measurement switching switch 47 switches connection of the working electrode 48 to the conductivity measuring circuit 43 or the amplifier circuit 8 based on a control signal from the microcomputer 13.

The EEPROM 12 has a comparison coefficient storing section 12a and stores various data. The comparison coefficient storing section 12a stores comparison coefficients computed by a comparison coefficient computing section 13a which will be described later.

The microcomputer 13 has the comparison coefficient computing section 13a, an oxidation-reduction potential computing section 13b and a conductivity determining section 13c. The microcomputer 13 computes various data and controls switching of the reducing circuit switching switch 46 and the conductivity measurement switching switch 47 and determinations of various data.

The comparison coefficient computing section 13a computes a comparison coefficient for a specific reference liquid based on an interelectrode voltage (reference liquid voltage) for the specific reference liquid from the A/D converter 44 when the impedance reducing circuit 45 is in an unconnected state and an interelectrode voltage (reference liquid voltage) for the specific reference liquid from the A/D converter 44 when the impedance reducing circuit 45 is in a connected state. The comparison coefficient computing section 13a performs this computation for a plurality of reference liquids. More specifically, the comparison coefficient computing section 13a computes a comparison coefficient k1 for a reference liquid by dividing an interelectrode voltage Vra0 for the reference liquid from the A/D converter 44 when the impedance reducing circuit is in an unconnected state by an interelectrode voltage Vra1 for the reference liquid from the A/D converter 44 when the impedance reducing circuit 45 is in a connected state and also computes a comparison coefficient k2 for another reference liquid by dividing an interelectrode voltage Vrb0 for the reference liquid from the A/D converter 44 when the impedance reducing circuit 45 is in an unconnected state by an interelectrode voltage Vrb1 for the reference liquid from the A/D converter 44 when the impedance reducing circuit 45 is in a connected state, as shown in the following computing equations (5) and (6).

$$k1 = Vra0/Vra1 \quad (5)$$

$$k2 = Vrb0/Vrb1 \quad (6)$$

The oxidation-reduction potential computing section 13b computes an oxidation-reduction potential based on an interelectrode voltage from the A/D converter 44 when the impedance reducing circuit 45 is in a connected state and a comparison coefficient corresponding to the conductivity of a test liquid out of comparison coefficients stored in the comparison coefficient storing section 12a, when the impedance reducing circuit 45 has been switched to the connected state corresponding to the conductivity of the test liquid based on a control signal from the microcomputer 13. More specifically, the oxidation-reduction potential computing section 13b computes an interelectrode voltage (test liquid voltage) from the A/D converter 44 when the impedance reducing circuit 45 is in an unconnected state, i.e., an oxidation-reduction potential Vs0, by multiplying an interelectrode voltage Vs1 or Vs2 from the A/D converter 44 when the impedance reducing circuit 45 is in a connected state corresponding to the conductivity of a test liquid by the comparison coefficient k1 or k2 corresponding to the conductivity of the test liquid out of the comparison coefficients stored in the comparison coefficient storing section 12a, as shown in the following computing equations (7) and (8).

$$Vs0 = k1 \times Vs1 \quad (7)$$

$$Vs0 = k2 \times Vs2 \quad (8)$$

The conductivity determining section 13c compares the conductivity of the test liquid from the A/D converter 44 with reference conductivity stored in the section 13c and selects a comparison coefficient to be used in the oxidation-reduction potential computing section 13b.

The reducing circuit switching switch 46 and the microcomputer 13 constitute reducing circuit switching means. Further, the reducing circuit switching switch 46 and the microcomputer 13 also constitute conductivity measurement switching means. Further, the conductivity measuring electrode 42, the conductivity measuring circuit 43, the A/D converter 44 and the microcomputer 13 constitute conductivity measuring means. Further, the amplifier circuit 8, the A/D converter 44 and the microcomputer 13 constitute interelectrode voltage measuring means. Further, the reducing circuit switching means, the interelectrode voltage measuring means, the comparison coefficient computing section 13a, the comparison coefficient storing section 12a and the oxidation-reduction potential computing section 13b constitute oxidation-reduction potential measuring means.

Figure 13:
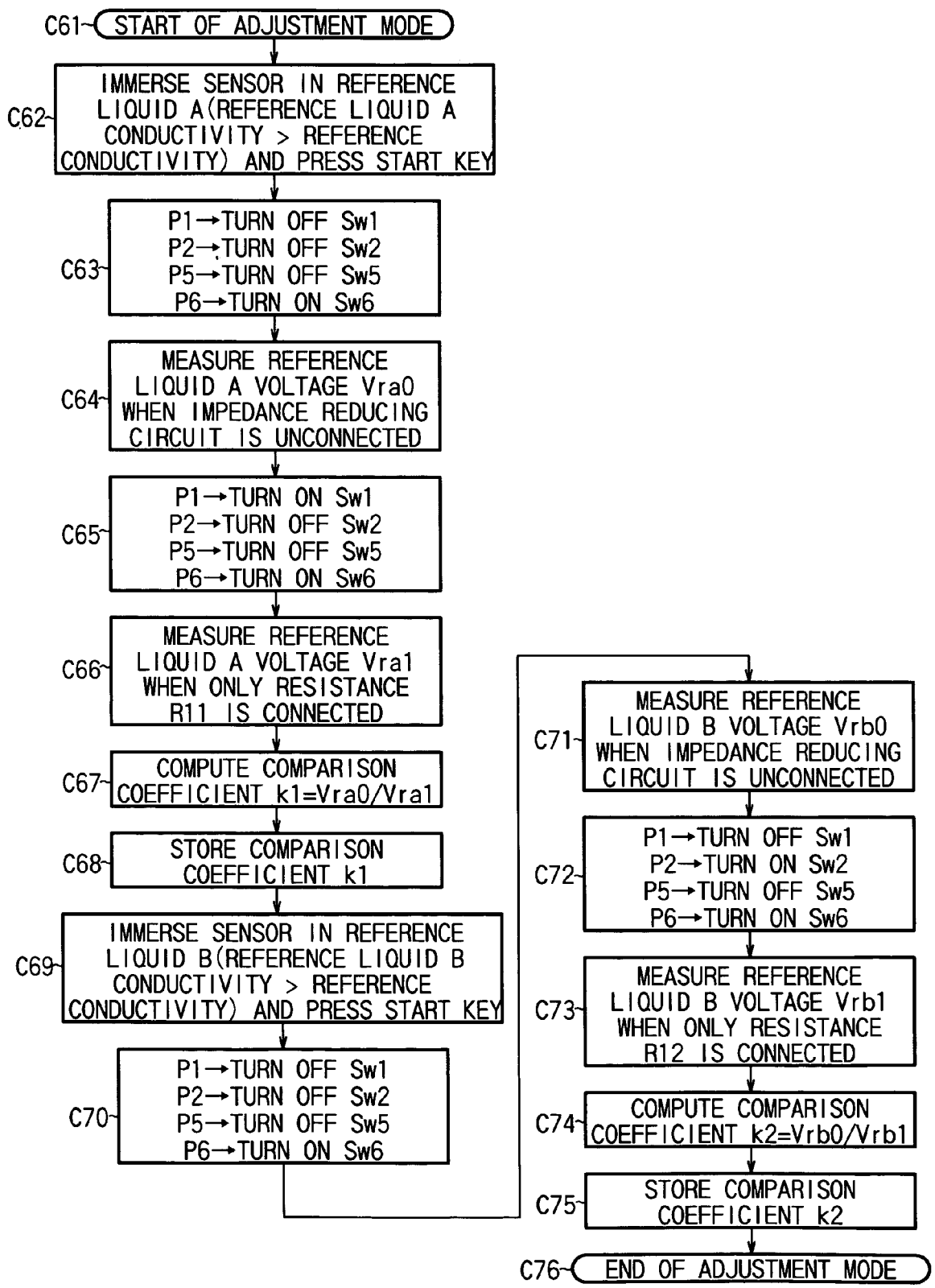
FIG. 13 is a flowchart in an adjustment mode of the oxidation-reduction potentiometer. (Example 4)

Next, specific operations of the oxidation-reduction potentiometer according to the present invention will be described by use of a flowchart in an adjustment mode shown in FIG. 13 and a flowchart in a normal mode shown in FIG. 14.

First, specific operations in the adjustment mode will be described in detail.

At the press of the ON key 4a, electric power is supplied from the power supply section 14 to the components in the electrical system, and the potentiometer of the present invention enters the normal mode to be described later in accordance with the flowchart shown in FIG. 14 (STEP G61). Then, when the MODE key 4c is pressed subsequently, the present potentiometer enters the adjustment mode which proceeds according to the flowchart shown in FIG. 13 (STEP C61).

Then, when the sensor 41 is immersed in a known reference liquid A (conductivity of reference liquid A>reference conductivity) and the START key 4b is pressed (STEP C62), the reducing circuit switching switch (Sw1, Sw2) 46 and Sw5 in the conductivity measurement switching switch 47 are turned off based on OFF control signals from the ports P1, P2 and P5 of the microcomputer 13, Sw6 in the conductivity measurement switching switch 47 is turned on based on an ON control signal from the port P6 of the microcomputer 13, the working electrode is connected to the reference electrode, and the impedance reducing circuit 45 is switched to an unconnected state (STEP C63). The reference conductivity is conductivity used as a reference to determine whether the conductivity of a test liquid is closer to the conductivity of the reference liquid A or the conductivity of a reference liquid B in the following description.

Then, an interelectrode voltage (analog signal) for the reference liquid A which is generated between the working electrode 48 and the reference electrode 49 at that time is amplified by the amplifier circuit 8, converted into a digital signal by the A/D converter 44, and computed as an interelectrode voltage (reference liquid voltage A) Vra0 when the impedance reducing circuit 45 is unconnected by the microcomputer 13 (STEP C64).

Then, the reducing circuit switching switch Sw1 is turned on based on an ON control signal from the port P1 of the microcomputer 13, whereby a resistance in the impedance reducing circuit 45 which corresponds to the conductivity of the reference liquid A is switched to a connected state (STEP C65).

Then, an interelectrode voltage (analog signal) for the reference liquid A which is generated between the working electrode 48 and the reference electrode 49 at that time is amplified by the amplifier circuit 8, converted into a digital signal by the A/D converter 44, and computed as an interelectrode voltage (reference liquid voltage A) Vra1 when the resistance R11 corresponding to the conductivity of the reference liquid A is connected by the microcomputer 13 (STEP C66).

Then, in the comparison coefficient computing section 13a, a comparison coefficient k1 corresponding to the conductivity of the reference liquid A is computed by dividing the interelectrode voltage (reference liquid voltage) Vra0 for the reference liquid A when the impedance reducing circuit 45 is unconnected by the interelectrode voltage (reference liquid voltage A) Vra1 when the resistance R11 corresponding to the conductivity of the reference liquid A is connected, as shown in the above computing equation (5) (STEP C67) The computed comparison coefficient k1 corresponding to the conductivity of the reference liquid A is stored in the comparison coefficient storing section 12a (STEP C68).

Then, when the sensor 41 is immersed in a known reference liquid B (conductivity of reference liquid B≦reference conductivity) and the START key 4b is pressed (STEP C69), the reducing circuit switching switch (Sw1, Sw2) 46 and the Sw5 in the conductivity measurement switching switch 47 are turned off based on OFF control signals from the ports P1, P2 and P5 of the microcomputer 13, the Sw6 in the conductivity measurement switching switch 47 is turned on based on an ON control signal from the port P6 of the microcomputer 13, the working electrode is connected to the reference electrode, and the impedance reducing circuit 45 is switched to an unconnected state (STEP C70).

Then, an interelectrode voltage (analog signal) for the reference liquid B which is generated between the working electrode 48 and the reference electrode 49 at that time is amplified by the amplifier circuit 8, converted into a digital signal by the A/D converter 44, and computed as an interelectrode voltage (reference liquid voltage B) Vrb0 when the impedance reducing circuit 45 is unconnected by the microcomputer 13 (STEP C71).

Then, Sw2 in the reducing circuit switching switch 46 is turned on based on an ON control signal from the port P2 of the microcomputer 13, whereby the resistance R12 in the impedance reducing circuit 45 which corresponds to the conductivity of the reference liquid B is switched to a connected state (STEP C72).

Then, an interelectrode voltage (analog signal) for the reference liquid B which is generated between the working electrode 48 and the reference electrode 49 at that time is amplified by the amplifier circuit 8, converted into a digital signal by the A/D converter 44, and computed as an interelectrode voltage (reference liquid voltage B) Vrb1 when the resistance R12 corresponding to the conductivity of the reference liquid B is connected by the microcomputer 13 (STEP C73).

Then, in the comparison coefficient computing section 13a, a comparison coefficient k2 corresponding to the conductivity of the reference liquid B is computed by dividing the interelectrode voltage (reference liquid voltage) Vrb0 for the reference liquid B when the impedance reducing circuit 45 is unconnected by the interelectrode voltage (reference liquid voltage B) Vrb1 when the resistance R12 corresponding to the conductivity of the reference liquid B is connected, as shown in the above computing equation (6) (STEP C74). After the computed comparison coefficient k2 corresponding to the conductivity of the reference liquid B is stored in the comparison coefficient storing section 12a (STEP C75), the adjustment mode is ended (STEP C76).

Next, specific operations of the oxidation-reduction potentiometer according to the present invention in the normal mode will be described in detail.

Figure 14:
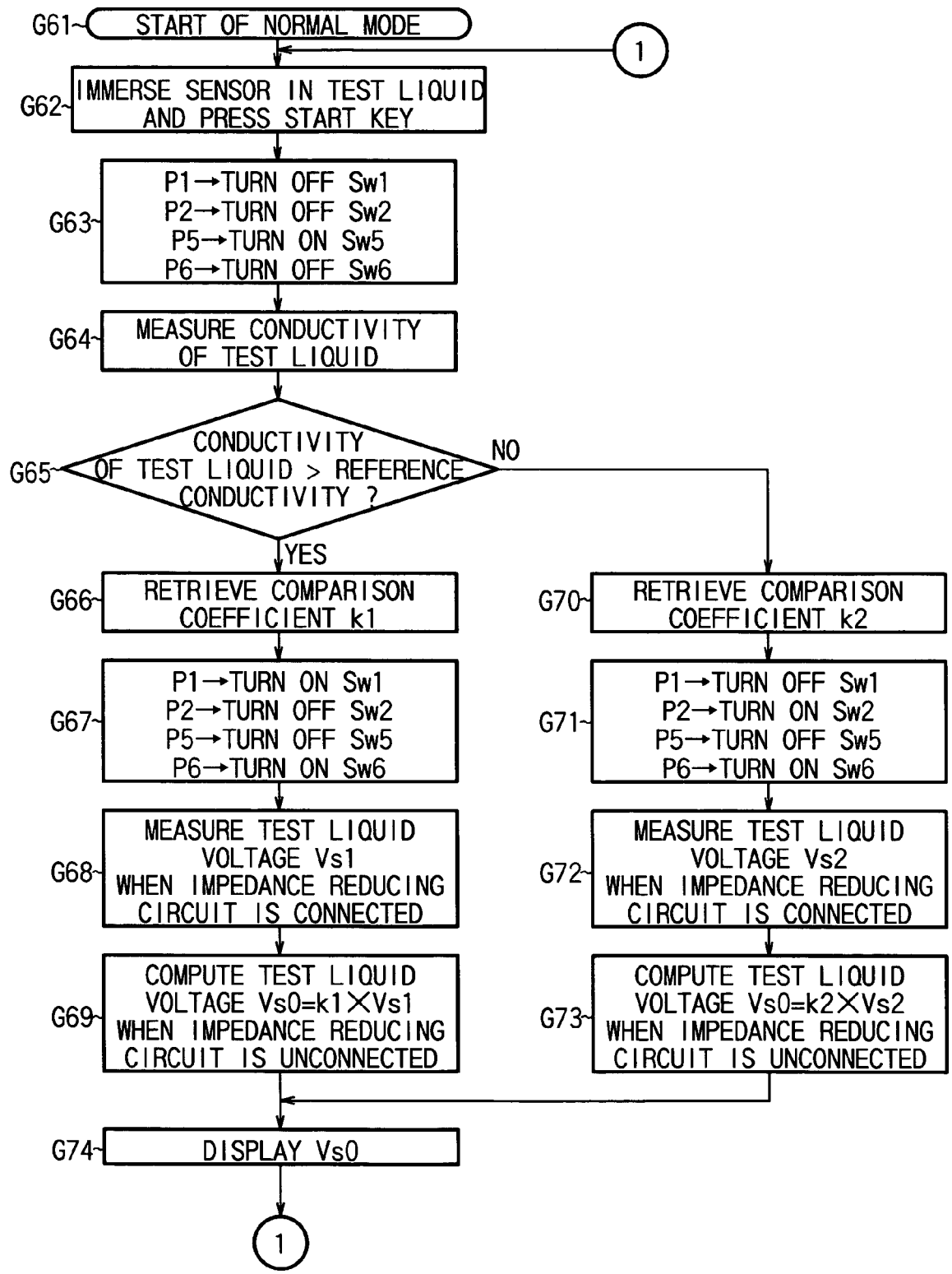
FIG. 14 is a flowchart in a normal mode of the oxidation-reduction potentiometer. (Example 4)

Immediately after the ON key 4a is pressed or after the adjustment mode is ended, the potentiometer of the present invention enters the normal mode which proceeds according to the flowchart shown in FIG. 14 (STEP G61).

Then, when the sensor 41 is immersed in a test liquid and the START key 4b is pressed (STEP G62), the reducing circuit switching switch (Sw1, Sw2) 46 and the Sw6 in the conductivity measurement switching switch 47 are turned off based on OFF control signals from the ports P1, P2 and P6 of the microcomputer 13, the Sw5 in the conductivity measurement switching switch 47 is turned on based on an ON control signal from the port P5 of the microcomputer 13, the working electrode is connected to the conductivity measuring electrode, and the impedance reducing circuit 45 is switched to an unconnected state (STEP G63).

Then, an interelectrode voltage (analog signal) which is a difference between a potential generated from the conductivity measuring electrode 41 and a potential generated from the working electrode 48 is amplified in the conductivity measuring circuit 43, the interelectrode voltage is converted into a digital signal in the A/D converter 44, and the conductivity of the test liquid is computed in the conductivity determining section 13c (STEP G64).

Then, it is determined whether the computed conductivity of the test liquid is higher than the reference conductivity (STEP G65).

Then, when it has been determined that the computed conductivity is higher than the reference conductivity (YES in STEP G65), the comparison coefficient k1 corresponding to the conductivity of the reference liquid A is retrieved from the comparison coefficient storing section (STEP G66).

Then, the Sw5 in the conductivity measurement switching switch 47 is turned off based on an OFF control signal from the port P5 of the microcomputer 13, the Sw1 in the reducing circuit switching switch 46 and the Sw6 in the conductivity measurement switching switch 47 are turned on based on ON control signals from the ports P1 and P6 of the microcomputer 13, the working electrode is connected to the reference electrode, and the impedance reducing circuit 45 is switched to a connected state corresponding to the conductivity of the reference liquid A (STEP G67).

Then, an interelectrode voltage (analog signal) for the test liquid which is generated between the working electrode 48 and the reference electrode 49 at that time is amplified by the amplifier circuit 8, converted into a digital signal by the A/D converter 44, and computed as an interelectrode voltage (test liquid voltage) Vs1 when the impedance reducing circuit 45 is connected by the microcomputer 13 (STEP G68).

Then, in the oxidation-reduction potential computing section 13b, an interelectrode voltage (test liquid voltage) when the impedance reducing circuit 45 is unconnected, i.e., an oxidation-reduction potential Vs0, is computed by multiplying the interelectrode voltage (test liquid voltage) Vs1 when the impedance reducing circuit 45 is connected by the corresponding comparison coefficient k1 which is stored in the comparison coefficient storing section 12a, as shown in the above computing equation (7) (STEP G69).

Meanwhile, when it has been determined in STEP G65 that the computed conductivity is not higher than the reference conductivity, i.e., the computed conductivity is equal to or lower than the reference conductivity (NO in STEP G65), the comparison coefficient k2 corresponding to the conductivity of the reference liquid B is retrieved from the comparison coefficient storing section 12a (STEP G70).

Then, the Sw5 in the conductivity measurement switching switch 47 is turned off based on an OFF control signal from the port P5 of the microcomputer 13, the Sw2 in the reducing circuit switching switch 46 and the Sw6 in the conductivity measurement switching switch 47 are turned on based on ON control signals from the ports P2 and P6 of the microcomputer 13, the working electrode is connected to the reference electrode, and the impedance reducing circuit 45 is switched to a connected state corresponding to the conductivity of the reference liquid B (STEP G71).

Then, an interelectrode voltage (analog signal) for the test liquid which is generated between the working electrode 48 and the reference electrode 49 at that time is amplified by the amplifier circuit 8, converted into a digital signal by the A/D converter 44, and computed as an interelectrode voltage (test liquid voltage) Vs2 when the impedance reducing circuit 45 is connected by the microcomputer 13 (STEP G72).

Then, in the oxidation-reduction potential computing section 13b, an interelectrode voltage (test liquid voltage) when the impedance reducing circuit 45 is unconnected, i.e., an oxidation-reduction potential Vs0, is computed by multiplying the interelectrode voltage (test liquid voltage) Vs2 when the impedance reducing circuit 45 is connected by the corresponding comparison coefficient k2 which is stored in the comparison coefficient storing section 12a, as shown in the above computing equation (8) (STEP G73).

In STEP G69 or STEP G73, the result is displayed on the display (STEP G74). Subsequently, the present potentiometer can return to STEP G62 and repeat the processes.

EXAMPLE 5

Figure 15:
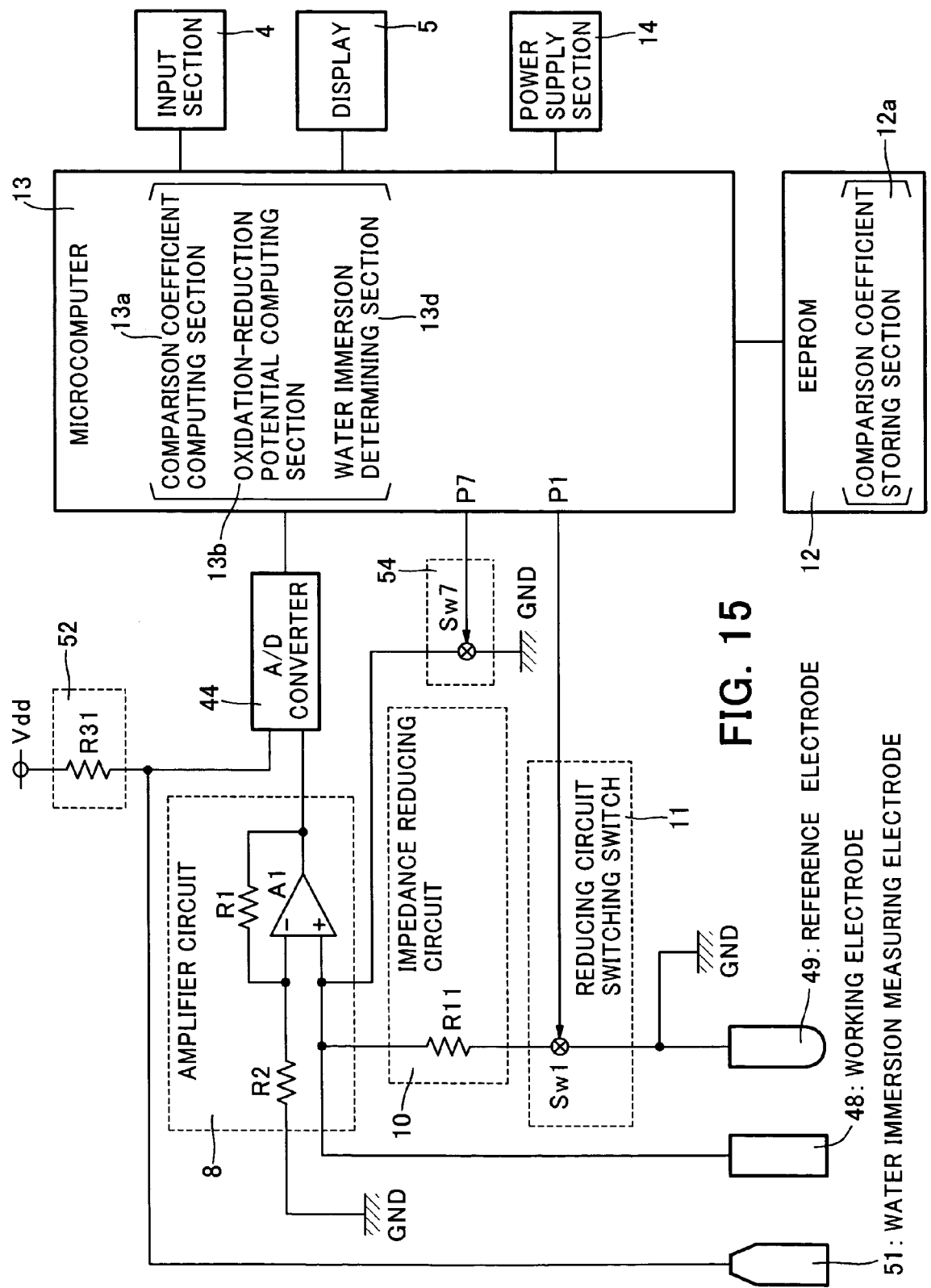
FIG. 15 is a block diagram illustrating the oxidation-reduction potentiometer. (Example 5)

First, the specific constitution of an oxidation-reduction potentiometer according to the present invention will be described by use of an external view shown in FIG. 11 and a block diagram shown in FIG. 15.

An oxidation-reduction potentiometer as Example 5 has, when viewed from the outside, a main unit 1 which has an input section 4 and a display 5 on the front side, a sensor 41 which has a working electrode 48, a reference electrode 49 and a water immersion measuring electrode 51, and a cable 3 which connects the sensor 41 to the main unit 1. The oxidation-reduction potentiometer also has an electronic substrate and a power supply section 14 inside the main unit 1. The electronic substrate has an amplifier circuit 8, a water immersion measuring circuit 52, an A/D converter 44, an impedance reducing circuit 10, a reducing circuit switching switch 11, a water immersion measurement switching switch 54, an EEPROM 12 and a microcomputer 13. These roughly constitute the oxidation-reduction potentiometer as a whole.

Detailed descriptions of the input section 4, display 5, power supply section 14, amplifier circuit 8, impedance reducing circuit 10, reducing circuit switching switch 11, EEPROM 12, comparison coefficient computing section 13a and oxidation-reduction potential computing section 13b are omitted because they are the same as those in Example 1.

Figure 11:
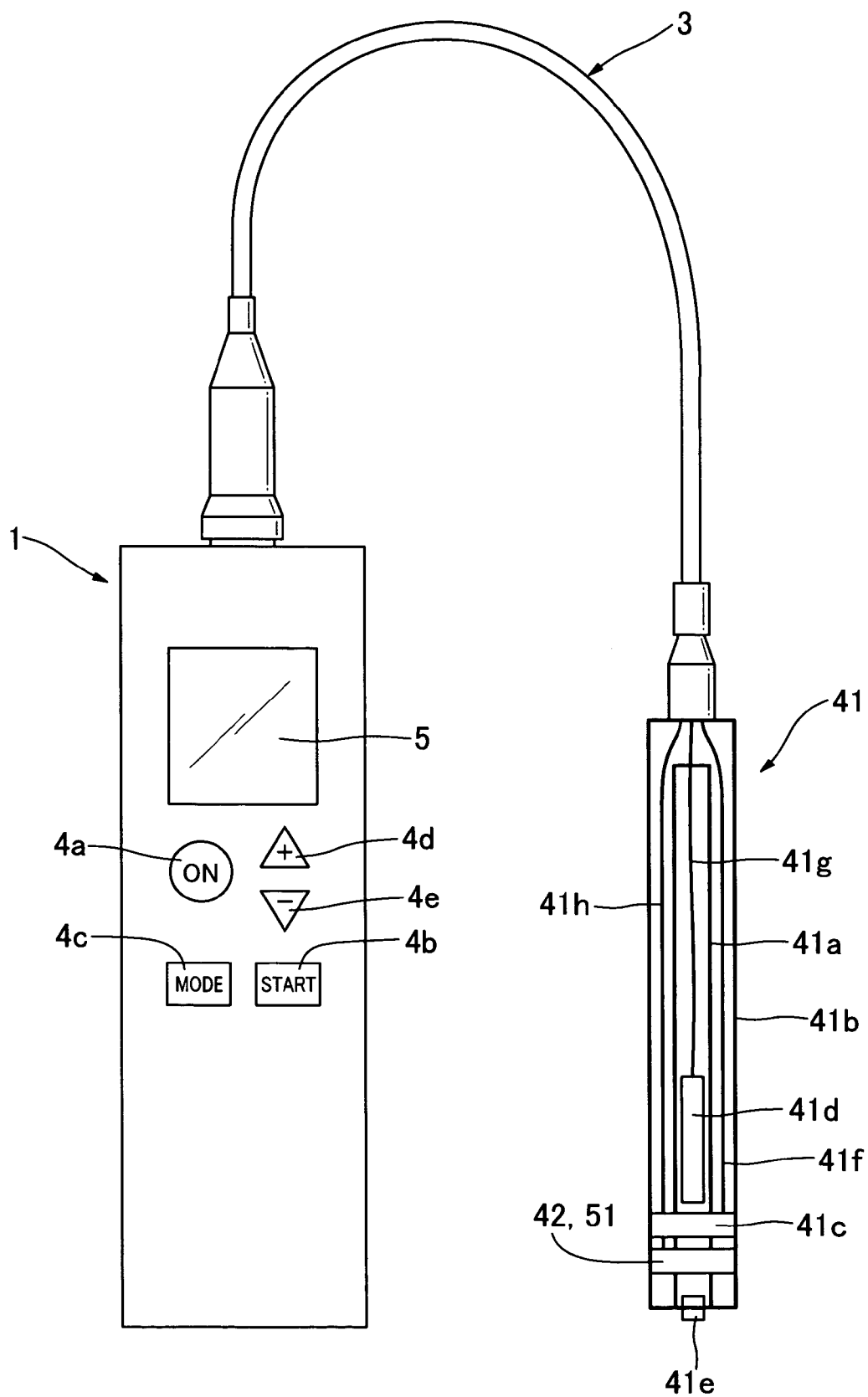
FIG. 11 is an external view of an oxidation-reduction potentiometer. (Examples 4 and 5)
Figure 12:
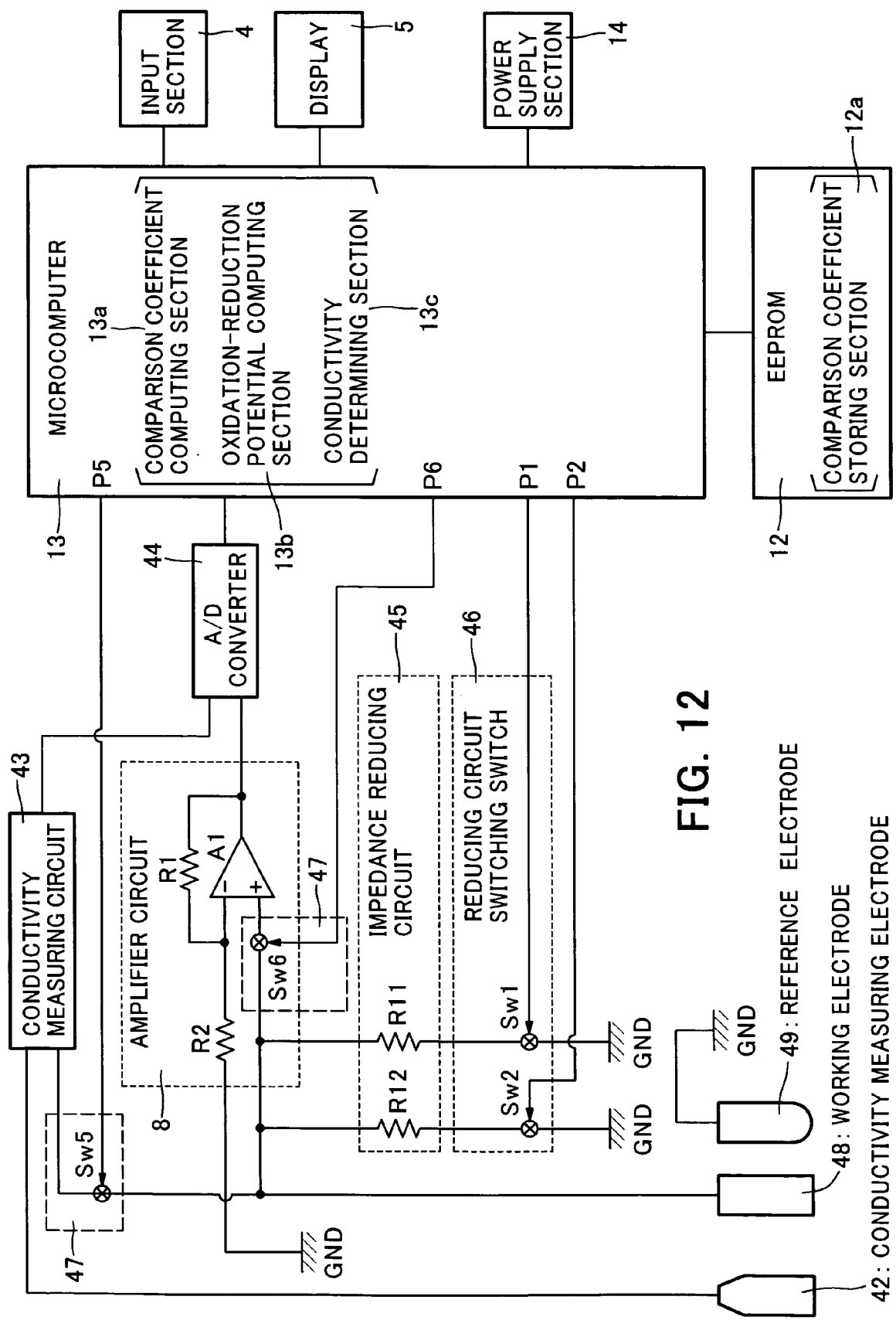
FIG. 12 is a block diagram illustrating the oxidation-reduction potentiometer. (Example 4)

The sensor 41 has the same form as that described in Example 4 with reference to FIG. 11 and comprises the water immersion measuring electrode 51 in place of the conductivity measuring electrode 42.

The water immersion measuring circuit 52 generates a water immersion detection potential together with the water immersion measuring electrode 51.

The A/D converter 44 converts a voltage from the amplifier circuit 8, water immersion measuring electrode 51 or water immersion measuring circuit 52 into a digital signal.

The water immersion measurement switching switch 54 switches connection to the amplifier circuit 8 to the ground based on a control signal from the microcomputer 13.

The microcomputer 13 has the comparison coefficient computing section 13a, the oxidation-reduction potential computing section 13b and a water immersion determining section 13d. The microcomputer 13 computes various data and controls switching of the reducing circuit switching switch 11 and the water immersion measurement switching switch 54 and determinations of various data.

The water immersion determining section 13d determines whether the sensor 41 is immersed in a liquid, by comparing a water immersion measured voltage from the A/D converter 44 with a determination voltage stored in advance.

The water immersion measurement switching switch 54 and the microcomputer 13 constitute water immersion measurement switching means. Further, the water immersion measuring electrode 51, the water immersion measuring circuit 52, the A/D converter 44 and the microcomputer 13 constitute water immersion measuring means.

Figure 16:
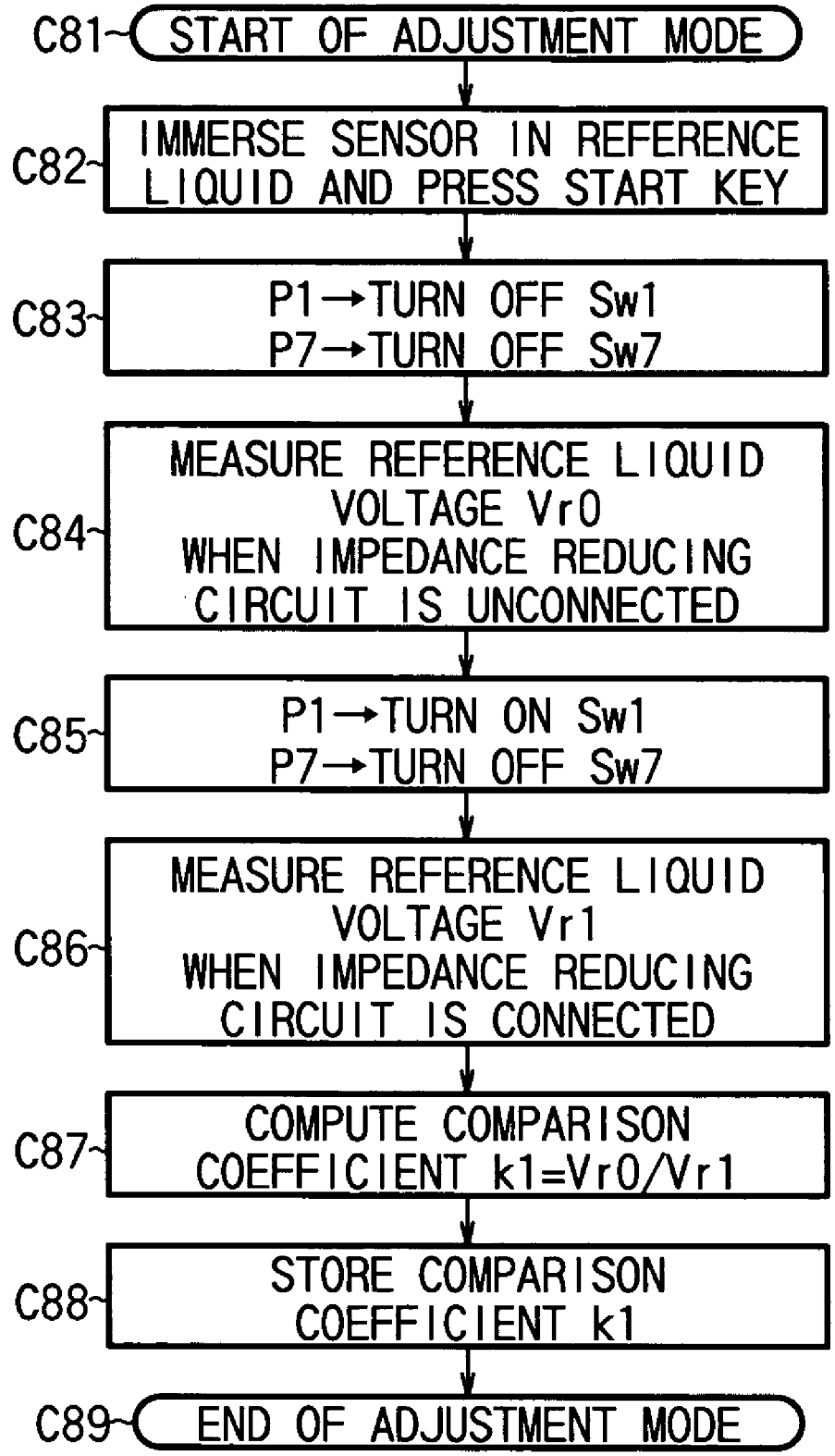
FIG. 16 is a flowchart in an adjustment mode of the oxidation-reduction potentiometer. (Example 5)
Figure 17:
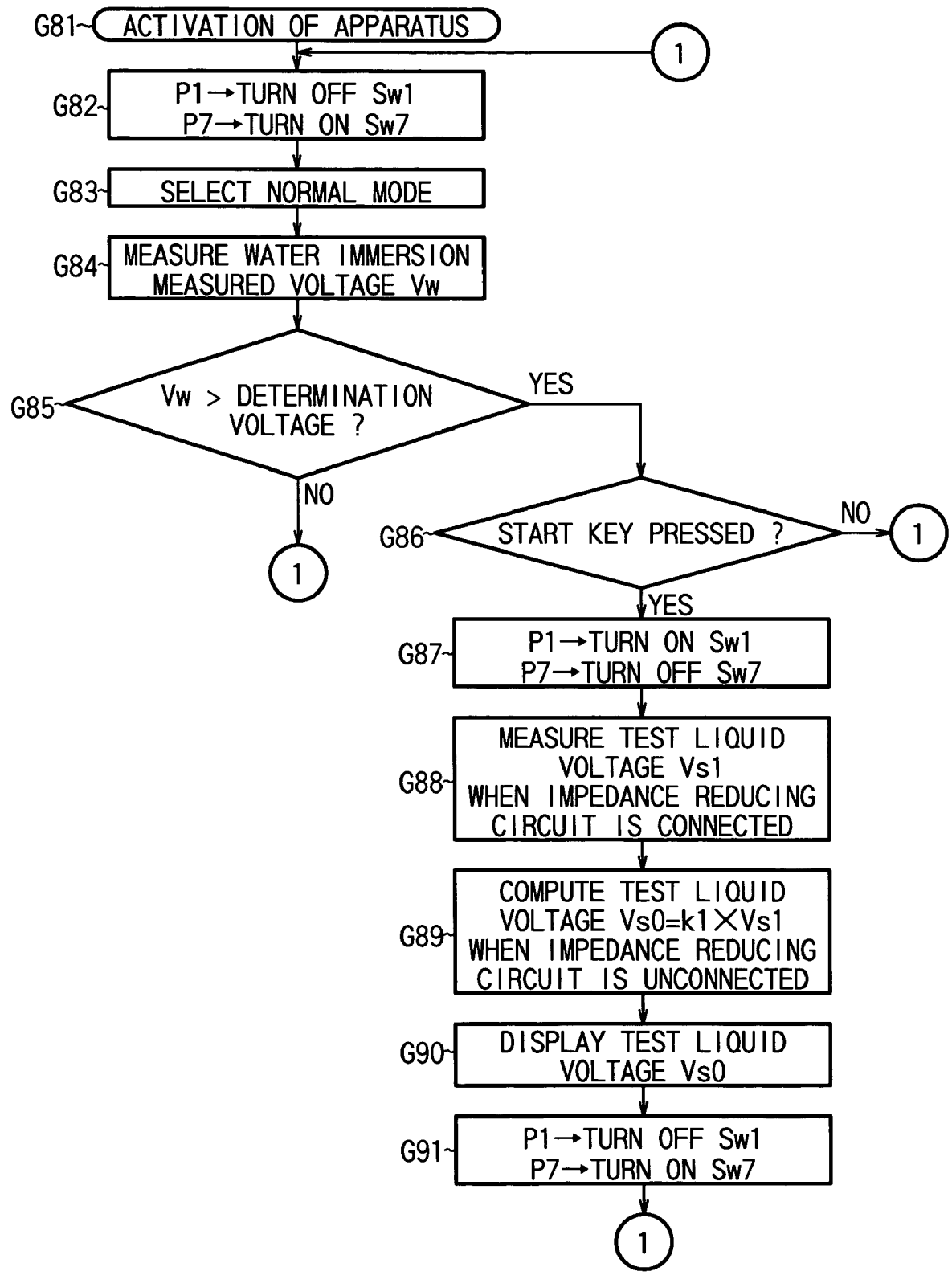
FIG. 17 is a main flowchart of the oxidation-reduction potentiometer. (Example 5)

Next, specific operations of the oxidation-reduction potentiometer according to the present invention will be described by use of a flowchart in an adjustment mode shown in FIG. 16 and a main flowchart shown in FIG. 17.

First, specific operations in the adjustment mode will be described in detail.

At the press of an ON key 4a, electric power is supplied from the power supply section 14 to the components in the electrical system, and the potentiometer of the present invention enters a standby mode. Then, when a MODE key 4c is pressed, the adjustment mode is selected, and the present potentiometer enters the adjustment mode which proceeds according to the flowchart shown in FIG. 16 (STEP C81). The adjustment mode and a normal mode are switched from one to the other each time the MODE key 4c is pressed.

Then, when the sensor 41 is immersed in a reference liquid and a START key 4b is pressed (STEP C82), the reducing circuit switching switch (Sw1) 11 and the water immersion measurement switching switch (Sw7) 54 are turned off based on OFF control signals from the ports P1 and P7 of the microcomputer 13, the working electrode is connected to the reference electrode, and the impedance reducing circuit 10 is switched to an unconnected state (STEP C83).

Then, an interelectrode voltage (analog signal) generated between the working electrode 48 and the reference electrode 49 at that time is amplified by the amplifier circuit 8, converted into a digital signal by the A/D converter 44, and computed as an interelectrode voltage (reference liquid voltage) Vr0 when the impedance reducing circuit 10 is unconnected by the microcomputer 13 (STEP C84).

Then, the reducing circuit switching switch (Sw1) 11 is turned on based on an ON control signal from the port P1 of the microcomputer 13. Thereby, the impedance reducing circuit 10 is switched to a connected state (STEP C85).

Then, an interelectrode voltage (analog signal) generated between the working electrode 48 and the reference electrode 49 at that time is amplified by the amplifier circuit 8, converted into a digital signal by the A/D converter 44, and computed as an interelectrode voltage (reference liquid voltage) Vr1 when the impedance reducing circuit 10 is connected by the microcomputer 13 (STEP C86).

Then, in the comparison coefficient computing section 13a, a comparison coefficient k1 is computed by dividing the interelectrode voltage (reference liquid voltage) Vr0 when the impedance reducing circuit 10 is unconnected by the interelectrode voltage (reference liquid voltage) Vr1 when the impedance reducing circuit 10 is connected, as shown in the computing equation (1) in Example 1 (STEP C87). After the computed comparison coefficient k1 is stored in a comparison coefficient storing section 12a (STEP C88), the adjustment mode is ended (STEP C89).

Next, specific operations of the oxidation-reduction potentiometer according to the present invention in action (normal mode) will be described in detail.

Immediately after the ON key 4a is pressed or after the adjustment mode is ended, electric power is supplied from the power supply section 14 to the components in the electrical system (STEP G81), the reducing circuit switching switch (Sw1) 11 is turned off based on an OFF control signal from the port P1 of the microcomputer 13, and the water immersion measurement switching switch (Sw7) 54 is turned on based on an ON control signal from the port P7 of the microcomputer 13, whereby the potentiometer of the present invention enters a standby mode (STEP C82).

Then, when the normal mode is selected by pressing the MODE key 4c which switches the adjustment mode and the normal mode from one to the other each time it is pressed (STEP C81), an interelectrode voltage (analog signal) between the water immersion measuring electrode 51 and the working electrode 48 is converted into a digital signal by the A/D converter 44 and taken in as a water immersion measured voltage Vw by the microcomputer 13 (STEP C84).

Then, in the water immersion determining section 13d, it is determined whether the water immersion measured voltage Vw is higher than the determination voltage (STEP G85).

Then, when the water immersion measured voltage Vw is not higher than the determination voltage (NO in STEP G85), the potentiometer can return to STEP G84 and repeat the processes. Meanwhile, when the water immersion measured voltage Vw is higher than the determination voltage (YES in STEP G85), it is determined whether the START key 4b has been pressed (STEP G86).

Then, when the START key 4b has not been pressed (NO in STEP G86), the potentiometer can return to STEP G84 and repeat the processes. Meanwhile, when the START key 4b has been pressed (YES in STEP G86), the reducing circuit switching switch (Sw1) 11 is turned on based on an ON control signal from the port P1 of the microcomputer 13, the water immersion measurement switching switch (Sw7) 53 is turned off based on an OFF control signal from the port P7 of the microcomputer 13, the working electrode is connected to the reference electrode, and the impedance reducing circuit 10 is switched to a connected state (STEP G87).

Then, an interelectrode voltage (analog signal) generated between the working electrode 48 and the reference electrode 49 at that time is amplified by the amplifier circuit 8, converted into a digital signal by the A/D converter 44, and computed as an interelectrode voltage (test liquid voltage) Vs1 when the impedance reducing circuit 10 is connected by the microcomputer 13 (STEP G88).

Then, in the oxidation-reduction potential computing section 13b, an interelectrode voltage (test liquid voltage) when the impedance reducing circuit 10 is unconnected, i.e., an oxidation-reduction potential Vs0, is computed by multiplying the interelectrode voltage (test liquid voltage) Vs1 when the impedance reducing circuit 10 is connected by the comparison coefficient k1 which is stored in the comparison coefficient storing section 12a, as shown in the above computing equation (2) (STEP G89). The result is displayed on the display (STEP G90).

Then, the reducing circuit switching switch (Sw1) 11 is turned off based on an OFF control signal from the port P1 of the microcomputer 13, and the water immersion measurement switching switch (Sw7) 53 is turned on based on an ON control signal from the port P7 of the microcomputer 13 (STEP G91). Subsequently, the present potentiometer can return to STEP G84 and repeat the processes.

EXAMPLE 6

Figure 18:
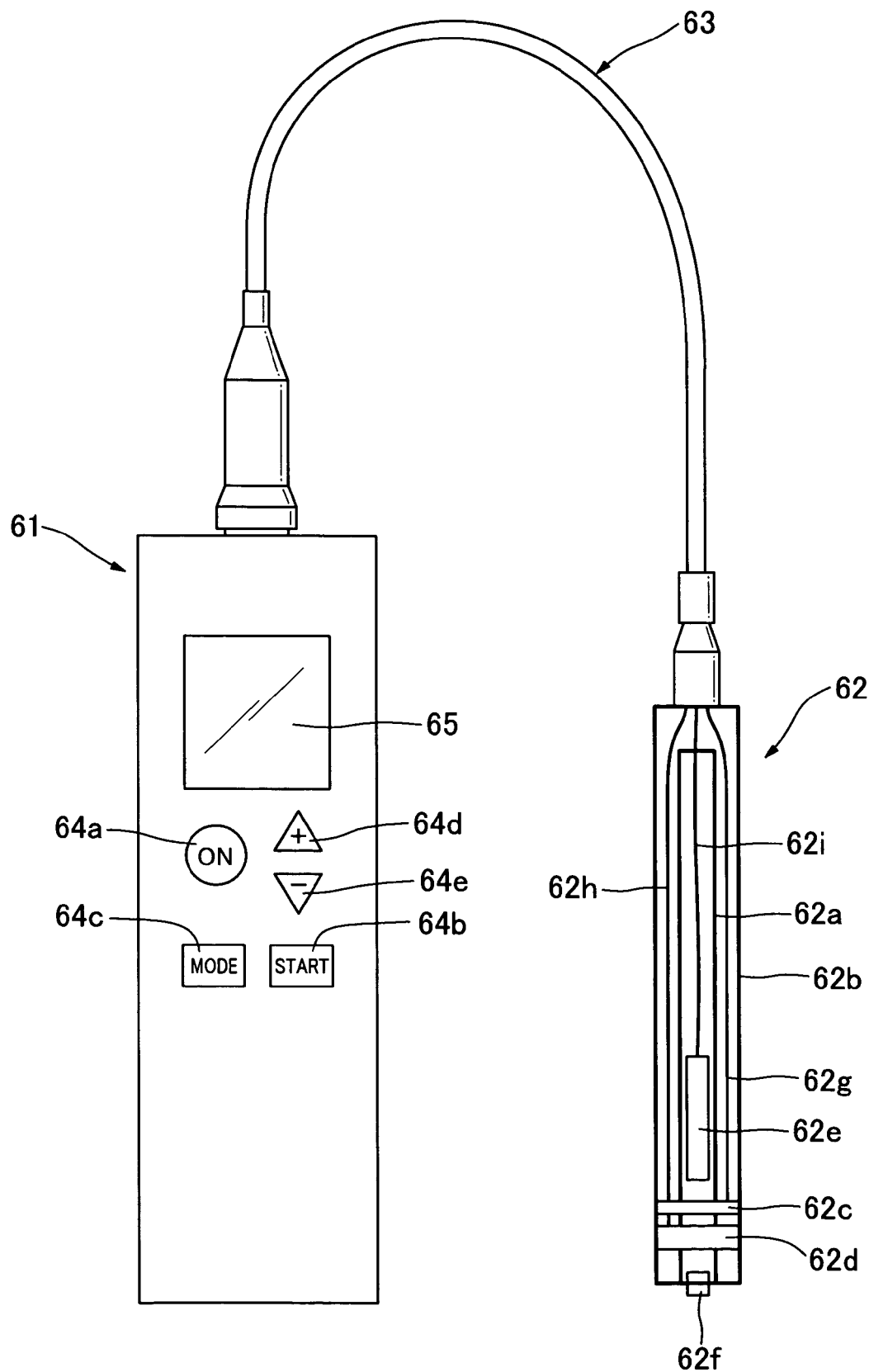
FIG. 18 is an external view of an oxidation-reduction potentiometer. (Examples 6 and 7)
Figure 19:
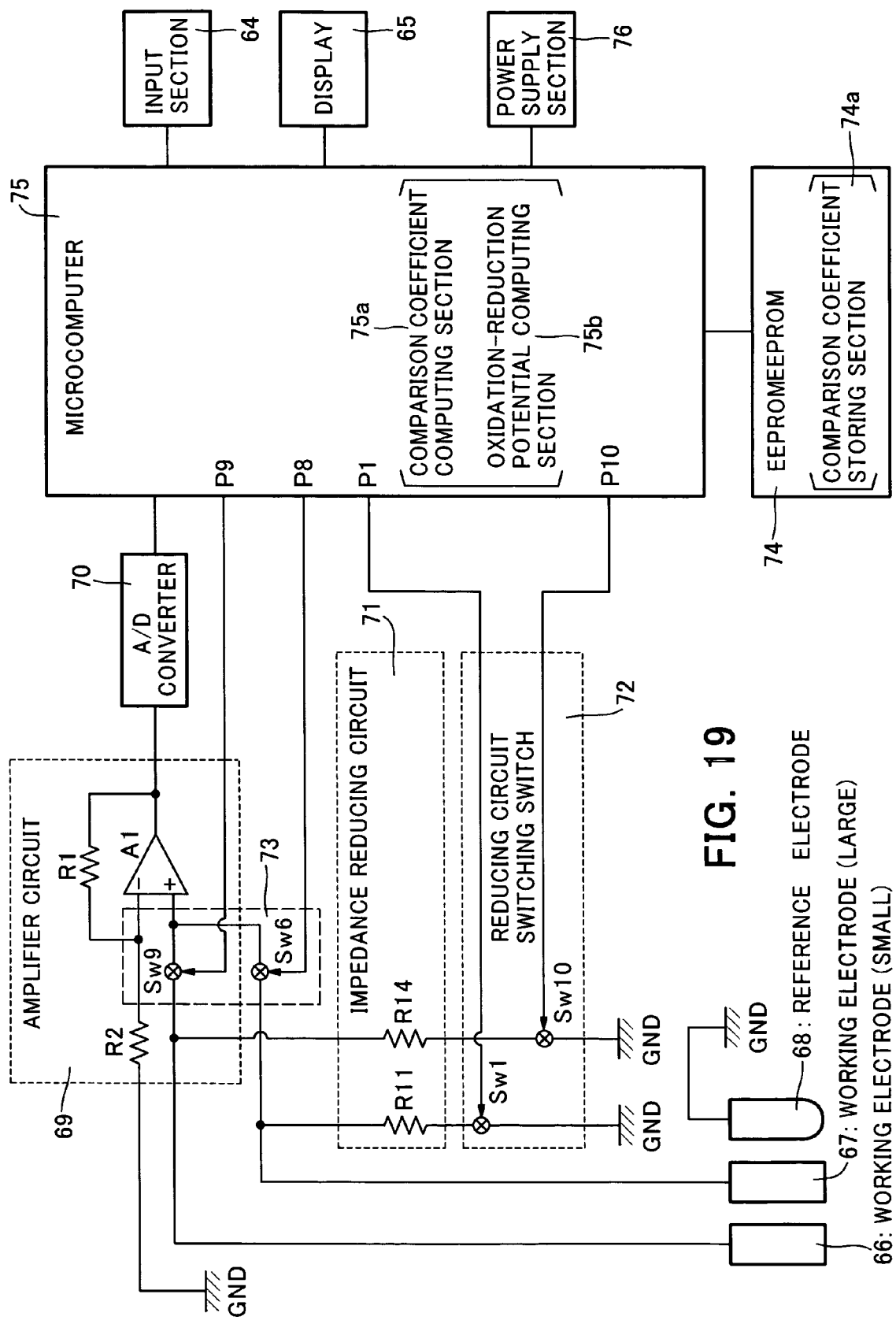
FIG. 19 is a block diagram illustrating the oxidation-reduction potentiometer. (Example 6)

First, the specific constitution of an oxidation-reduction potentiometer according to the present invention will be described by use of an external view shown in FIG. 18 and a block diagram shown in FIG. 19.

An oxidation-reduction potentiometer as Example 6 has, when viewed from the outside, a main unit 61 which has an input section 64 and a display 65 on the front side, a sensor 62 which has a small working electrode 66 having a small reaction area, a large working electrode 67 having a large reaction area and a reference electrode 68, and a cable 63 which connects the sensor 62 to the main unit 61. The oxidation-reduction potentiometer also has an electronic substrate and a power supply section 76 inside the main unit 61. The electronic substrate has an amplifier circuit 69, an A/D converter 70, an impedance reducing circuit 71, a reducing circuit switching switch 72, a working electrode switching switch 73, an EEPROM 74 and a microcomputer 75. These roughly constitute the oxidation-reduction potentiometer as a whole.

The input section 64 comprises an ON key 64a, a START key 64b, a MODE key 64c, a +key 64d and a −key 64e and is used for supplying electric power, staring a measurement, switching or the like. The ON key 64a is used to start supplying electric power from the power supply section 76 to components in the electrical system. The START key 64b is used to start a measurement. The MODE key 64c is used to switch between an adjustment mode and a measurement mode. The +key 64d and the −key 64e are used to select an item, a numerical value or the like displayed on the display 65.

The display 65 displays an input status, measurement results, various modes, remaining battery power and the like.

The sensor 62 is formed by forming an outer glass tube (shown transparent in FIG. 18) 62b on the outer side of an inner glass tube (shown transparent in FIG. 18) 62a in such a manner that the outer tube 62b covers the inner tube 62a with space therebetween, providing small platinum (Pt) 62c which has a small area and large platinum (Pt) 62d which has a large area from the outer side of the inner glass tube 62a to the outer side of the outer glass tube 62b, setting an internal electrode 62e which is silver (Ag) covered with silver chloride (AgCl) in the inner glass tube 62a, filling liquid or gelled sodium chloride (NaCl) or potassium chloride (KCl) in the inner glass tube 62a, providing a liquid junction 62f from the inside of the inner glass tube 62a to the outer sides of the inner glass tube 62a and the outer glass tube 62b, and connecting the small platinum (Pt) 62c, the large platinum (Pt) 62d and the internal electrode 62e to the electronic substrate by use of conducting wires 62g, 62h and 62i, respectively.

The small platinum (Pt) 62c portion corresponds to the small working electrode 66. The large platinum (Pt) 62d portion corresponds to the large working electrode 67. The inner glass tube 62a, the internal electrode 62e, sodium chloride (NaCl) or potassium chloride (KCl) and the liquid junction 62f correspond to the reference electrode 68.

The power supply section 76 supplies electric power to the components in the electrical system.

The amplifier circuit 69 amplifies an interelectrode voltage (analog signal) which is a difference between a measured potential generated from the small working electrode 66 or the large working electrode 67 and indicating the degree of oxidation-reduction reaction and a measured reference potential generated from the reference electrode 68. The A/D converter 70 converts the interelectrode voltage amplified by the amplifier circuit 69 into a digital signal.

The impedance reducing circuit 71 comprises a resistance R14 that is disposed between the small working electrode 66 and the reference electrode 68 such that it can be switched between an unconnected state and a connected state by the reducing circuit switching switch 72 and a resistance R11 that is disposed between the large working electrode 67 and the reference electrode 68 such that it can be switched between an unconnected state and a connected state by the reducing circuit switching switch 72. The circuit 71 reduces an impedance occurring between the small working electrode 66 and the reference electrode 68 or between the large working electrode 67 and the reference electrode 68 when the electrodes are immersed in a liquid.

The reducing circuit switching switch 72 switches the impedance reducing circuit 71 between an unconnected state and a connected state based on a control signal from the microcomputer 75. The working electrode switching switch 73 switches connection to the amplifier circuit 69 to the small working electrode 66 or the large working electrode 67 based on a control signal from the microcomputer 75.

The EEPROM 74 has a comparison coefficient storing section 74a and stores various data. The comparison coefficient storing section 74a stores comparison coefficients computed by a comparison coefficient computing section 75a which will be described later.

The microcomputer 75 has the comparison coefficient computing section 75a and an oxidation-reduction potential computing section 75b. The microcomputer 75 computes various data and controls switching of the reducing circuit switching switch and the working electrode switching switch and determinations of various data.

The comparison coefficient computing section 75a computes a comparison coefficient based on an interelectrode voltage (reference liquid voltage) from the A/D converter 70 when the impedance reducing circuit 71 is in an unconnected state and an interelectrode voltage (reference liquid voltage) between the working electrode 66 or 67 and the reference electrode 68 from the A/D converter 70 when the impedance reducing circuit 71 is in a connected state. More specifically, the comparison coefficient computing section 75a computes a comparison coefficient kg1 by dividing an interelectrode voltage Vrg0 between the large working electrode 67 and the reference electrode 68 from the A/D converter 70 when the impedance reducing circuit 71 is in an unconnected state by an interelectrode voltage Vrg1 between the large working electrode 67 and the reference electrode 68 from the A/D converter 70 when the impedance reducing circuit 71 is in a connected state, as shown in the following computing equation (9). The comparison coefficient computing section 75a also computes a comparison coefficient ks1 by dividing an interelectrode voltage Vrs0 between the small working electrode 66 and the reference electrode 68 from the A/D converter 70 when the impedance reducing circuit 71 is in an unconnected state by an interelectrode voltage Vrs1 between the small working electrode 66 and the reference electrode 68 from the A/D converter 70 when the impedance reducing circuit 71 is in a connected state, as shown in the following computing equation (10).

$$kg1 = Vrg0/Vrg1 \qquad (9)$$

$$ks1 = Vrs0/Vrs1 \qquad (10)$$

The oxidation-reduction potential computing section 75b computes an oxidation-reduction potential based on an interelectrode voltage between the working electrode 66 or 67 and the reference electrode 68 from the A/D converter 70 when the impedance reducing circuit 71 is in a connected state and the corresponding comparison coefficient stored in the comparison coefficient storing section 74a, when the impedance reducing circuit 71 has been switched to the connected state based on a control signal from the microcomputer 75. More specifically, the oxidation-reduction potential computing section 75b computes an interelectrode voltage (test liquid voltage) between the small working electrode 66 and the reference electrode 68 from the A/D converter 70 when the impedance reducing circuit 71 is in an unconnected state, i.e., an oxidation-reduction potential Vss0, by multiplying an interelectrode voltage Vss1 between the small working electrode 66 and the reference electrode 68 from the A/D converter 70 when the impedance reducing circuit 71 is in a connected state by the comparison coefficient ks1 stored in the comparison coefficient storing section 74a, as shown in the following computing equation (11). The oxidation-reduction potential computing section 75b also computes an interelectrode voltage (test liquid voltage) between the large working electrode 67 and the reference electrode 68 from the A/D converter 70 when the impedance reducing circuit 71 is in an unconnected state, i.e., an oxidation-reduction potential Vsg0, by multiplying an interelectrode voltage Vsg1 between the large working electrode 67 and the reference electrode 68 from the A/D converter 70 when the impedance reducing circuit 71 is in a connected state by the comparison coefficient kg1 stored in the comparison coefficient storing section 74a, as shown in the following computing equation (12).

$$Vss0 = ks1 \times Vss1 \qquad (11)$$

$$Vsg0 = kg1 \times Vsg1 \qquad (12)$$

The reducing circuit switching switch 72 and the microcomputer 75 constitute reducing circuit switching means. The working electrode switching switch 73 and the microcomputer 75 constitute working electrode switching means. Further, the amplifier circuit 69, the A/D converter 70 and the microcomputer 75 constitute interelectrode voltage measuring means. In addition, the reducing circuit switching means, the interelectrode voltage measuring means, the comparison coefficient computing section 75a, the comparison coefficient storing section 74a and the oxidation-reduction potential computing section 75b constitute oxidation-reduction potential measuring means.

Figure 20:
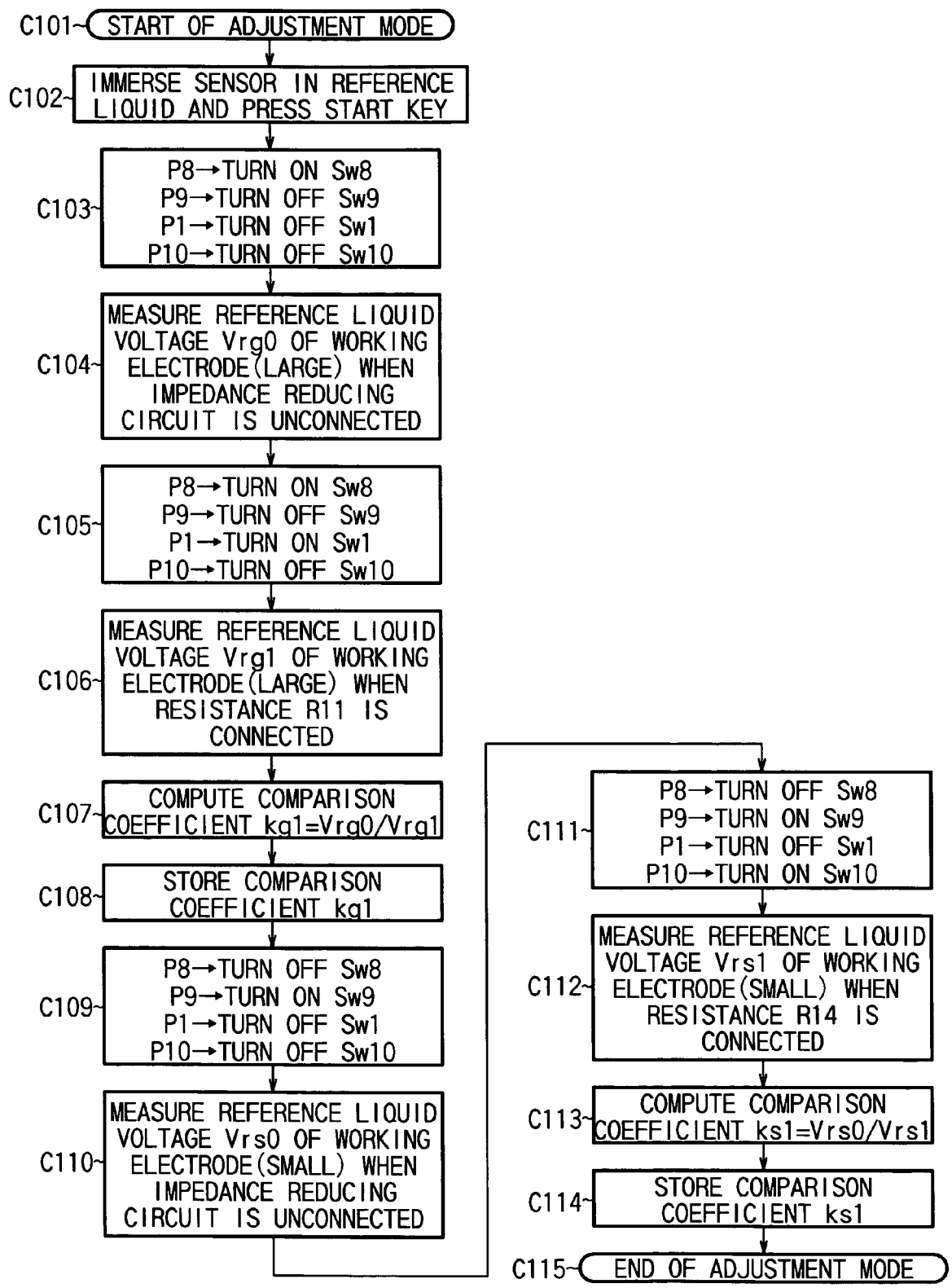
FIG. 20 is a flowchart in an adjustment mode of the oxidation-reduction potentiometer. (Example 6)

Next, specific operations of the oxidation-reduction potentiometer according to the present invention will be described by use of a flowchart in an adjustment mode shown in FIG. 20 and a flowchart in a normal mode shown in FIG. 21.

At the press of the ON key 64a, electric power is supplied from the power supply section 76 to the components in the electrical system, and the potentiometer of the present invention enters the normal mode to be described later in accordance with the flowchart shown in FIG. 21 (STEP G101). Then, when the MODE key 64c is pressed subsequently, the potentiometer enters the adjustment mode which proceeds according to the flowchart shown in FIG. 20 (STEP C101).

Then, when the sensor 62 is immersed in a reference liquid and the START key is pressed (STEP C102), the reducing circuit switching switch (Sw1, Sw10) 72 and Sw9 in the working electrode switching switch 73 are turned off based on OFF control signals from the ports P1, P10 and P9 of the microcomputer 75, Sw8 in the working electrode switching switch is turned on based on an ON control signal from the port P8 of the microcomputer 75, the large working electrode is connected to the reference electrode, and the impedance reducing circuit 71 is switched to an unconnected state (STEP C103).

Then, an interelectrode voltage (analog signal) generated between the large working electrode 67 and the reference electrode 68 at that time is amplified by the amplifier circuit 69, converted into a digital signal by the A/D converter 70, and computed as an interelectrode voltage (reference liquid voltage) Vrg0 when the impedance reducing circuit 71 is unconnected by the microcomputer 75 (STEP C104).

Then, the Sw1 in the reducing circuit switching switch 72 is turned on based on an ON control signal from the port P1 of the microcomputer 75, whereby the resistance R11 in the impedance reducing circuit 71 is switched to a connected state (STEP C105).

Then, an interelectrode voltage (analog signal) generated between the large working electrode 67 and the reference electrode 68 at that time is amplified by the amplifier circuit 69, converted into a digital signal by the A/D converter 70, and computed as an interelectrode voltage (reference liquid voltage) Vrg1 when the impedance reducing circuit 71 is connected by the microcomputer 75 (STEP C106).

Then, in the comparison coefficient computing section 75a, a comparison coefficient kg1 is computed by dividing the interelectrode voltage (reference liquid voltage) Vrg0 when the impedance reducing circuit 71 is unconnected by the interelectrode voltage (reference liquid voltage) Vrg1 when the resistance R11 is connected, as shown in the above computing equation (9) (STEP C107). The computed comparison coefficient kg1 is stored in the comparison coefficient storing section 74a (STEP C108).

Then, the Sw1 in the reducing circuit switching switch 72 and the Sw8 in the working electrode switching switch 73 are turned off based on OFF control signals from the ports P1 and P8 of the microcomputer 75, the Sw9 in the working electrode switching switch 73 is turned on based on an ON control signal from the port P9 of the microcomputer 75, the small working electrode is connected to the reference electrode, and the impedance reducing circuit is switched to an unconnected state (STEP C109).

Then, an interelectrode voltage (analog signal) generated between the small working electrode 66 and the reference electrode 68 at that time is amplified by the amplifier circuit 69, converted into a digital signal by the A/D converter 70, and computed as an interelectrode voltage (reference liquid voltage) Vrs0 when the impedance reducing circuit 71 is unconnected by the microcomputer 75 (STEP C110).

Then, the Sw10 in the reducing circuit switching switch 72 is turned on based on an ON control signal from the port P10 of the microcomputer 75, whereby the resistance R14 in the impedance reducing circuit 71 is switched to a connected state (STEP C111).

Then, an interelectrode voltage (analog signal) generated between the small working electrode 66 and the reference electrode 68 at that time is amplified by the amplifier circuit 69, converted into a digital signal by the A/D converter 70, and computed as an interelectrode voltage (reference liquid voltage) Vrs1 when the impedance reducing circuit 71 is connected by the microcomputer 75 (STEP C112).

Then, in the comparison coefficient computing section 75a, a comparison coefficient ks1 is computed by dividing the interelectrode voltage (reference liquid voltage) Vrs0 when the impedance reducing circuit 71 is unconnected by the interelectrode voltage (reference liquid voltage) Vrs1 when the resistance R14 is connected, as shown in the above computing equation (10) (STEP C113). After the computed comparison coefficient ks1 is stored in the comparison coefficient storing section 74a (STEP C114), the adjustment mode is ended (STEP C115).

Next, specific operations of the oxidation-reduction potentiometer according to the present invention in the normal mode will be described in detail.

Figure 21:
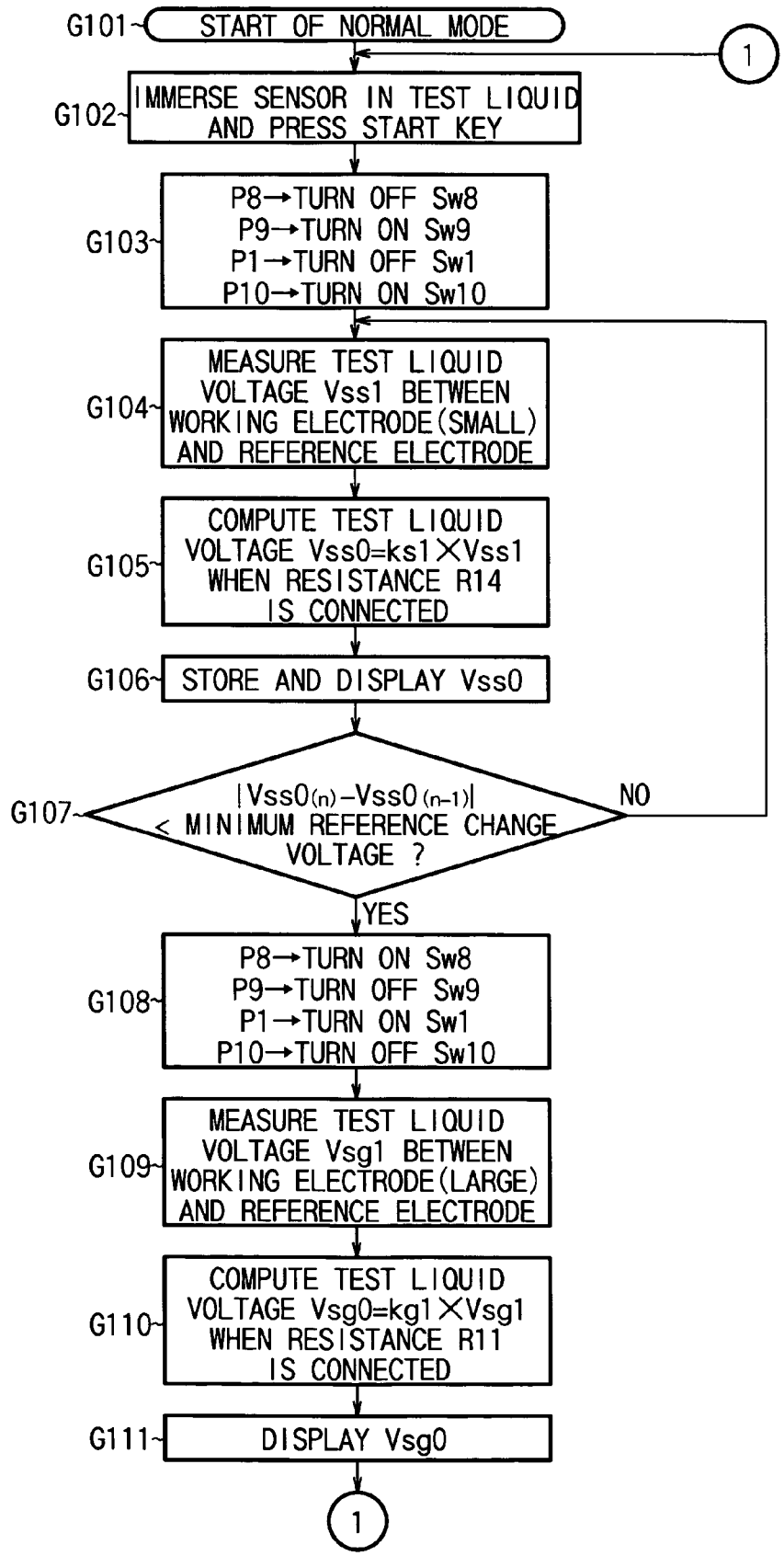
FIG. 21 is a flowchart in a normal mode of the oxidation-reduction potentiometer. (Example 6)

Immediately after the ON key 64a is pressed or after the adjustment mode is ended, the potentiometer of the present invention enters the normal mode which proceeds according to the flowchart shown in FIG. 21 (STEP G101).

Then, when the sensor 62 is immersed in a test liquid and the START key 64b is pressed (STEP G102), the Sw1 in the reducing circuit switching switch 72 and the Sw8 in the working electrode switching switch 73 are turned off based on OFF control signals from the ports P1 and P8 of the microcomputer 75, the Sw10 in the reducing circuit switching switch 72 and the Sw9 in the working electrode switching switch 73 are turned on based on ON control signals from the ports P10 and P9 of the microcomputer 75, the small working electrode is connected to the reference electrode, and the resistance R10 in the impedance reducing circuit 71 is switched to a connected state (STEP G103).

Then, an interelectrode voltage (analog signal) generated between the small working electrode 66 and the reference electrode 68 at that time is amplified by the amplifier circuit 69, converted into a digital signal by the A/D converter 70, and computed as an interelectrode voltage (test liquid voltage) Vss1 when the impedance reducing circuit 71 is connected by the microcomputer 75 (STEP G104).

Then, in the oxidation-reduction potential computing section 75b, an interelectrode voltage (test liquid voltage) when the impedance reducing circuit 71 is connected, i.e., an oxidation-reduction potential Vss0, is computed by multiplying the interelectrode voltage (test liquid voltage) Vss1 when the impedance reducing circuit 71 is connected by the comparison coefficient ks1 which is stored in the comparison coefficient storing section 74a, as shown in the above computing equation (11) (STEP G105). The result is stored in the EEPROM 74 and displayed on the display 65 (STEP G106).

Then, the microcomputer 75 determines whether the absolute value (amount of change in measured voltages) of the difference between the oxidation-reduction potential $Vss0_{(n)}$ stored this time and the oxidation-reduction potential $Vss0_{(n-2)}$ stored last time is smaller than the minimum reference change voltage (STEP G107).

Then, when the absolute value is not smaller than the minimum reference change voltage (NO in STEP G107), the potentiometer returns to STEP G104 and repeats the processes. Meanwhile, when the absolute value is smaller than the minimum reference change voltage (YES in STEP G107), the Sw10 in the reducing circuit switching switch 72 and the Sw9 in the working electrode switching switch 73 are turned off based on OFF control signals from the ports P10 and P9 of the microcomputer 75, the Sw1 in the reducing circuit switching switch 72 and the Sw8 in the working electrode switching switch 73 are turned on based on ON control signals from the ports P1 and P8 of the microcomputer 75, the large working electrode is connected to the reference electrode, and the resistance R11 in the impedance reducing circuit 71 is switched to a connected state (STEP G108).

Then, an interelectrode voltage (analog signal) generated between the large working electrode 67 and the reference electrode 68 at that time is amplified by the amplifier circuit 69, converted into a digital signal by the A/D converter 70, and computed as an interelectrode voltage (test liquid voltage) Vsg1 when the impedance reducing circuit 71 is connected by the microcomputer 75 (STEP G109).

Then, in the oxidation-reduction potential computing section 75b, an interelectrode voltage (test liquid voltage) when the impedance reducing circuit 71 is unconnected, i.e., an oxidation-reduction potential Vsg0, is computed by multiplying the interelectrode voltage (test liquid voltage) Vsg1 when the impedance reducing circuit 71 is connected by the comparison coefficient kg1 which is stored in the comparison coefficient storing section 74a, as shown in the above computing equation (12) (STEP G110). The result is stored in the EEPROM 74 and displayed on the display 65 (STEP G111).

Subsequently, the present potentiometer can return to STEP G102 and repeat the processes.

EXAMPLE 7

Figure 22:
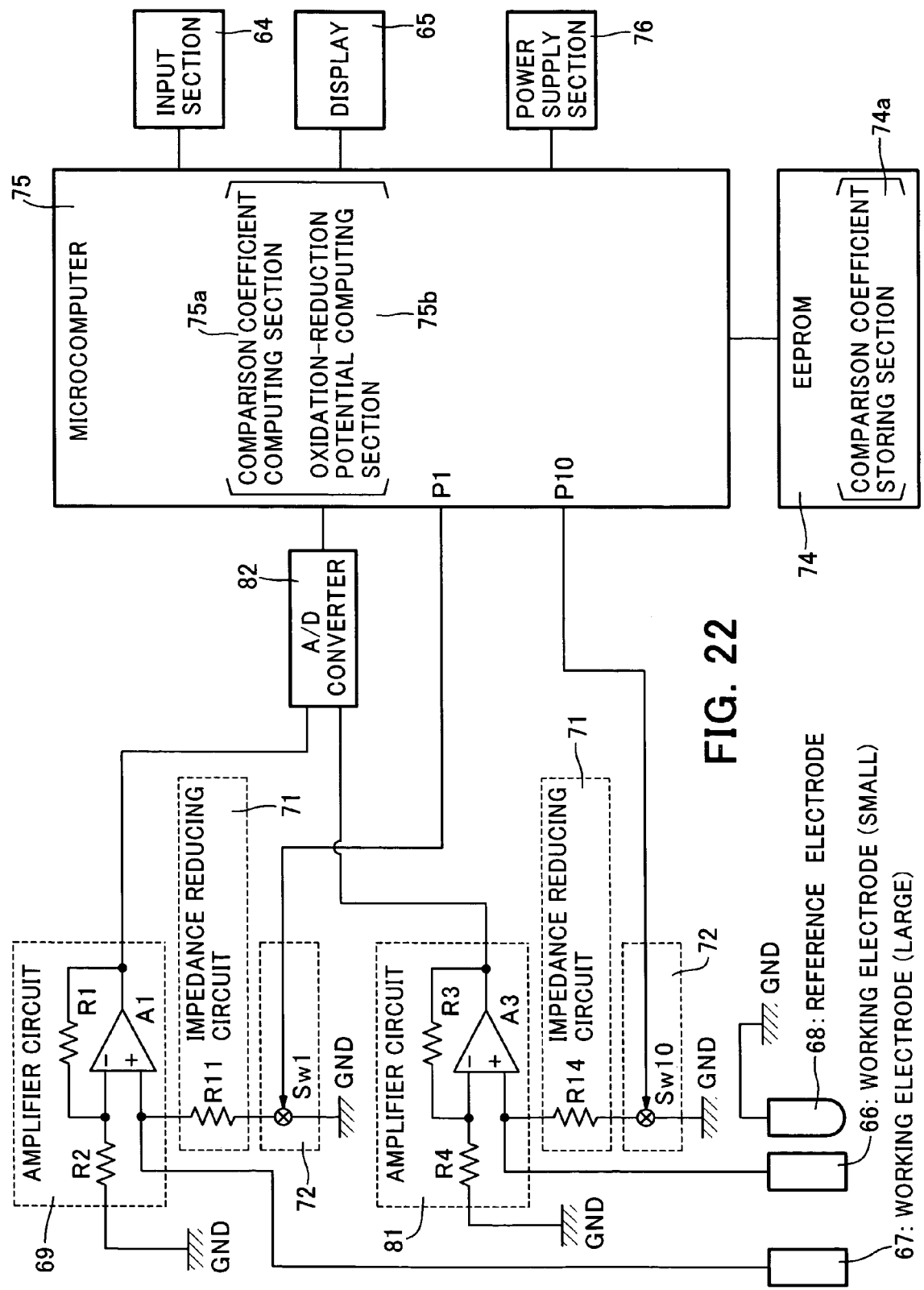
FIG. 22 is a block diagram illustrating the oxidation-reduction potentiometer. (Example 7)

First, the specific constitution of an oxidation-reduction potentiometer according to the present invention will be described by use of an external view shown in FIG. 18 and a block diagram shown in FIG. 22.

An oxidation-reduction potentiometer as Example 7 has, when viewed from the outside, a main unit 61 which has an input section 64 and a display 65 on the front side, a sensor 62 which has a small working electrode 66 having a small reaction area, a large working electrode 67 having a large reaction area and a reference electrode 68, and a cable 63 which connects the sensor 62 to the main unit 61. The oxidation-reduction potentiometer also has an electronic substrate and a power supply section 76 inside the main unit 61. The electronic substrate has amplifier circuits 69 and 81, an A/D converter 82, an impedance reducing circuit 71, a reducing circuit switching switch 72, an EEPROM 74 and a microcomputer 75. These roughly constitute the oxidation-reduction potentiometer as a whole.

Detailed descriptions of the input section 64, display 65, sensor 62, power supply section 76, impedance reducing circuit 71, reducing circuit switching switch 12, EEPROM 74, comparison coefficient computing section 75a and oxidation-reduction potential computing section 75b are omitted because they are the same as those in Example 6.

The amplifier circuit 81 amplifies an interelectrode voltage (analog signal) which is a difference between a measured potential generated from the small working electrode 66 and indicating the degree of oxidation-reduction reaction and a measured reference potential generated from the reference electrode 68. The amplifier circuit 69 amplifies an interelectrode voltage (analog signal) which is a difference between a measured potential generated from the large working electrode 67 and indicating the degree of oxidation-reduction reaction and a measured reference potential generated from the reference electrode 68. The A/D converter 82 converts the interelectrode voltage amplified by the amplifier circuit 69 or 81 into a digital signal.

The microcomputer 75 has the comparison coefficient computing section 75a and the oxidation-reduction potential computing section 75b. The microcomputer 75 computes various data and controls switching of the reducing circuit switching switch 72 and taking in an interelectrode voltage from the A/D converter 82 and determinations of various data.

Figure 23:
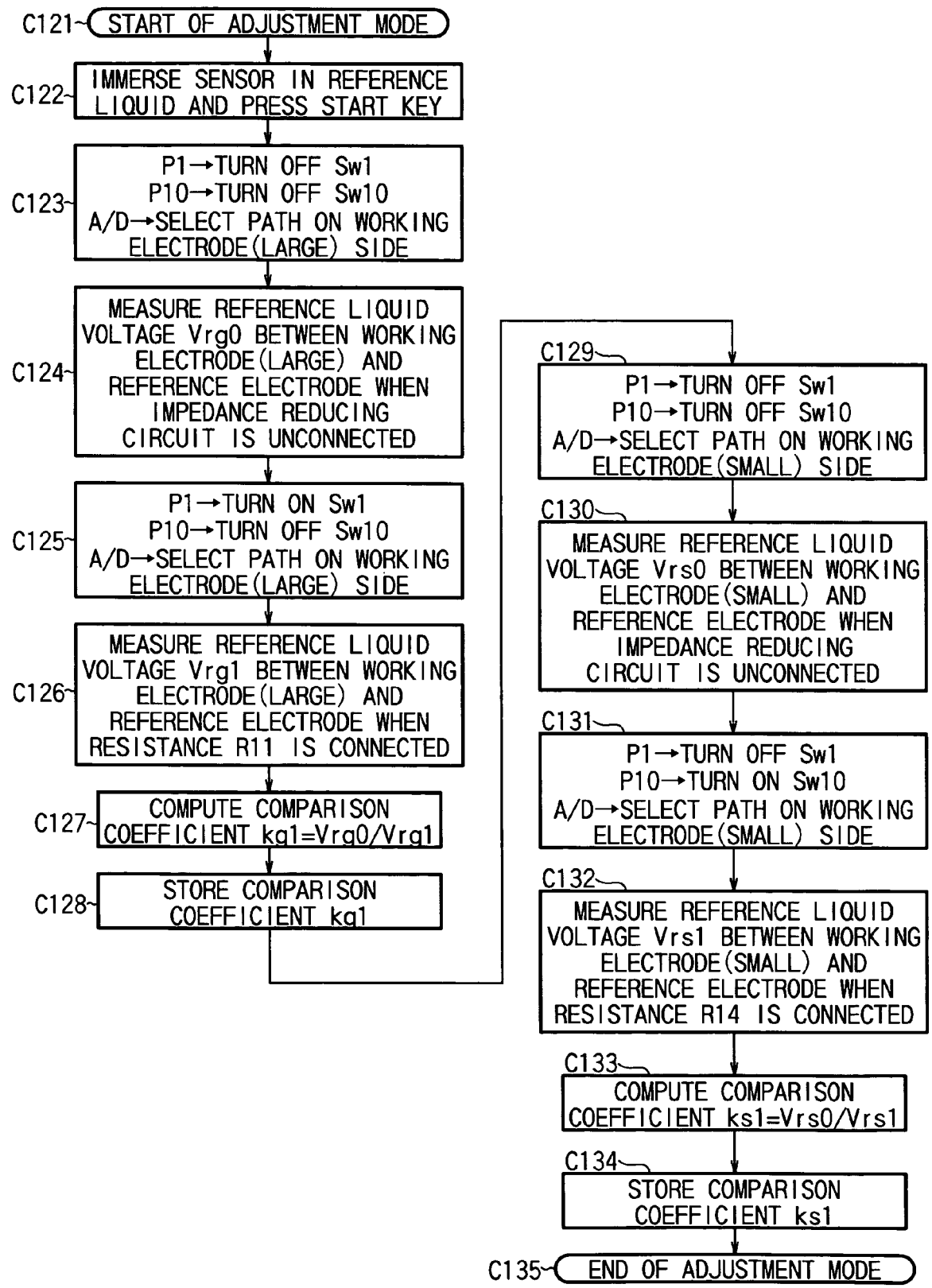
FIG. 23 is a flowchart in an adjustment mode of the oxidation-reduction potentiometer. (Example 7)

Next, specific operations of the oxidation-reduction potentiometer according to the present invention will be described by use of a flowchart in an adjustment mode shown in FIG. 23 and a flowchart in a normal mode shown in FIG. 24.

First, specific operations in the adjustment mode will be described in detail.

At the press of an ON key 64a, electric power is supplied from the power supply section 76 to the components in the electrical system, and the potentiometer of the present invention enters the normal mode to be described later in accordance with the flowchart shown in FIG. 24 (STEP G121). Then, when a MODE key 64c is pressed subsequently, the potentiometer enters the adjustment mode which proceeds according to the flowchart shown in FIG. 23 (STEP C121).

Then, when the sensor 62 is immersed in a reference liquid and a START key is pressed (STEP C122), the reducing circuit switching switch (Sw1, Sw10) 72 is turned off based on OFF control signals from the ports P1 and P10 of the microcomputer 75, the A/D converter 82 selects the path on the large working electrode side, the large working electrode is connected to the reference electrode, and the impedance reducing circuit 71 is switched to an unconnected state (STEP C123).

Then, an interelectrode voltage (analog signal) generated between the large working electrode 67 and the reference electrode 68 at that time is amplified by the amplifier circuit 69, converted into a digital signal by the A/D converter 82, and computed as an interelectrode voltage (reference liquid voltage) Vrg0 when the impedance reducing circuit 71 is unconnected by the microcomputer 75 (STEP C124).

Then, the Sw1 in the reducing circuit switching switch 72 is turned on based on an ON control signal from the port P1 of the microcomputer 75, whereby the resistance R11 in the impedance reducing circuit 71 is switched to a connected state (STEP C125).

Then, an interelectrode voltage (analog signal) generated between the large working electrode 67 and the reference electrode 68 at that time is amplified by the amplifier circuit 69, converted into a digital signal by the A/D converter 82, and computed as an interelectrode voltage (reference liquid voltage) Vrg1 when the impedance reducing circuit 71 is connected by the microcomputer 75 (STEP C126).

Then, in the comparison coefficient computing section 75a, a comparison coefficient kg1 is computed by dividing the interelectrode voltage (reference liquid voltage) Vrg0 when the impedance reducing circuit 71 is unconnected by the interelectrode voltage (reference liquid voltage) Vrg1 when the impedance reducing circuit 71 is connected, as shown in the above computing equation (9) (STEP C127). The computed comparison coefficient kg1 is stored in the comparison coefficient storing section 74a (STEP C128).

Then, the Sw1 in the reducing circuit switching switch 72 is turned off based on an OFF control signal from the port P1 of the microcomputer 75, the A/D converter 82 selects the path on the small working electrode side, the small working electrode is connected to the reference electrode, and the impedance reducing circuit 71 is switched to an unconnected state (STEP C129).

Then, an interelectrode voltage (analog signal) generated between the small working electrode 66 and the reference electrode 68 at that time is amplified by the amplifier circuit 81, converted into a digital signal by the A/D converter 82, and computed as an interelectrode voltage (reference liquid voltage) Vrs0 when the impedance reducing circuit 71 is unconnected by the microcomputer 75 (STEP C130).

Then, the Sw10 in the reducing circuit switching switch 72 is turned on based on an ON control signal from the port P10 of the microcomputer 75, whereby the R14 in the impedance reducing circuit 71 is switched to a connected state (STEP C131).

Then, an interelectrode voltage (analog signal) generated between the small working electrode 66 and the reference electrode 68 at that time is amplified by the amplifier circuit 81, converted into a digital signal by the A/D converter 82, and computed as an interelectrode voltage (reference liquid voltage) Vrs1 when the impedance reducing circuit 71 is connected by the microcomputer 75 (STEP C132).

Then, in the comparison coefficient computing section 75a, a comparison coefficient ks1 is computed by dividing the interelectrode voltage (reference liquid voltage) Vrs0 when the impedance reducing circuit 71 is unconnected by the interelectrode voltage (reference liquid voltage) Vrs1 when the impedance reducing circuit 71 is connected, as shown in the above computing equation (10) (STEP C133). After the computed comparison coefficient ks1 is stored in the comparison coefficient storing section 74a (STEP C134), the adjustment mode is ended (STEP C135).

Next, specific operations of the oxidation-reduction potentiometer according to the present invention in the normal mode will be described in detail.

Figure 24:
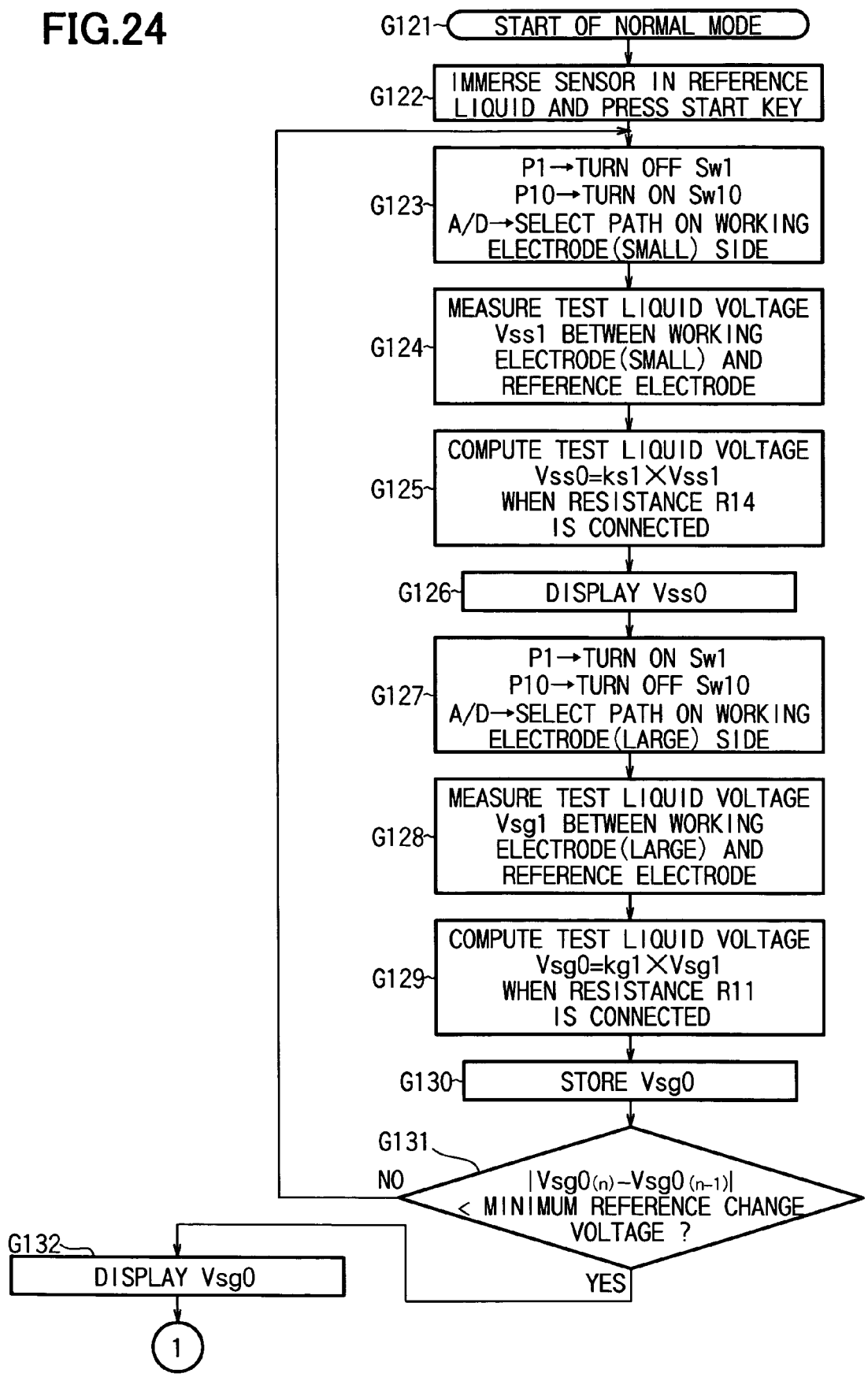
FIG. 24 is a flowchart in a normal mode of the oxidation-reduction potentiometer. (Example 7)

Immediately after the ON key 64a is pressed or after the adjustment mode is ended, the potentiometer of the present invention enters the normal mode which proceeds according to the flowchart shown in FIG. 24 (STEP G121).

Then, when the sensor 62 is immersed in a test liquid and the START key 64b is pressed (STEP G122), the Sw1 in the reducing circuit switching switch 72 is turned off based on an OFF control signal from the port P1 of the microcomputer 75, the Sw10 in the reducing circuit switching switch 72 is turned on based on an ON control signal from the port P10 of the microcomputer 75, the A/D converter 82 selects the path on the small working electrode side, the small working electrode is connected to the reference electrode, and the impedance reducing circuit is switched to a connected state (STEP G123).

Then, an interelectrode voltage (analog signal) generated between the small working electrode and the reference electrode at that time is amplified by the amplifier circuit, converted into a digital signal by the A/D converter, and computed as an interelectrode voltage (test liquid voltage) Vss1 when the impedance reducing circuit is connected by the microcomputer (STEP G124).

Then, in the oxidation-reduction potential computing section 75b, an interelectrode voltage (test liquid voltage) when the impedance reducing circuit 71 is connected, i.e., an oxidation-reduction potential Vss0, is computed by multiplying the interelectrode voltage (test liquid voltage) Vss1 when the impedance reducing circuit 71 is connected by the comparison coefficient ks1 which is stored in the comparison coefficient storing section 74a, as shown in the above computing equation (11) (STEP G125). The result is stored in the EEPROM 74 and displayed on the display 65 (STEP G126).

Then, the Sw1 in the reducing circuit switching switch 72 is turned on based on an ON control signal from the port P1 of the microcomputer 75, the Sw10 in the reducing circuit switching switch 72 is turned off based on an OFF control signal from the port P10 of the microcomputer 75, the A/D converter 82 selects the path on the large working electrode side, the large working electrode is connected to the reference electrode, and the R11 in the impedance reducing circuit 71 is switched to a connected state (STEP G127).

Then, an interelectrode voltage (analog signal) generated between the large working electrode 67 and the reference electrode 68 at that time is amplified by the amplifier circuit 69, converted into a digital signal by the A/D converter 82, and computed as an interelectrode voltage (test liquid voltage) Vsg1 when the impedance reducing circuit 71 is connected by the microcomputer 75 (STEP G128).

Then, in the oxidation-reduction potential computing section 75b, an interelectrode voltage (test liquid voltage) when the impedance reducing circuit 71 is connected, i.e., an oxidation-reduction potential Vsg0, is computed by multiplying the interelectrode voltage (test liquid voltage) Vsg1 when the impedance reducing circuit 71 is connected by the comparison coefficient kg1 which is stored in the comparison coefficient storing section 74a, as shown in the above computing equation (12) (STEP G129). The result is stored in the EEPROM 74 (STEP G130).

Then, the microcomputer 75 determines whether the absolute value (amount of change in measured voltages) of the difference between the oxidation-reduction potential $Vsg0(n)$ stored this time and the oxidation-reduction potential $Vsg0_{(n-1)}$ stored last time is smaller than the minimum reference change voltage (STEP G131).

Then, when the absolute value is not smaller than the minimum reference change voltage (NO in STEP G131), the potentiometer returns to STEP G123 and repeats the processes. Meanwhile, when the absolute value is smaller than the minimum reference change voltage (YES in STEP G131), the oxidation-reduction potential Vsg0 computed this time is displayed on the display 65 (STEP G132).

Subsequently, the present potentiometer can return to STEP G122 and repeat the processes.

What is claimed is:

1. An oxidation-reduction potentiometer comprising:
a working electrode,
a reference electrode,
an impedance reducing circuit, and
oxidation-reduction potential measuring means,
wherein
the working electrode generates a potential indicating the degree of oxidation-reduction reaction when immersed in a liquid,
the reference electrode generates a reference potential when immersed in the liquid,
the impedance reducing circuit reduces an impedance which occurs between the working electrode and the reference electrode when the electrodes are immersed in the liquid,
the oxidation-reduction potential measuring means measures an oxidation-reduction potential based on an interelectrode voltage which is a difference between the potential generated from the working electrode indicating the degree of oxidation-reduction reaction and the reference potential generated from the reference electrode in reducing the impedance by the impedance reducing circuit, and
the oxidation-reduction potential measuring means comprises:
reducing circuit switching means,
interelectrode voltage measuring means,
a comparison coefficient computing section,
a comparison coefficient storing section, and
an oxidation-reduction potential computing section,
wherein
the reducing circuit switching means switches the impedance reducing circuit to an unconnected state and to a connected state between the working electrode and the reference electrode,
the interelectrode voltage measuring means measures an interelectrode voltage, which is a difference between a potential generated from the working electrode indicating the degree of oxidation-reduction reaction and a reference potential generated from the reference electrode, when the impedance reducing circuit has been switched to the unconnected state and when the impedance reducing circuit has been switched to the connected state by the reducing circuit switching means,
the comparison coefficient computing section computes, in an adjustment mode, a comparison coefficient by dividing the interelectrode voltage in the unconnected state by the interelectrode voltage in the connected state, wherein said interelectrode voltages are measured when the electrodes are immersed in a reference liquid,
the comparison coefficient storing section stores the comparison coefficient computed by the comparison coefficient computing section, and
the oxidation-reduction potential computing section computes, in a normal mode, an oxidation-reduction potential as the interelectrode voltage in the unconnected state by multiplying the interelectrode voltage in the connected state, measured by the interelectrode voltage measuring means when the impedance reducing circuit has been switched to the connected state and the electrodes are immersed in a test liquid, by the comparison coefficient stored in the comparison coefficient storing section.

2. The oxidation-reduction potentiometer according to claim 1, further comprising:
   conductivity measuring means, and
   conductivity measurement switching means,
   wherein
   the conductivity measuring means measures the conductivity of the liquid,
   the conductivity measurement switching means switches between measurement of interelectrode voltage by the interelectrode voltage measuring means and measurement of conductivity by the conductivity measuring means,
   the comparison coefficient storing section stores comparison coefficients for a plurality of liquids having different conductivities which have been computed by the comparison coefficient computing section based on switching between the measurement of interelectrode voltage and the measurement of conductivity by the conductivity measurement switching means, and
   the oxidation-reduction potential computing section computes an oxidation-reduction potential based on an interelectrode voltage in a connected state which has been measured by the interelectrode voltage measuring means when the impedance reducing circuit has been switched to the connected state by the reducing circuit switching means and a comparison coefficient corresponding to the conductivity of the liquid measured by the conductivity measuring means out of the comparison coefficients for the liquids having different conductivities stored in the comparison coefficient storing section.

3. The oxidation-reduction potentiometer according to claim 1 or 2, further comprising:
   water immersion measuring means,
   wherein
   the water immersion measuring means measures that the working electrode and the reference electrode are immersed in the liquid, prior to measurement of the oxidation-reduction potential by the oxidation-reduction potential measuring means, and
   the reducing circuit switching means keeps the impedance reducing circuit switched to an unconnected state during the measurement by the water immersion measuring means.

4. The oxidation-reduction potentiometer according to any one of claims 1, 2, and 3, wherein
   the working electrode comprises a plurality of working electrodes having different areas,
   the potentiometer further comprises working electrode switching means for switching connection to the interelectrode voltage measuring means to a working electrode out of the working electrodes having different areas,
   the impedance reducing circuit reduces an impedance occurring between each of the working electrodes having different areas and the reference electrode,
   the reducing circuit switching means switches the impedance reducing circuit to an unconnected state and to a connected state between each of the working electrodes having different areas and the reference electrode,
   the interelectrode voltage measuring means measures an interelectrode voltage which is a difference between a potential indicating the degree of oxidation-reduction reaction and generated from each of the working electrodes having different areas and a reference potential generated from the reference electrode, when the impedance reducing circuit has been switched to the unconnected state and the connected state by the reducing circuit switching means,
   the comparison coefficient computing section computes a comparison coefficient based on the interelectrode voltage in the unconnected state and the interelectrode voltage in the connected state which have been measured by the interelectrode voltage measuring means,
   the comparison coefficient storing section stores the comparison coefficients computed by the comparison coefficient computing section, and
   the oxidation-reduction potential computing section computes an oxidation-reduction potential based on the interelectrode voltage in the connected state which has been measured by the interelectrode voltage measuring means when the impedance reducing circuit has been switched to the connected state by the reducing circuit switching means and a corresponding comparison coefficient out of the comparison coefficients stored in the comparison coefficient storing section, the computation of the oxidation-reduction potential being performed for each of the working electrodes having different areas in the order of area from smallest to largest.

5. The oxidation-reduction potentiometer according to any one of claims 1 and 2 to 4, wherein
   the impedance reducing circuit connects the working electrode and the reference electrode only by a reduction resistance.

6. The oxidation-reduction potentiometer according to any one of claims 1 and 2 to 4, wherein
   the impedance reducing circuit comprises:
   voltage generating circuits which generate a voltage,
   a voltage follower which is connected to the voltage generating circuits, and
   an output resistance which is connected between the voltage follower and the working electrode.

7. The oxidation-reduction potentiometer according to any one of claims 1 and 2 to 4, wherein
   the impedance reducing circuit reduces an impedance occurring between the working electrode and the reference electrode in multiple levels,
   the reducing circuit switching means switches the impedance reducing circuit to a connected state in multiple levels,
   the interelectrode voltage measuring means measures an interelectrode voltage of each level when the impedance reducing circuit has been switched to the connected state in multiple levels,
   the comparison coefficient computing section computes a comparison coefficient of each level based on the interelectrode voltage of the corresponding level in the connected state which has been measured by the interelectrode voltage measuring means,
   the comparison coefficient storing section stores the comparison coefficient of each level which has been computed by the comparison coefficient computing section, and
   the oxidation-reduction potential computing section computes an oxidation-reduction potential value based on an interelectrode voltage in a connected state which has been measured by the interelectrode voltage measuring means when the impedance reducing circuit has been switched to the connected state of a specific level by the reducing circuit switching means and a comparison coefficient of the corresponding level out of the comparison coefficients of multiple levels stored in the comparison coefficient storing section.

8. The oxidation-reduction potentiometer according to claim 7, wherein
the impedance reducing circuit connects the working electrode and the reference electrode in parallel only by a plurality of reduction resistances.

9. The oxidation-reduction potentiometer according to claim 7, wherein the impedance reducing circuit comprises:

voltage generating circuits which generate a voltage in multiple levels, a voltage follower which is connected to the voltage generating circuits, and an output resistance which is connected between the voltage follower and the working electrode.

* * * * *